(12) United States Patent
Averett

(10) Patent No.: US 7,576,068 B2
(45) Date of Patent: Aug. 18, 2009

(54) ADMINISTRATION OF TLR7 LIGANDS AND PRODRUGS THEREOF FOR TREATMENT OF INFECTION BY HEPATITIS C VIRUS

(75) Inventor: Devron R. Averett, Cardiff By The Sea, CA (US)

(73) Assignee: Anadys Pharmaceuticals, Inc., San Diego, CA (US)

(*) Notice: Subject to any disclaimer, the term of this patent is extended or adjusted under 35 U.S.C. 154(b) by 645 days.

(21) Appl. No.: 10/931,130

(22) Filed: Sep. 1, 2004

(65) Prior Publication Data

US 2005/0054590 A1 Mar. 10, 2005

Related U.S. Application Data

(60) Provisional application No. 60/500,339, filed on Sep. 5, 2003, provisional application No. 60/518,996, filed on Nov. 10, 2003, provisional application No. 60/518,997, filed on Nov. 10, 2003.

(51) Int. Cl.
*A01N 43/04* (2006.01)
*A61K 31/70* (2006.01)

(52) U.S. Cl. .............................. 514/45; 514/43; 514/46; 514/47; 514/48

(58) Field of Classification Search .................. None
See application file for complete search history.

(56) References Cited

U.S. PATENT DOCUMENTS

| | | | |
|---|---|---|---|
| 4,539,205 A | 9/1985 | Goodman et al. | |
| 4,643,992 A | 2/1987 | Goodman et al. | |
| 4,880,784 A | 11/1989 | Robins et al. | |
| 5,011,828 A | 4/1991 | Goodman et al. | |
| 5,041,426 A | 8/1991 | Robins et al. | |
| 5,395,937 A | 3/1995 | Nikolaides et al. | |
| 5,821,236 A | 10/1998 | Krenitsky et al. | |
| 5,994,321 A | 11/1999 | Lewis et al. | |
| 6,028,076 A | 2/2000 | Hirota et al. | |
| 6,329,381 B1 | 12/2001 | Kurimoto et al. | |
| 6,376,501 B1 | 4/2002 | Isobe et al. | |
| 2002/0173655 A1 | 11/2002 | Dellaria et al. | |
| 2003/0065005 A1 | 4/2003 | Charles et al. | |
| 2003/0100764 A1 | 5/2003 | Bonk et al. | |
| 2003/0162806 A1 | 8/2003 | Dellaria et al. | |
| 2003/0176458 A1 | 9/2003 | Dellaria et al. | |
| 2003/0186949 A1 | 10/2003 | Dellaria et al. | |
| 2003/0195209 A1 | 10/2003 | Dellaria et al. | |
| 2003/0199461 A1 | 10/2003 | Averett et al. | |
| 2004/0063658 A1 | 4/2004 | Roberts et al. | |
| 2005/0004144 A1 | 1/2005 | Carson et al. | |

FOREIGN PATENT DOCUMENTS

| | | |
|---|---|---|
| EP | 0 882 727 | 9/1998 |
| EP | 1 035 123 | 9/2000 |
| EP | 1 043 021 | 10/2000 |
| EP | 1 386 923 A1 | 2/2004 |
| WO | WO-94/07904 | 4/1994 |
| WO | WO-94/17043 | 8/1994 |
| WO | WO-98/17279 | 4/1998 |
| WO | WO-03/045968 | 6/2003 |
| WO | WO 03/049670 A2 * | 6/2003 |

OTHER PUBLICATIONS

Werner et al. Eur. J. Biochem. (1996), vol. 242, pp. 1-19.*
Naylor et al. International Immunopharmacology (2003), vol. 3, pp. 1205-1215.*
Pope et al. The Journal of Immunology (1993), vol. 151, pp. 3007-3017.*
Lee et al. PNAS (2003), vol. 100, pp. 6646-6651.*
Neumann et al. Science (1998), vol. 282, pp. 103-107.*
Akira, "Mammalian Toll-like receptors", *Current Opinion*, 2003, 15: 5-11.
Akira, "Toll-Like Receptor Signalling", *Immunology*, 2004, 4:499-511.
Alexander et al., "(Acyloxy)alkyl Carbamates as Novel Bioreversible Prodrugs for Amines: Increased Permeation through Biological Membranes", J. Med. Chem., 1988, 31:318-322.
Applequist et al., "Variable expression of Toll-like receptor in murine innate and adaptive immune cell lines", *Int. Immunol.*, 2002, 14(9):1065-74.
Barrio et al., "Regioselective Fluorination of Substituted Guanines with Dilute $F_2$: A Facile Entry to 8-Fluoroguanine Derivatives", *J. Org. Chem.*, 1996, 61:6084-6085.
Bottcher et al., "Differential regulation of Toll-like receptor mRNAs in experimental murine central nervous system infections", *Neurosci. Lett.*, 2003, 344(1):17-20.
Bruno et al., "Mouse pre-immunocytes as non-proliferating multipotent precursors of macrophages, interferon-producing cells, $CD8\alpha^+$ and $CD8\alpha^-$ dendritic cells", *Eur. J. Immunol.*, 2001, 31(11):3403-12.
Chuang et al., "Cloning and characterization of a sub-family of human Toll-like receptors: hTLR7, hTLR8 and hTLR9", *Eur. Cytokine Netw.*, Sep. 2000, 11(3):372-8.
Diebold et al, "Innate antiviral responses by means of TLR7-mediated recognition of single-stranded RNA", *Science*, 2004, 303(5663):1481-2.
Doxsee et al, "The Immune Response Modifier and Toll-like Receptor 7 Agonist S-27609 Selectively Induces IL-12 and TNF-α Production in $CD11c^+CD11b^+CD8^-$ Dendritic Cells", *J. Immunol.*, 2003, 171(3):1156-63).
Du et al., *Eur. Cytokine Netw.*, 2000, 11(3), 362-71.

(Continued)

*Primary Examiner*—Patrick T Lewis
(74) *Attorney, Agent, or Firm*—Connolly Bove Lodge & Hutz LLP

(57) ABSTRACT

This invention relates to methods for treating or preventing hepatitis C virus infections in mammals using Toll-Like Receptor (TLR)7 ligands and prodrugs thereof. More particularly, this invention relates to methods of orally administering a therapeutically effective amount of one or more prodrugs of TLR7 ligands for the treatment or prevention of hepatitis C viral infection. Oral administration of these TLR7 immunomodulating ligands and prodrugs thereof to a mammal provides therapeutically effective amounts and reduced undesirable side effects.

20 Claims, 2 Drawing Sheets

OTHER PUBLICATIONS

Edwards et al., "Toll-like receptor expression in murine DC subsets: lack of TLR7 expression by CD8α+ DC correlates with unresponsiveness to imidazoquinolines", *Eur. J. Immunol.*, 2003, 33(4):827-33.

Fan et al., "Pyrimidines. 24. Analogues and Derivatives of 2-Amino-5-bromo-6-phenyl-4(3*H*)-pyrimidinone (ABPP)", *J. Heterocyclic Chem.*, Nov. 1993, 30:1273-1276.

Fried, et al., "5-Substituted 2-Amino-6-phenyl-4(3*H*)-pyrimidinones. Antiviral- and Interferon- Inducing Agents", *J. Med. Chem.*, 1980, 23:237-239.

Fujiwara et al., "Synthesis and Bioactivities of Novel Piperidylpyrimidine Derivatives: Inhibitors of Tumor Necrosis Factor-Alpha Production", *Bioorg. Med. Chem. Lett.*, 2000, 10(12):1317-1320.

Furneaux et al., "Improved Syntheses of 3*H*,5*H*-Pyrrolo[3,2-*d*]pyrimidines", *J. Org. Chem.*, 64 (22), 8411-8412 (1999).

Gangwar et al., "*Synthesis of a Novel Esterase-Sensitive Cyclic Prodrug of a Hexapeptide Using an (Acyloxy)alkoxy Promoiety*)", *J. Org. Chem.*, 1997, 62:1356-1362.

Gibson et al., "Plasmacytoid dendritic cells produce cytokines and mature in response to the TLR7 agonists, imiquimod and resiquimod", *Cell Immunol.*, 2002, 218(1-2):74-86.

Girgis et al., "Direct C-Flycosylation of Guanine Analogues: The Synthesis and Antiviral Activity of Certain 7- and 9-Deazaguanine C-Nucleosides", *J. Med. Chem.*, 1990, 33:2750-2755.

Heil et al., "The Toll-like receptor 7 (TLR7)-specific stimulus loxoribine uncovers a strong relationship within the TLR7, 8 and 9 subfamily", *Eur. J. Immunol.*, 2003, 33(11):2987-97.

Hemmi et al., "Small anti-viral compounds activate immune cells via the TLR7 MyD88-dependent signaling pathway", *Nat. Immunol.*, 2002, 3(2):196-200.

Henry et al., "Synthesis and Broad-Spectrum Antiviral Activity of 7,8-Dihydro-7-methyl-8-thioxoguanosine", *J. Med. Chem.*, 1990, 33:2127-2130.

Hirota et al., "Discovery of 8-Hydroxyadenines as a Novel Type of Interferon Inducer", *J. Med. Chem.*, 2002, 45:5419-5422.

Horng et al., "The adaptor molecule TIRAP provides signaling specificity for Toll-like receptors", *Nature*, 2002, 420(6913):329-333.

Hornung et al., "Quantitative Expression of Toll-Like Receptor 1-10 mRNA in Cellular Subsets of Human Peripheral Blood Mononuclear Cells and Sensitivity to CpG Oligodeoxynucleotides", *J. Immunol.*, 2002, 168(9):4531-4537.

International Search Report (PCT/US2004/028236) dated Mar. 14, 2005.

Isobe et al, "Synthesis and Structure-Activity Relationships of 2-Substituted-8-hydroxyadenin Derivatives as Orally Available Interferon Inducers without Emetic Side Effects", *Bioorganic & Medicinal Chemistry*, 2003, 11:3641-3647.

Ito et al., "Roles of Toll-Like Receptors in Natural Interferon-Producing Cells as Sensors in Immune Surveillance", *Hum. Immunol.*, 2002, 63(12):1120-1125.

Jarrossay, "Specialization and complementarity in microbial molecule recognition by human myeloid and plasmacytoid dendritic cells", *Eur. J. Immunol.*, 2001, 31(11):3388-3393.

Jurk et al., "Human TLR7 or TLR8 independently confer responsiveness to the antiviral compound R-848", *Nat. Immunol.*, 2002, 3(6):499.

Kerr et al, "Isatoribine, a Toll Like Receptor 7 Agonist, Significantly Reduced Plasma Viral Load in a Proof-of-Concept Study in Patients with Chronic Hepatitis C Virus Infection", . . . .

Kini et al., "Synthesis and Antiviral Activity of Certain Guanosine Analogues in the Thiazolo[4,5-*d*]pyrimidine Ring System", *J. Med. Chem.*, 34:3006-3010.

Kurimoto et al., "Prodrugs of 9-Benzyl-8-hydroxy-2-(2-hydroxyethylthio)adenine: Potent Interferon Inducing Agents in Monkeys", *Chem. Pharm. Bull.*, 2004, 52(4):466-469.

Kurimoto et al., "Synthesis and evaluation of 2-substituted 8-hydroxyadenines as potent inferferon inducers with improved oral bioavailabilities", *Bioorg. Med. Chem.*, 2004, 12:1091-1099.

Le Quesne et al., "Biomimetic Synthesis of Catechol Estrogens" Potentially Mutagenic Arene Oxide Intermediates in Estrogen Metabolism, *J. Med. Chem*, 1980, 23:239-240.

Lee et al., "Molecular basis for the immunostimulatory activity of guanine nucleoside analogs: activation of Toll-like receptor 7", *PNAS*, 2003, 100(11): 6646-6651.

Lore et al, "Toll-Like Receptor Ligands Modulate Dendritic Cells to Augment Cytomegalovirus-and HIV-1-Specific T Cell Responses", *J. Immunol.*, 2003, 171(8): 4320-4328.

Mealy, "ANA-971", *Drugs of the Future*, 2004, 29(5):507.

Mealy, "ISIS-14803—20-Mer antisense phosphorothioate oligodeoxynucleotide whose sequence is: 5'GTGCmTCmATG-GTGCmACmGGTCmT-3' where Cm represents 5-methylcytidine", *Drugs of the Future*, May 2004, 29(5):526-27.

Michael et al, "Alkylpurines as Immunopotentiating Agents. Synthesis and Antiviral Activity of Certain Alkylguanines", *J. Med. Chem.*, 1993, 36:3431-3436.

Miettinen et al., "IFNs activate toll-like receptor gene expression in viral infections", *Genes Immun.*, 2001, 2(6):349-355.

Mohty et al., "IFN-α Skews Monocyte Differentiation into Toll-Like Receptor 7-Expressing Dendritic Cells with Potent Functional Activities", *J. Immunol.*, 2003, 171(7):3385-93.

Nagase et al., "Expression and Function of Toll-Like Receptors in Eosinophils: Activation by Toll-Like Receptor 7 Ligand[1]", *J. Immunol.*, 2003, 171(8):3977-3982.

O'Neill, "After the Toll Rush", *Science*, 2004, 303:1481-1482.

Okada et al., "Murine thymic plasmacytoid dendritic cells", *Eur. J. Immunol.*, 2003, 33(4): 1012-9.

Pinhal-Enfield et al., "An Angiogenic Switch in Macrophages Involving Synergy between Toll-Like Receptors 2, 4, 7, and 9 and Adenosine $A_{2A}$ Receptors", *Am. J. Pathol.*, 2003, 163(2):711-721.

Pockros et al., "A Phase IIa Placeob-Controlled, Double-Blind Trial to Determine the Safety, Tolerability, PK/PD of An Oral Interferon Inducer, Resiquimod, in chronic HCV", *Gastroenterology*, 2003, 124(Suppl 1): A-766.

Pockros, "Attacking the Hepatitis C Virus with New Mechanisms of Action: Drugs in the Pipeline", *The HCV Advocate: Medical Writer's Circle*, May 2004, pp. 1-5.

Raney et al, "HEP DART 2003: Frontiers in Drug Development for Viral Hepatitis", *Expert Opin. Investig. Drugs*, 2004, 13(3):289-293.

Reitz, et al., "Small-Molecule Immunostimulants. Synthesis and Activity of 7,8-Disubstituted Guasnosines and Structurally Related Compounds", *J. Med. Chem.*, 1994, 37(21):3561-3578.

Revankar et al., "Synthesis and Antiviral/Antitumor Activities of Certain 3-Deazaguanine Nucleosides and Nucelotides", *J. Med. Chem.*, 1984, 27:1389-96.

Rhodes, "Discovery of immunopotentiatory drugs: current and future strategies", *Clin. Exp. Immunol.*, 2002, 130:363-369.

Rothenfusser et al., "Plasmacytoid Dentritic Cells: The Key to CpG", *Hum. Immunol.*, 2002, 63(12):1111-1119.

Sato et al., "A variety of microbial components induce tolerance to lipopolysaccharide by differentially affecting MyD88-dependent and -independent pathways", *Int. Immunol.*, 2002, 14(7):783-91.

Seela et al., "Synthese von 2-Amino-2,7-dihydro-7-(β-D-ribofuranosyl)-4H-pyrrolo[2,3-*d*]pyrimidin-4-on—7-Desazaguanosin—der Stammverbindung des Nucleosids Q", *Chem. Ber.*, 1981, 114 (10):3395-3402.

Skulnick et al., "Pyrimidinones. 3. N-Substituted 6-Phenylpyrimidinones and Pyrimidinediones with Diuretic/Hypotensive and Antiinflammatory Activity", *J. Med. Chem.*, 1986, 29:1499-1504.

Townsend, "The Synthesis of 2-Amiono-7-β-D-ribofuranosyl)pyrrolo[2,3,d)-pyrimidin-4-one (7-Deazaguanosine), a Nucleoside Q and Q Analog (1)", *J. Heterocyclic Chem*, Dec. 1976, 13:1363.

Ulevitch, "Therapeutics Targeting the Innate Immune System", *Nature*, 2004, 4:512-520.

Yamamoto et al., "Cutting Edge: A Novel Toll/IL-1 Receptor Domain-Containing Adapter That Preferentially Activates the IFN-β Promoter in the Toll-Like Receptor Signalinig[1]", *J. Immunol.*, 2002, 169(12):6668-72.

Yamamoto et al., "Essential role for TIRAP in activation of signaling cascade shared by TLR2 and TLR4", *Nature*, 2002, 420(6913):324-9.

"Oral Interferon-Like Molecule", *Updated on New Experimental Therapies*, http://archive.mail-list.com/pkids/msg03975.html, Jul. 21, 2004.

\* cited by examiner

ADMINISTRATION OF TLR7 LIGANDS AND PRODRUGS THEREOF FOR TREATMENT OF INFECTION BY HEPATITIS C VIRUS

This application claims the benefit of U.S. Provisional Application No. 60/500,339, filed Sep. 5, 2003, U.S. Provisional Application No. 60/518,996, filed Nov. 10, 2003, and U.S. Provisional Application No. 60/518,997, filed Nov. 10, 2003.

1. FIELD OF THE INVENTION

This invention relates to methods for treating or preventing hepatitis C virus infections in mammals using Toll-Like Receptor (TLR)$_7$ ligands and prodrugs thereof. More particularly, this invention relates to methods of orally administering a therapeutically effective amount of one or more prodrugs of TLR7 ligands for the treatment or prevention of hepatitis C viral infection. Oral administration of these TLR7 immunomodulating ligands and prodrugs thereof to a mammal provides therapeutically effective amounts and reduced undesirable side effects.

2. BACKGROUND OF THE INVENTION

Immunomodulation by small molecules can be achieved by identifying compounds that bind and activate Toll-Like Receptors (TLRs). TLRs play an important role in innate immune responses in mammals and are often the first line of defense against pathogens such as bacteria and viruses. The various TLRs vary in their abundance in different mammalian cell types and also vary regarding the molecular structures that bind the TLR and activate signaling pathways. These signaling pathways lead to the range of responses associates with innate immunity.

TLRs detect PAMPs (pathogen-associated molecular patterns) and stimulate immune cells via the MyD88-dependent interleukin 1 receptor (IL-1R)-TLR signaling pathway, which leads to activation of the transcription factor NF-κB2. Ten functional family members of TLRs (TLR1 to TLR10) have been identified in humans. Akira S. et al., *Nature Immunol.*, 2, 675-680 (2001). TLR2, TLR4, and TLR5 are crucial for the recognition of peptidoglycan, lipopolysacharide, and flagellin. Hayashi, F. et al., *Nature*, 410, 1099-1103 (2001). TLR6 associates with TLR2 and recognizes lipoproteins from mycoplasma. Ozinsky, A., et al., *Proc. Natl. Acad. Sci USA.*, 97, 13766-13771 (2000). TLR9 detects bacterial DNA containing unmethylated CpG motifs and TLR3 activates immune cells in response to double-stranded RNA. Hemmi, H. et al., Nature, 408, 740-745 (2000).

A number of compounds, including guanosine analogs, substituted pyrimidines, and imidazoquinolines have been reported as ligands for TLR7. See, e.g., Hemmi et al., *Nature Immunol.*, 3, 196-200 (2002) (imiquimod and R-848 (resiquimod)); Jurk et al., *Nat. Immunol.*, 3, 499 (2002) (R-848); and Lee et al., *Proc. Natl. Acad. Sci USA*, 100, 6646-6651 (2003) (wherein guanosine analogs loxoribine, 7-thia-8-oxoguanosine (isatoribine), and 7-deazaguanosine, and the imidazoquinolines imiquimod and R-848 (resiquimod) selectively activate TLR7).

Prior to being linked as potential TLR7 ligands, guanosine analogs and other D- and L-purine nucleosides have been the subject of considerable research the past two decades. See, e.g., Reitz et al., *J. Med. Chem.*, 37, 3561-78 (1994); Michael et al., *J. Med. Chem.*, 36, 3431-36 (1993) (immunomodulatory guanosine analogs having substituents at the 7-and/or 8-positions); U.S. Pat. No. 5,821,236 to Krenitsky et al. (disclosing 6-alkoxy derivatives of arabinofuranosyl purine derivatives that are useful for tumor therapy); U.S. Pat. No. 5,041,426 to Robins et al. (certain pyrimido[4,5-d]pyrimine nucleosides are disclosed in as being effective in treatment against L1210 in BDF1 mice); Revankar et al., *J. Med. Chem.*, 27, 1489-96 (1984) (3-Deazaguanine nucleosides and nucleotides demonstrating significant broad spectrum antiviral activity against certain DNA and RNA viruses);

A number of compounds known to be immunostimulants have recently been identified in the literature as TLR7 ligands, see, e.g., Heil et al., *Eur. J. Immunol.*, 33(11), 2987-97 (2003), Lore et al., *J. Immunol.*, 171(8), 4320-8 (2003), Nagase et al., *J. Immunol.*, 171(8), 3977-82 (2003), Mohty et al., *J. Immunol.*, 171(7), 3385-93 (2003), Pinhal-Enfield, et al., *Am. J. Pathol.*, 163(2), 711-21 (2003), Doxsee et al, *J. Immunol.*, 171(3), 1156-63 (2003), Bottcher et al., *Neurosci. Lett.*, 344(1), 17-20 (2003), Kaisho et al., *Curr. Mol. Med.*, 3(4), 373-85 (2003), Okada et al., *Eur. J. Immunol.*, 33(4), 1012-9 (2003), Edwards et al., *Eur. J. Immunol.*, 33(4), 827-33 (2003), Akira et al., *Immunol. Lett.*, 85(2), 85-95 (2003), Ito et al., *Hum. Immunol.*, 63(12), 1120-5 (2002), Rothenfusser et al., *Hum. Immunol.*, 63(12), 1111-9 (2002), Yamamoto et al., *J. Immunol.*, 169(12), 6668-72 (2002), Gibson et al., *Cell Immunol.*, 218(1-2), 74-86 (2002), Horng et al., *Nature*, 420 (6913), 329-33 (2002), Yamamoto et al., *Nature*, 420(6913), 324-9 (2002), Applequist et al., *Int. Immunol.*, 14(9), 1065-74 (2002), Sato et al., *Int. Immunol.*, 14(7), 783-91 (2002); Jurk et al., *Nat. Immunol.*, 3(6), 499 (2002); Hornung et al., *J. Immunol.*, 168(9), 4531-7 (2002), Hemmi et al., *Nat. Immunol.*, 3(2), 196-200 (2002); Bruno et al., *Eur. J. Immunol.*, 31(11), 3403-12 (2001); Jarrossay et al., *Eur. J. Immunol.*, 31(11), 3388-93 (2001); Miettinen et al., *Genes Immun.*, 2(6), 349-55 (2001), Chuang et al., *Eur. Cytokine Netw.*, 11(3), 372-8 (2000), and Du et al., *Eur. Cytokine Netw.*, 11(3), 362-71 (2000).

These TLR7 ligands are known to stimulate immune responses in vitro and in animal species, and this has led to testing of the uses of these compounds for several therapeutic uses, including antiviral and cancer therapies. These compounds have been characterized as analogs or derivatives of a) guanosine, b) imidazoquinoline, and c) pyrimidine. See Akira, *Current Opinion*, 15, 5-11 (2003). One member (imiquimod) of the imidazoquinoline chemical class has been found effective for treating topical genital infections by papilloma virus. A second member of the imidazoquinoline class, resiquimod, has been tested for the treatment of HCV, but this compound failed to show anti-HCV effect at tolerated oral doses. Pockros et al., *Gastroenterology*, 124 (Suppl 1), A-766 (2003).

Thus, while there has been some limited use of TLR7 ligands for the treatment of immunological disease and viral infections; see, e.g., U.S. Pat. Nos. 5,041,426 and 4,880,784 to Robins et al. (3-β-D-ribofuranosylthiazolo[4,5-d]pyrimidines demonstrating significant immunoactivity, including murine spleen cell proliferation and in vivo activity against Semliki Forest virus); United States Patent Application Publication No. US 2003/0199461 and WO 03/045968 to Averett et al. (3-β-D-ribofuranosylthiazolo[4,5-d]pyrimidine nucleosides demonstrating activity against acute and chronic infections of both RNA and DNA viruses); to date ligands have proved ineffective for the treatment or prevention of Hepatitis C virus.

It is also known that the oral administration of many purine nucleoside analogs are subject to difficulties arising from poor absorption, poor solubility, or degradation in the digestive tract as a result of acidic or alkaline conditions or the action of enzymes, and/or combinations of these phenomena.

Thus there remains a need for purine nucleoside analogs with improved oral availability and administration that are used to modulate aspects of the immune system.

Moreover, immunomodulatory nucleosides have relatively poor oral tolerability when compared to that of the intravenous route. Also, the gastrointestinal tract presents a particular tolerability barrier to immunologic agents by virtue of the large amount of immune tissue associated with the intestinal wall (i.e., gut). Although this is an important biologic mechanism for preventing invasion of the body by gut flora, the immune tissue also may become preferentially affected after oral administration of immunomodulatory compounds because of the high local concentrations of the administered compound in the gut. This leads to undesirable side effects, for example in the case of immune activating agents there is observed gastroenteritis and localized hemorrhagic effects.

A solution to the problem of effective oral delivery of immunomodulators is not evident in the literature. Available evidence indicates that systemic levels of administered drugs in this class have been limited by gastrointestinal toxicities arising after low oral doses. Therefore there remains a need for immunomodulating TLR7 ligands that have improved oral availability and reduced gastrointestinal irritancy.

3. SUMMARY OF THE INVENTION

3.1 TLR7 Ligands

This invention encompasses novel methods for the treatment or prevention of hepatitis C viral infection, and novel pharmaceutical compositions which utilize TLR7 ligands or pharmaceutically acceptable salts, hydrates, metabolites or stereoisomers thereof.

In one embodiment, the invention encompasses a method of treating or preventing a hepatitis C virus infection in a patient in need thereof comprising administering to the patient a therapeutically or prophylactically effective amount of a TLR7 ligand or a pharmaceutically acceptable salt, hydrate, metabolite or stereoisomer thereof or a pharmaceutically acceptable salt or hydrate of said stereoisomer.

In another embodiment, the invention encompasses a method of treating or preventing a hepatitis C virus infection in a patient in need thereof comprising administering to the patient a therapeutically or prophylactically effective amount of a TLR7 ligand selected from analogs and derivatives of a) guanosine b) imidazoquinoline c) adenine, and d) pyrimidine.

In another embodiment, the invention encompasses a method of treating or preventing a hepatitis C virus infection in a patient in need thereof comprising administering to the patient a therapeutically or prophylactically effective amount of a TLR7 ligand selected from

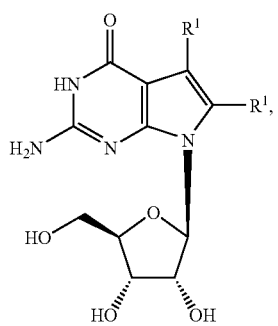

Ia

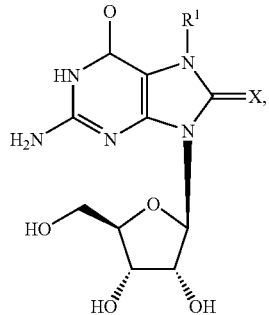

Ib

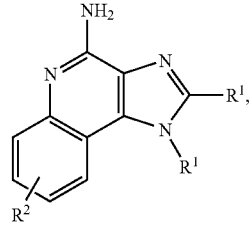

Ic

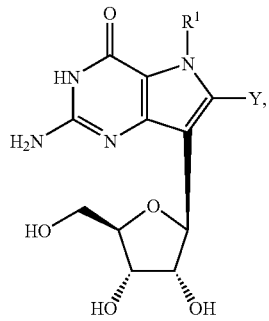

Id

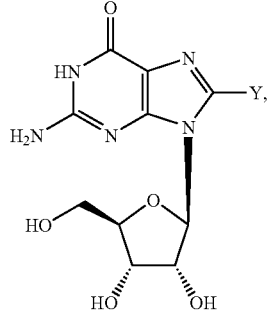

Ie

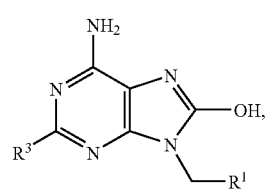

If

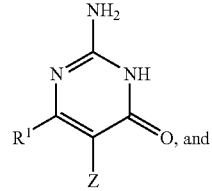

Ig

O, and

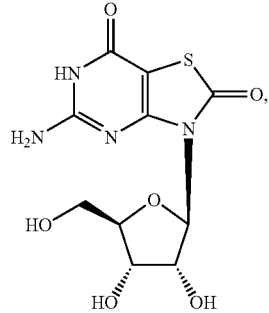

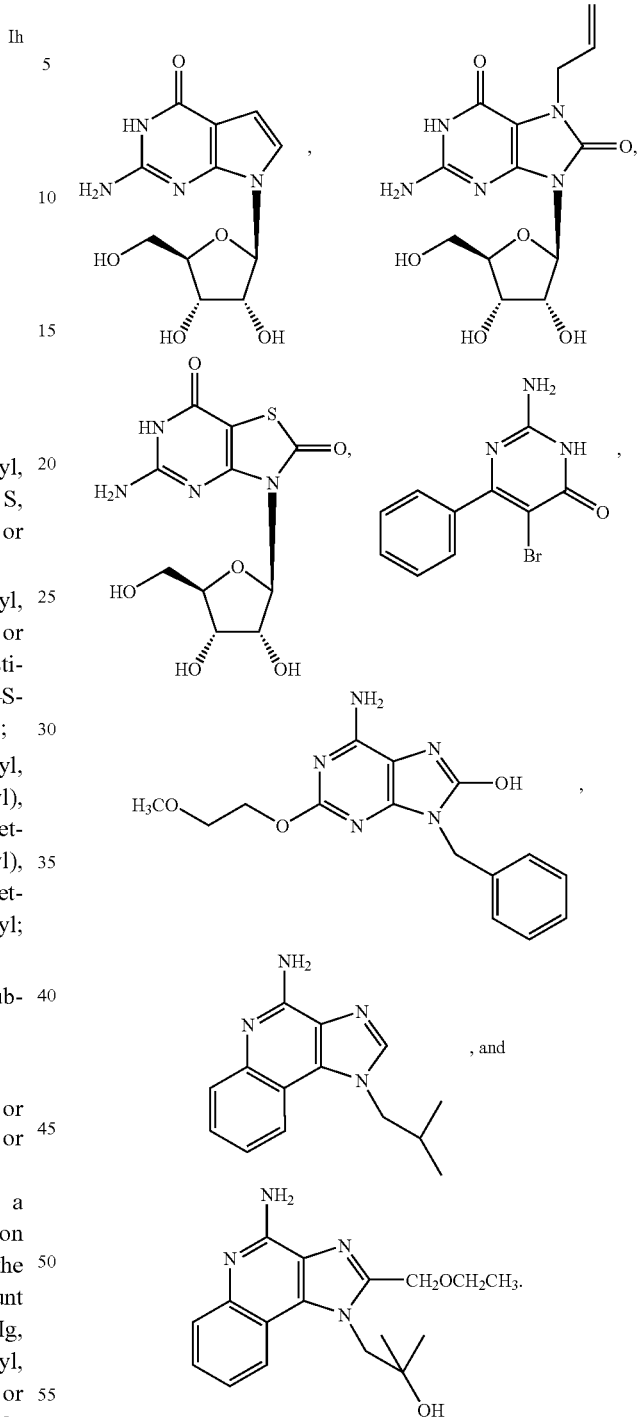

wherein:
each $R^1$ is H, or a substituted or unsubstituted alkyl, alkenyl, or alkynyl, which may be interrupted by one or more O, S, or N heteroatoms, or a substituted or unsubstituted aryl or heteroaryl;

$R^2$ is H, OH, SH, halo, or a substituted or unsubstituted alkyl, alkenyl, or alkynyl, which may be interrupted by one or more O, S, or N heteroatoms, or a substituted or unsubstituted —O-(alkyl), —O-(aryl), —O-(heteroaryl), —S-(alkyl), —S-(aryl), —S-(heteroaryl), aryl, or heteroaryl;

$R^3$ is H, OH, or SH, or a substituted or unsubstituted alkyl, alkenyl, alkynyl, aryl, heteroaryl, —O-(alkyl), —O-(aryl), —O-(heteroaryl), —S-(alkyl), —S-(aryl), —S-(heteroaryl), —NH(alkyl), —NH(aryl), —NH(heteroaryl), —NH($R^4$)(alkyl), —NH($R^4$)(aryl), or —NH($R^4$)(heteroaryl), wherein $R^4$ is a substituted or unsubstituted alkyl;

X is O or S;

Y is H, halo, OH, $OR^4$, SH, $SR^4$, or a substituted or unsubstituted alkyl or aryl;

Z is H, halo, OH, $OR^4$, SH, or $SR^4$;

or a pharmaceutically acceptable salt, hydrate, metabolite or stereoisomer thereof or a pharmaceutically acceptable salt or hydrate of said stereoisomer.

In another embodiment, the invention encompasses a method of treating or preventing a hepatitis C virus infection in a patient in need thereof comprising administering to the patient a therapeutically or prophylactically effective amount of a TLR7 ligand selected from Formula Ia, Ib, Ic, Id, Ie, If, Ig, and Ih, wherein $R^1$ is H or a substituted or unsubstituted alkyl, alkenyl, or alkynyl; $R^2$ is H, OH, halo, or a substituted or unsubstituted alkyl, alkenyl, or alkynyl, or —$CH_2$—O-(alkyl); $R^3$ is H, OH, or SH, or a substituted or unsubstituted —O-(alkyl), —S-(alkyl), or —NH(alkyl); X is O or S; Y is H, halo, OH, $OR^4$, SH, or $SR^4$; and Z is H, halo, OH, $OR^4$, SH, or $SR^4$.

In another embodiment, the invention encompasses a method of treating or preventing a hepatitis C virus infection in a patient in need thereof comprising administering to the patient a therapeutically or prophylactically effective amount of a TLR7 ligand selected from or a pharmaceutically acceptable salt, hydrate, metabolite or stereoisomer thereof.

In one aspect, the invention encompasses a method for treating or preventing hepatitis C virus infection in a mammal in need thereof, preferably in a human in need thereof.

In an alternative embodiment, the invention encompasses a method for treating or preventing hepatitis C virus infection in a patient in need thereof, comprising administering to the patient a therapeutically or prophylactically effective amount of a TLR7 ligand and a pharmaceutically acceptable excipient, carrier, or vehicle.

In an alternative embodiment, the invention encompasses a method for treating or preventing hepatitis C virus infection in a patient in need thereof, comprising administering to the patient a therapeutically or prophylactically effective amount of a TLR7 ligand orally, mucosally, topically or transdermally.

In a preferred embodiment, the invention encompasses a method for treating or preventing hepatitis C virus infection in a patient in need thereof, comprising administering to the patient a therapeutically or prophylactically effective amount of a TLR7 ligand parenterally.

In a separate embodiment, the invention encompasses a method for treating or preventing hepatitis C virus infection in a patient in need thereof, comprising administering to the patient a therapeutically or prophylactically effective amount of a TLR7 ligand and an additional therapeutic agent, preferably an additional antiviral or immunomodulatory agent.

The invention also encompasses pharmaceutical compositions suitable for parenteral administration to a patient comprising a therapeutically or pharmaceutically acceptable amount of a TLR7 ligand of the invention in a sterile form; pharmaceutical compositions suitable for oral administration to a patient comprising a therapeutically or pharmaceutically acceptable amount of a TLR7 ligand of the invention, wherein such compositions are formulated to reduce exposure of the subepithelial immune anatomy to the TLR7 ligand while improving systemic absorption of the TLR7 ligand; pharmaceutical compositions suitable for mucosal administration to a patient comprising a therapeutically or pharmaceutically acceptable amount of a TLR7 ligand of the invention, wherein such compositions are formulated to reduce exposure of the subepithelial immune anatomy to the TLR7 ligand while improving systemic absorption of the TLR7 ligand; and pharmaceutical compositions suitable for topical administration to a patient comprising a therapeutically or pharmaceutically acceptable amount of a TLR7 ligand of the invention, wherein such compositions are formulated to reduce exposure of the subepithelial immune anatomy to the TLR7 ligand while improving systemic absorption of the TLR7 ligand. Depending on the specific tissue to be treated, additional components, such as penetration enhancers, may be used prior to, in conjunction with, or subsequent to treatment with active ingredients of the invention. In a preferred embodiment, each of these compositions is in single unit dosage form and comprising an amount of active ingredient sufficient to treat or prevent human infection by hepatitis C virus.

In a specific embodiment, the invention encompasses a pharmaceutical composition comprising a TLR7 ligand selected from analogs and derivatives of a) guanosine, b) imidazoquinoline, c) adenine, and d) pyrimidine.

In another specific embodiment, the invention encompasses a pharmaceutical composition comprising a TLR7 ligand selected from Formulas Ia, Ib, Ic, Id, Ie, If, Ig, and Ih, or a pharmaceutically acceptable salt, hydrate, metabolite or stereoisomer thereof or a pharmaceutically acceptable salt or hydrate of said stereoisomer.

3.2 TLR7 Ligand Prodrugs

This invention also encompasses novel methods for the treatment or prevention of hepatitis C viral infection, and novel pharmaceutical compositions which utilize TLR7 ligand prodrugs or pharmaceutically acceptable salts, hydrates, metabolites or stereoisomers thereof.

This invention also encompasses novel methods of treating diseases responsive to immuno therapy with immunologic agents, comprising orally administering a TLR7 ligand prodrug to a patient in need of immuno therapy, wherein the TLR7 prodrug achieves a therapeutically effective plasma concentration of the TLR7 ligand in the patient.

In one embodiment, the invention encompasses a method of treating a hepatitis C virus infection in a patient comprising orally administering to the patient a TLR7 ligand prodrug or a pharmaceutically acceptable salt, hydrate, or stereoisomer thereof, wherein the oral administration of the TLR7 ligand prodrug achieves a therapeutically effective plasma concentration of the TLR7 ligand while reducing undesirable side effects associated with TLR7 ligands. In a preferred embodiment, the TLR7 ligand prodrug is a masked TLR7 ligand prodrug.

In another embodiment, the invention also encompasses a method of treating diseases responsive to immuno therapy while reducing undesirable side effects associated with immunologic agents, comprising orally administering a TLR7 ligand prodrug to a patient in need of immuno therapy, wherein the TLR7 prodrug achieves a therapeutically effective plasma concentration of the TLR7 ligand in the patient. In a preferred embodiment, the TLR7 ligand prodrug is a masked TLR7 ligand prodrug.

In another embodiment, the oral administration of the TLR7 ligand prodrug improves the in vivo bioavailability of the TLR7 ligand. In a preferred embodiment, the oral administration of the TLR7 ligand prodrug achieves an in vivo effective plasma concentration of the TLR7 ligand that is 10% to 500% of the effective in vivo exposure obtained upon oral administration of the TLR7 ligand alone. In another preferred embodiment, the oral administration of the masked TLR7 ligand prodrug achieves an in vivo effective plasma concentration of the TLR7 ligand that is 50% to 200% of the effective in vivo exposure obtained upon oral administration of the TLR7 ligand alone.

In another embodiment, the oral administration of the TLR7 ligand prodrug reduces adverse side effects. In a preferred embodiment, the side effect comprises gastrointestinal irritancy, wherein gastrointestinal irritancy comprises hemorrhage, lesions, and emesis.

In another embodiment, the TLR7 ligand prodrug improves oral availability by at least 25% and reduces gastrointestinal irritancy by at least 50% in a patient relative to the oral administration of the TLR7 ligand alone. In another embodiment, the TLR7 ligand prodrug improves oral availability by at least 50% and reduces gastrointestinal irritancy by such that other toxicities become limiting in a patient relative to the oral administration of the TLR7 ligand alone.

In a preferred embodiment, the TLR7 ligand prodrug achieves a therapeutically effective plasma concentration that is 25% to 200% of the effective in vivo concentration of the TLR7 ligand in a patient after oral administration, with minimal gastrointestinal irritancy.

In one embodiment, the methods of the invention encompass administering to a patient in need thereof a therapeutically or prophylactically effective amount of a prodrug of a TLR7 ligand selected from analogs and derivatives of a) guanosine, b) imidazoquinoline, c) adenine, and d) pyrimidine.

In another embodiment, the methods of the invention encompass administering to a patient in need thereof a therapeutically or prophylactically effective amount of a prodrug of a TLR7 ligand selected from analogs and derivatives of a) guanosine, b) imidazoquinoline, c) adenine, and d) pyrimidine, wherein the prodrug is an (a) amide, carbamate, or amidine moiety after conversion of a TLR7 ligand amine substituent, (b) ester, carbonate, carbamate, ether, imidate, acetal, aminal, or ketal moiety after conversion of a TLR7 ligand alcohol substituent, (c) acetal or ketal moiety after conversion of a TLR7 ligand keto substituent, (d) imidate moiety after conversion of a TLR7 ligand carbonyl of an amido substituent, (e) deoxygenated moiety after conversion of a TLR7 ligand oxo substituent of pyrimidine or guanosine, or (f) amine.

In another embodiment, the methods of the invention encompass administering to a patient in need thereof a therapeutically or prophylactically effective amount of a prodrug of a TLR7 ligand selected from

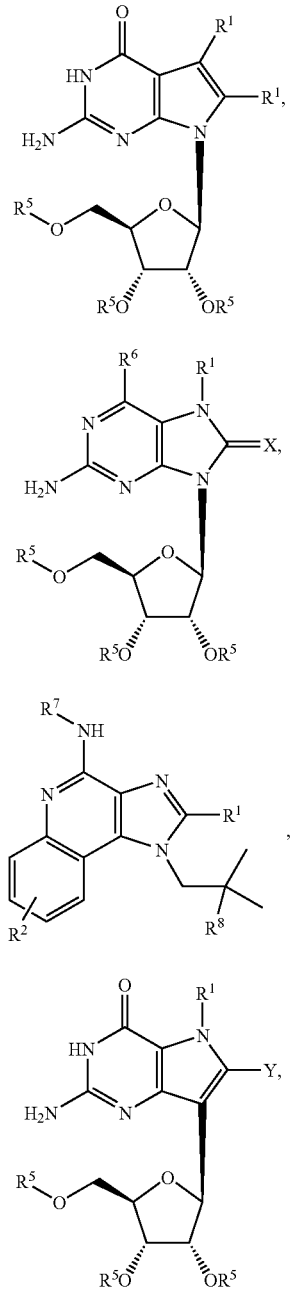

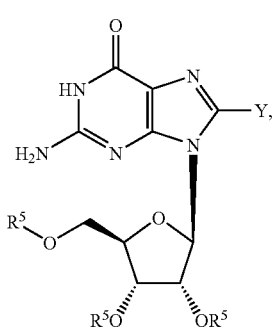

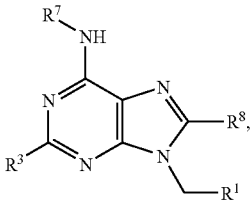

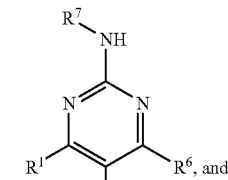

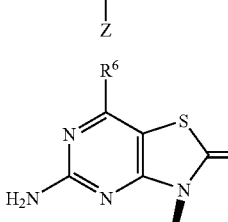

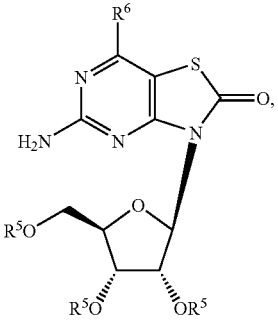

wherein:

each $R^1$ is H, or a substituted or unsubstituted alkyl, alkenyl, or alkynyl, which may be interrupted by one or more O, S, or N heteroatoms, or a substituted or unsubstituted aryl or heteroaryl;

$R^2$ is H, OH, SH, halo, or a substituted or unsubstituted alkyl, alkenyl, or alkynyl, which may be interrupted by one or more O, S, or N heteroatoms, or a substituted or unsubstituted —O-(alkyl), —O-(aryl), —O-(heteroaryl), —S-(alkyl), —S-(aryl), —S-(heteroaryl), aryl, or heteroaryl;

$R^3$ is H, OH, or SH, or a substituted or unsubstituted alkyl, alkenyl, alkynyl, aryl, heteroaryl, —O-(alkyl), —O-(aryl), —O-(heteroaryl), —S-(alkyl), —S-(aryl), —S-(heteroaryl), —NH(alkyl), —NH(aryl), —NH(heteroaryl), —NH($R^4$)(alkyl), —NH($R^4$)(aryl), or —NH($R^4$)(heteroaryl);

$R^4$ is a substituted or unsubstituted alkyl;

$R^5$ is independently H, —C(O)($C_{1-18}$alkyl), or a racemic, L-, or D-amino acid group —C(O)CHNH$_2R^9$;

$R^6$ is H, $OR^{10}$, or $N(R^{11})_2$;

R[7] is independently H or a substituted or unsubstituted —C(O)(C$_{1-18}$alkyl) or —C(O)$_2$(C$_{1-18}$alkyl);

R[8] is H, —OH, —O-(alkyl), —OCO$_2$(C$_{1-18}$alkyl), —OC(O)(C$_{1-18}$alkyl), or a racemic, L-, or D-amino acid group —OC(O)CHNH$_2$R[1];

R[9] is H, or a substituted or unsubstituted alkyl, C(O)CH(C$_{1-6}$ alkyl)NH$_2$, or —C(O)CH(CH$_2$-aryl)NH$_2$;

R[10] is independently H, C$_{1-6}$ alkyl, C$_{3-7}$ alkenyl, C$_{3-7}$ alkynyl, —(CR[12]R[13])$_t$(C$_6$-C$_{10}$aryl), —(CR[12]R[13])$_t$(C$_3$-C$_{10}$ cycloalkyl), —(CR[12]R[13])$_t$(C$_4$-C$_{10}$ heterocyclic), —(CR[12]R[13])$_{t>1}$OH, —(CR[12]R[13])$_{t>0}$CO$_2$C$_{1-18}$ alkyl, and —(CR[12]R[13])$_{t>0}$N(R[14])CO$_2$C$_{1-18}$ alkyl, and SO$_2$(aryl), wherein t is an integer from 0 to 6 unless otherwise indicated, and wherein the alkyl, alkenyl, alkynyl, aryl, cycloalkyl, and heterocyclic moieties of the foregoing groups are optionally substituted with substituents independently selected from halo, cyano, nitro, trifluoromethyl, trifluoromethoxy, C$_1$-C$_6$ alkyl, C$_2$-C$_6$ alkenyl, C$_2$-C$_6$ alkynyl, hydroxy, C$_1$-C$_6$ alkoxy, —NH$_2$, —NH-alkyl, —N(alkyl)$_2$, —NH-aryl, —N(alkyl)(aryl), —N(aryl)$_2$, —NHCHO, —NHC(O)alkyl, —NHC(O)aryl, —N(alkyl)C(O)H, —N(alkyl)C(O)alkyl, —N(aryl)C(O)H, —N(aryl)C(O)alkyl, —NHCO$_2$alkyl, —N(alkyl)CO$_2$alkyl, —NHC(O)NH$_2$, —N(alkyl)C(O)NH$_2$, —NHC(O)NH-alkyl, —NHC(O)N(alkyl)$_2$, —N(alkyl)C(O)NH-alkyl, —N(alkyl)C(O)N(alkyl)$_2$, —NHSO$_2$-alkyl, —N(alkyl)SO$_2$-alkyl, —C(O)alkyl, —C(O)aryl, —OC(O)alkyl, —OC(O)aryl, —CO$_2$-alkyl, —CO$_2$-aryl, —CO$_2$H, —C(O)NH$_2$, —C(O)NH-alkyl, —C(O)N(alkyl)$_2$, —C(O)NH-aryl, —C(O)N(aryl)$_2$, —C(O)N(alkyl)(aryl), —S(O)alkyl, —S(O)aryl, —SO$_2$alkyl, —SO$_2$aryl, —SO$_2$NH$_2$, —SO$_2$NH-alkyl, and —SO$_2$N(alkyl)$_2$;

R[11] is independently H, C$_{1-6}$ alkyl, C$_3$-C$_{10}$ cycloalkyl, or together with nitrogen forms a 5- or 6-membered heterocyclic ring;

R[12] and R[13] are independently H, C$_{1-6}$ alkyl, C$_{2-6}$ alkenyl, or C$_{2-6}$ alkynyl;

R[14] is H, C$_{1-6}$ alkyl, or —CH$_2$-aryl;

X is O or S;

Y is H, halo, OH, OR[4], SH, SR[4], or a substituted or unsubstituted alkyl or aryl; and Z is H, halo, OH, OR[4], SH, or SR[4];

or a pharmaceutically acceptable salt, hydrate, metabolite or stereoisomer thereof or a pharmaceutically acceptable salt or hydrate of said stereoisomer.

In another embodiment, the invention encompasses a method of treating or preventing a hepatitis C virus infection in a patient in need thereof comprising administering to the patient a therapeutically or prophylactically effective amount of a TLR7 ligand selected from Formula Ia, IIb, IIc, IId, IIe, IIf, IIg, and IIh, wherein R[1] is H or a substituted or unsubstituted alkyl, alkenyl, or alkynyl; R[2] is H, OH, halo, or a substituted or unsubstituted alkyl, alkenyl, or alkynyl, or —CH$_2$—O-(alkyl); R[3] is H, OH, or SH, or a substituted or unsubstituted —O-(alkyl), —S-(alkyl), or —NH(alkyl); R[5] is independently H, —C(O)(C$_1$-I$_8$alkyl), or a racemic, L-, or D-amino acid group —C(O)CHNH$_2$R[9], wherein R[9] is an unsubstituted alkyl; R[6] is H or OR[10], wherein R[10] is independently C$_{1-6}$ alkyl, C$_{3-7}$ alkenyl, C$_{3-7}$ alkynyl, —(CR[12]R[13])$_t$(C$_6$-C$_{10}$ aryl), —(CR[12]R[13])$_t$(C$_4$-C$_{10}$ heterocyclic), and —(CR[12]R[13])$_{t>0}$N(R[14])CO$_2$C$_{1-18}$ alkyl, wherein t is an integer from 0 to 4 unless otherwise indicated, and wherein the alkyl, alkenyl, aryl, and heterocyclic moieties of the foregoing groups are optionally substituted with 1 to 3 substituents independently selected from halo, cyano, nitro, trifluoromethyl, trifluoromethoxy, C$_1$-C$_6$ alkyl, C$_2$-C$_6$ alkenyl, C$_2$-C$_6$ alkynyl, hydroxy, C$_1$-C$_6$ alkoxy, —CO$_2$-alkyl, —CO$_2$-aryl, —OC(O)alkyl, and —OC(O)aryl, and wherein R[12] and R[13] are independently H, C$_{1-6}$ alkyl, or C$_{2-6}$ alkenyl; and R[14] is H, —CH$_3$, or —CH$_2$CH$_3$; R[7] is independently H or a substituted or unsubstituted —C(O)(C$_{1-18}$alkyl) or —C(O)$_2$(C$_{1-18}$alkyl); R[8] is H, OH, —O-(alkyl), OCO$_2$(C$_{1-18}$alkyl), or a racemic, L-, or D-amino acid group —OC(O)CHNH$_2$R[1]; X is O or S; Y is H, halo, OH, OR[4], SH, or SR[4]; and Z is H, halo, OH, OR[4], SH, or SR4.

In specific embodiment, the invention encompasses a method of treating or preventing a hepatitis C virus infection in a patient in need thereof comprising administering to the patient a therapeutically or prophylactically effective amount of a prodrug of a TLR7 ligand selected from

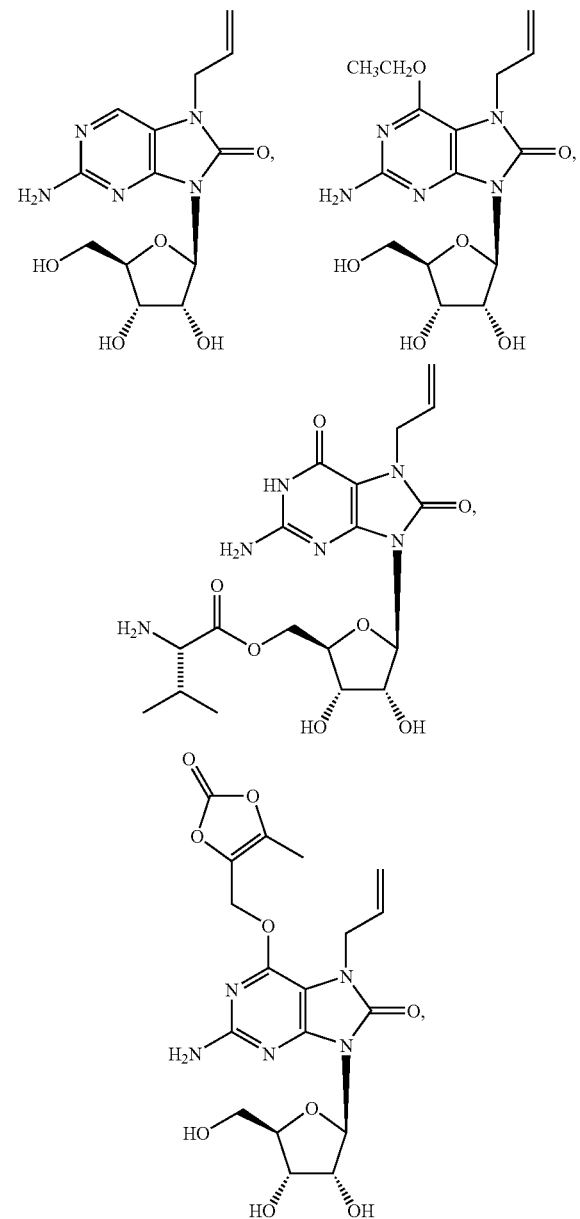

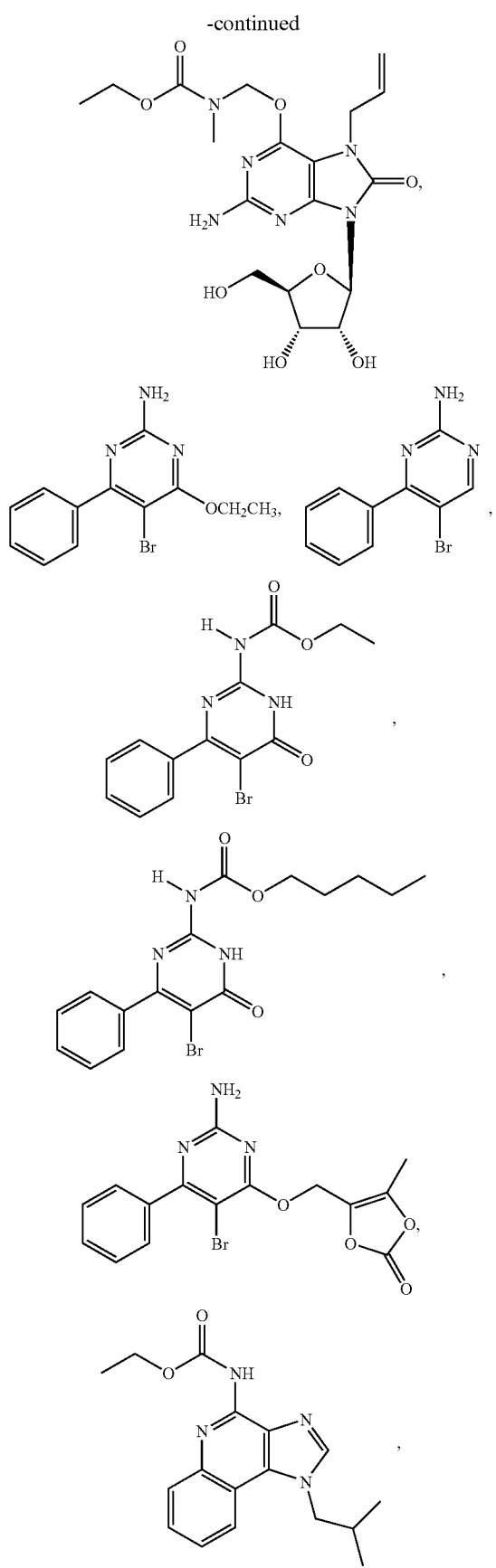
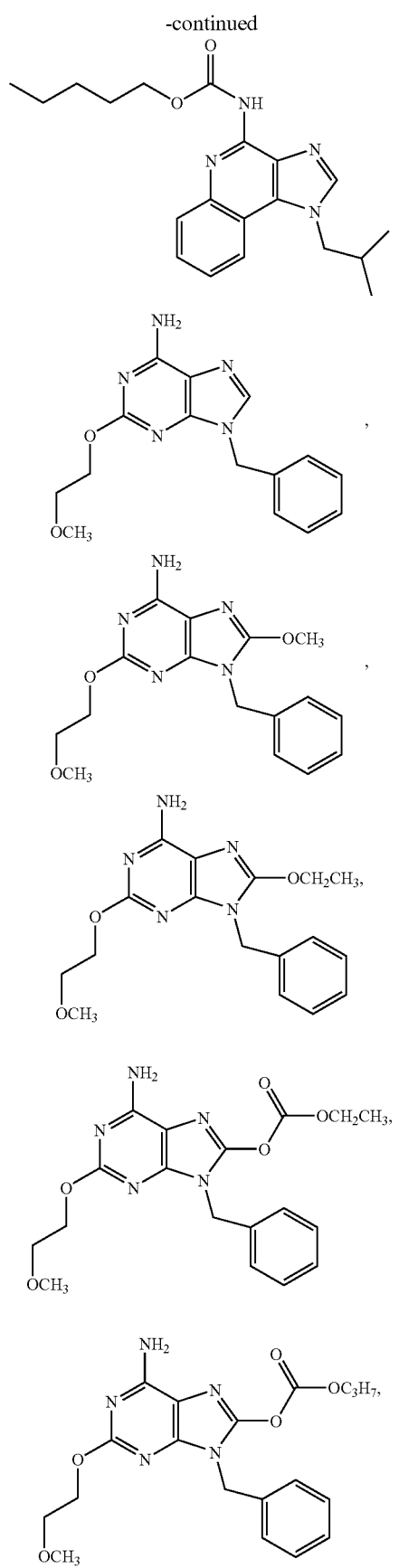

-continued
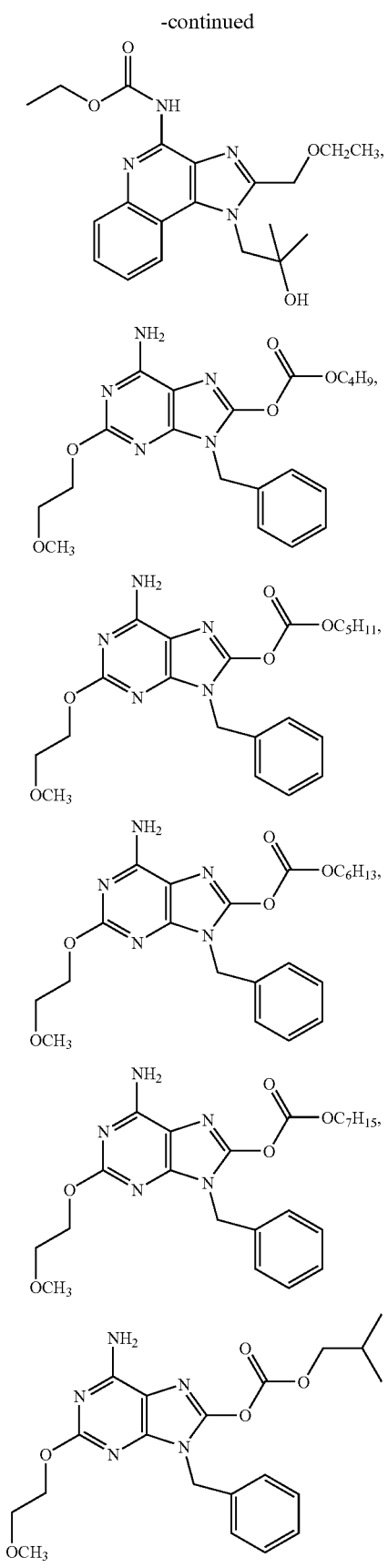
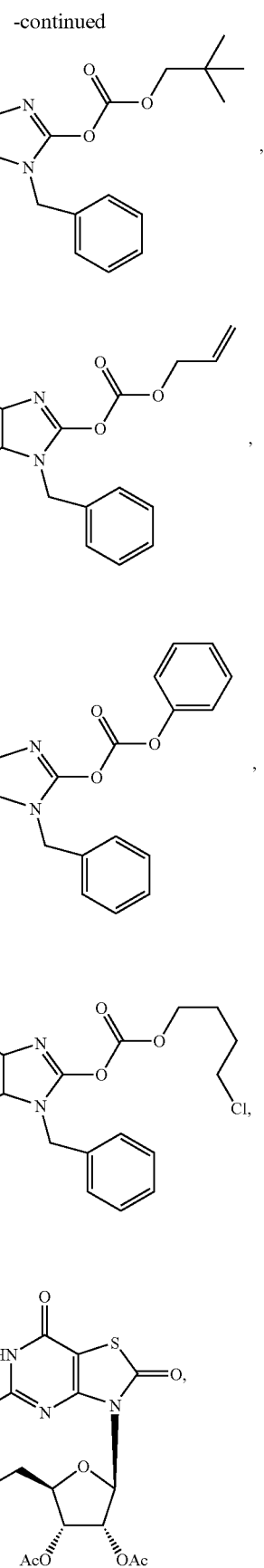

-continued
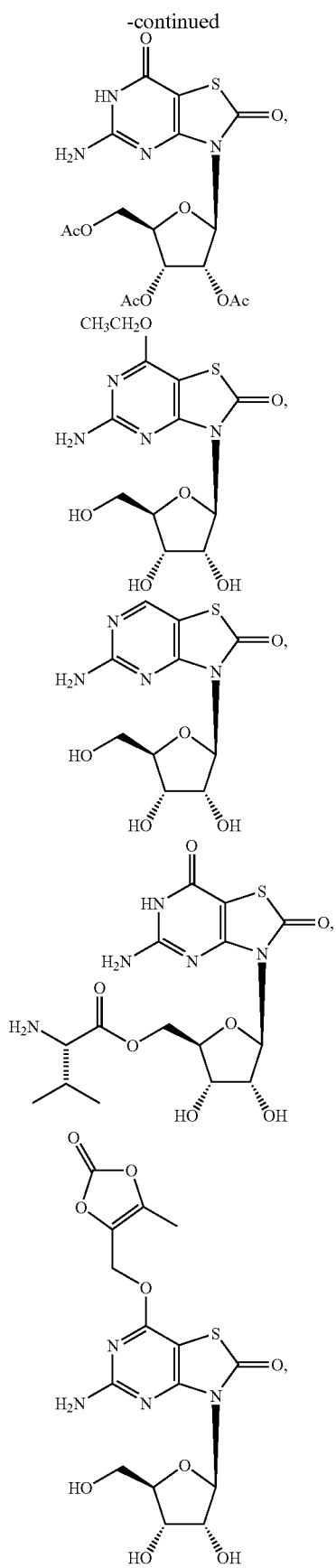
-continued
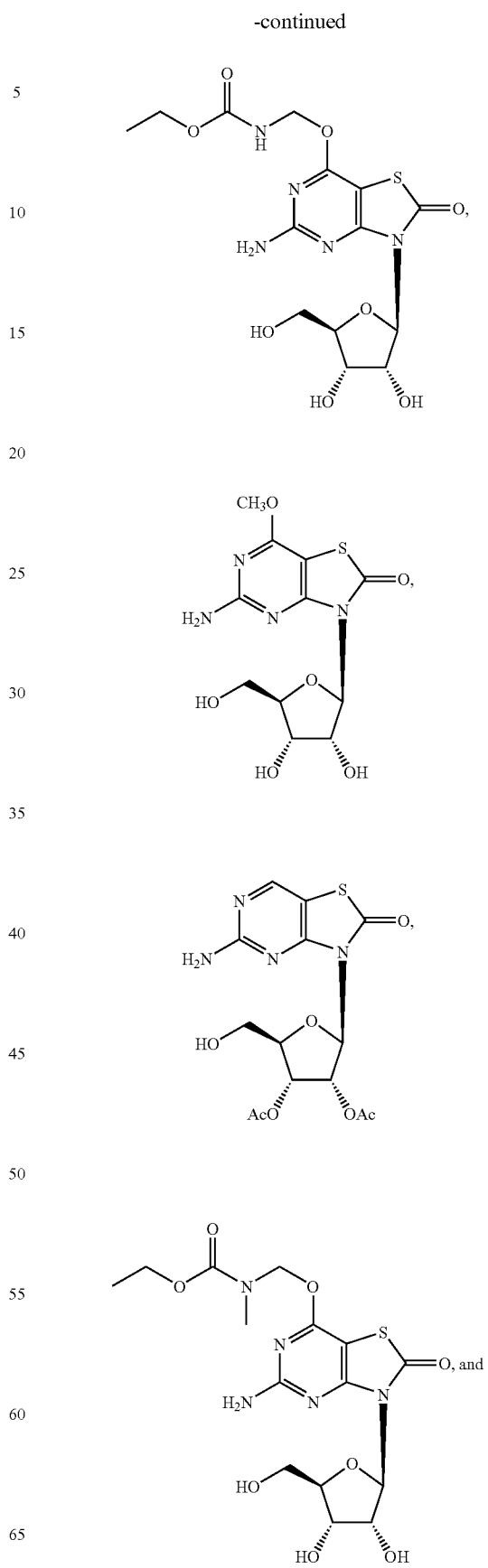

-continued

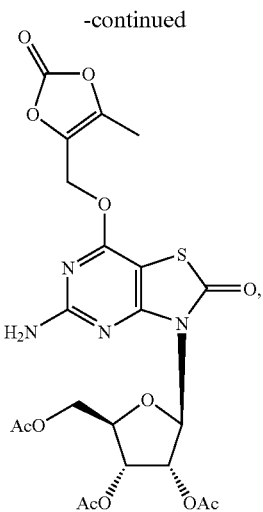

or a pharmaceutically acceptable salt, hydrate, or stereoisomer thereof or a pharmaceutically acceptable salt or hydrate of said stereoisomer.

In another preferred embodiment of the invention, the TLR7 ligand prodrug is an amino acid ester prodrug of the TLR7 ligand. In another preferred embodiment, the amino acid ester prodrug of the TLR7 ligand is a valyl ester.

In one embodiment of the invention, $R^5$ is not a racemic, L-, or D-amino acid group —C(O)CHNH$_2$R$^9$. In another embodiment, $R^5$ is not a racemic, L-, or D-amino acid group —C(O)CHNH$_2$R$^9$ when the TLR7 ligand prodrug is selected from a compound of Formula IIh.

In another alternative embodiment, the invention encompasses a method for treating or preventing hepatitis C virus infection in a patient in need thereof, comprising administering to the patient a therapeutically or prophylactically effective amount of a prodrug of a TLR7 ligand and a pharmaceutically acceptable excipient, carrier, or vehicle.

In a separate embodiment, the invention encompasses a method for treating or preventing hepatitis C virus infection in a patient in need thereof, comprising administering to the patient a therapeutically or prophylactically effective amount of a prodrug of a TLR7 ligand and an additional therapeutic agent, preferably an additional antiviral or immunomodulatory agent.

The invention also encompasses pharmaceutical compositions suitable for parenteral administration to a patient comprising a therapeutically or pharmaceutically acceptable amount a prodrug of a TLR7 ligand of the invention in a sterile form; pharmaceutical compositions suitable for parenteral administration to a patient comprising a therapeutically or pharmaceutically acceptable amount of a prodrug of a TLR7 ligand of the invention; pharmaceutical compositions suitable for mucosal administration to a patient comprising a therapeutically or pharmaceutically acceptable amount of a prodrug of a TLR7 ligand of the invention; and pharmaceutical compositions suitable for topical administration to a patient comprising a therapeutically or pharmaceutically acceptable amount of a prodrug of a TLR7 ligand of the invention. Depending on the specific tissue to be treated, additional components, such as penetration enhancers, may be used prior to, in conjunction with, or subsequent to treatment with active ingredients of the invention. In a preferred embodiment, each of these compositions is in single unit dosage form and comprising an amount of active ingredient sufficient to treat or prevent human infection by hepatitis C virus.

In a specific embodiment, the invention encompasses a pharmaceutical composition comprising a prodrug of a TLR7 ligand selected from Formula Ia, IIb, IIc, IId, IIe, IIf, IIg, and IIh, or a pharmaceutically acceptable salt, hydrate or stereoisomer thereof or a pharmaceutically acceptable salt or hydrate of said stereoisomer.

In another embodiment of the invention, and depending on the specific tissue to be treated, additional components including, but not limited to penetration enhancers, molecules which target the area of the infection and molecules which reduce the in vivo toxicity of the prodrug of a TLR7 ligand may be used prior to, in conjunction with, or subsequent to treatment with one or more prodrugs of TLR7 ligands of the invention.

The TLR7 ligand prodrugs are useful as immune system enhancers and have certain immune system properties including modulation, mitogenicity, augmentation, and/or potentiation or they are intermediates for compounds that have these properties. The compounds are expected to express effects after administration to a mammal on at least one of the cell populations characterized as the natural killer cells, macrophages, dendritic cells, and lymphocyte cells of the immune system of a host. Because of these properties they are useful as an anti-infective including, but not limited to antiviral agents, and as antitumor agents or as intermediates for the same. They can be used to treat an affected host by serving as the active ingredients of suitable pharmaceutical compositions.

In one aspect of the invention, TLR7 ligand prodrugs are utilized to treat the full range of viral diseases in mammals by administering to the mammal a therapeutically effective amount of the compounds. Viral diseases contemplated to be treated with TLR7 ligand prodrugs include acute and chronic infections caused by both RNA and DNA viruses. Without limiting in any way the range of viral infections that may be treated, TLR7 ligand prodrugs are particularly useful in the treatment of infections caused by adenovirus, cytomegalovirus, hepatitis A virus (HAV), hepatitis B virus (HBV), flaviviruses including Yellow Fever virus, hepacivirus including hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, pestivirus, poliovirus, poxvirus (including smallpox and monkeypox virus), rhinovirus, coronovirus, respiratory syncytial virus (RSV), multiple families of viruses that cause hemorrhagic fevers, including the Arenaviruses (LCM, Junin virus, Machupo virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, and tickborne viruses such as Crimean-Congo Hemorrhagic fever virus.

In another aspect of the invention, TLR7 ligand prodrugs are utilized to treat bacterial, fungal, and protozoal infections in mammals by administering to the mammal a therapeutically effective amount of the prodrugs. The full range of pathogenic microorganisms is contemplated to be treatable by the TLR7 ligand prodrugs of the present invention, including without limitation those organisms that are resistant to antibiotics. The ability of TLR7 ligand prodrugs to activate multiple components of the immune system bypasses resistance mechanisms commonly found to reduce susceptibility to antibiotics, and thus treatment of infections in a mammal caused by such resistant microorganisms by TLR7 ligand prodrugs is a particular utility of the present invention.

In another aspect of the invention, TLR7 ligand prodrugs are utilized to treat tumors in mammals by administering to the mammal a therapeutically effective amount of the prodrugs. Tumors or cancers contemplated to be treated include both those arising from aberrations in normal cellular processes as well as those caused by virus, and the effect may involve inhibiting the spread of cancerous cells, accelerating the killing of cancerous cells, inhibiting transformation of virus-infected cells to a neoplastic state, inhibiting the spread of viruses from transformed cells to other normal cells, and/or arresting the growth of virus-transformed cells. The prodrugs of TLR7 ligands are expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemias.

In another aspect of the invention, a method of treating a mammal comprises administering a therapeutically and/or prophylactically effective amount of a pharmaceutical containing a TLR7 ligand prodrug of the invention. In this aspect the effect may relate to modulation of some portion of the mammal's immune system, especially modulation of cytokine activities of Th1 and Th2, including but not restricted to the interleukin family, e.g., IL-1 through IL-12, and other cytokines such as TNF alpha, and interferons including interferon alpha, interferon beta, and interferon gamma, and their downsteam effectors. Where modulation of Th1 and Th2 cytokines occurs, it is contemplated that the modulation may include stimulation of both Th1 and Th2, suppression of both Th1 and Th2, stimulation of either Th1 or Th2 and suppression of the other, or a bimodal modulation in which one effect on Th1/Th2 levels (such as generalized suppression) occurs at a high concentration, while another effect (such as stimulation of either Th1 or Th2 and suppression of the other) occurs at a lower concentration.

In another aspect of this invention, pharmaceutical compositions containing a prodrug of a TLR7 ligand are administered in therapeutically effective doses to a mammal that is receiving immunomodulatory drugs not included in this invention. In a preferred aspect, the doses of the immunomodulatory drug are reduced below their customary effective dose, to reduce adverse effects. In a second preferred aspect, the immunomodulatory drug is used at its customary dose, but with an improved therapeutic effect when a prodrug of a TLR7 ligand is also administered.

In another aspect of the invention, pharmaceutical compositions containing a prodrug of a TLR7 ligand are administered in a therapeutically effective dose to a mammal that is receiving anti-infective drugs not included in this invention. In a preferred aspect of this invention, the pharmaceutical compositions containing a prodrug of a TLR7 ligand are administered in a therapeutically effective dose with anti-infective drug(s) that act directly upon the infectious agent to inhibit the growth of or kill the infectious agent.

4. BRIEF DESCRIPTION OF THE DRAWINGS

5. DETAILED DESCRIPTION OF THE INVENTION

5.1 Definitions

Figure 1:
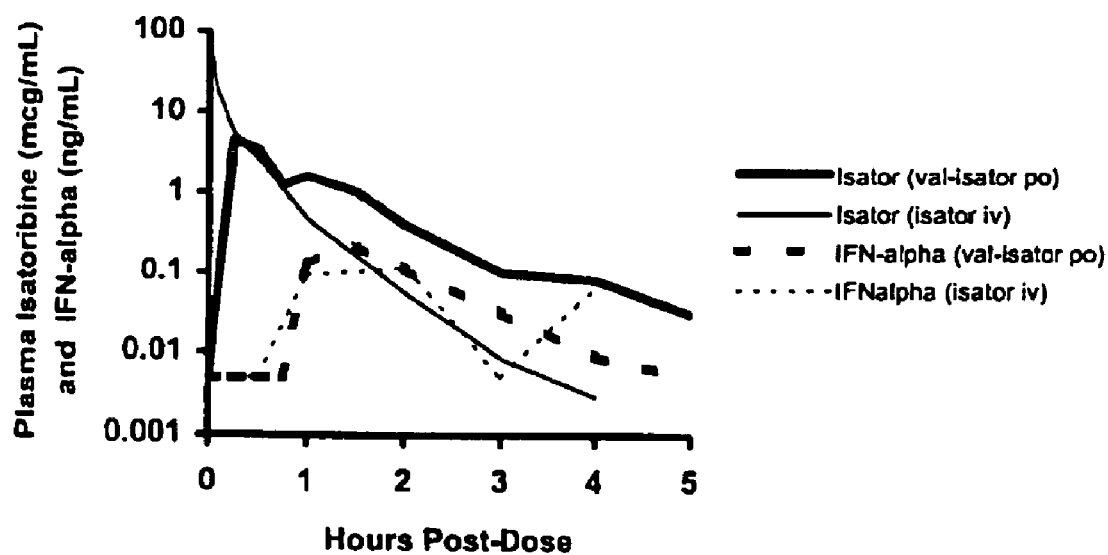
FIG. 1 is a graphical depiction of plasma levels of isatoribine and interferon alpha in mice.

Where the following terms are used in this specification, they are used as defined below:

The terms "comprising" and "including" are used herein in their open, non-limiting sense.

The term "nucleoside" refers to a compound composed of any pentose or modified pentose moiety attached to a specific position of a heterocycle or to the natural position of a purine (9-position) or pyrimidine (1-position) or to the equivalent position in an analog.

The term "purine" refers to nitrogenous bicyclic heterocycles.

The term "D-nucleosides" refers to the nucleoside compounds that have a D-ribose sugar moiety (e.g., Adenosine).

The term "L-nucleosides" refers to the nucleoside compounds that have a L-ribose sugar moiety.

The term "immunomodulator" refers to natural or synthetic products capable of modifying the normal or aberrant immune system through stimulation or suppression.

The term "NOAEL" is the No Observed Adverse Event Level, which is a toxicology term for the dose of drug that results in no significant toxicity under the specified conditions of dose level, frequency, duration in a selected species.

"Ligand" means a low molecular weight molecule capable of binding to a biologic receptor. A ligand may be either an agonist or an antagonist, or may have no effect.

An "agonist" is a ligand that, upon binding, stimulates the receptor to exert a biologic response that is consistent with the normal biologic activity of the receptor.

An "antagonist" is a ligand that, upon binding, causes the receptor to not exert the normal biologic activity of the receptor.

The term "mammal" includes both animals and humans.

The term "preventing" refers to the ability of a compound or composition of the invention to prevent a disease identified herein in mammals diagnosed as having the disease or who are at risk of developing such disease. The term also encompasses preventing further progression of the disease in mammals who are already suffering from or have symptoms of such disease.

The term "treating" refers to:
(i) preventing a disease, disorder, or condition from occurring in a mammal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The terms "α" and "β" indicate the specific stereochemical configuration of a substituent at an asymmetric carbon atom in a chemical structure as drawn.

The terms "patient" or "subject" mean an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the TLR7 ligand or prodrug of a TLR7 ligand of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergizes with another prophylactic or therapeutic agent.

The term "in combination" refers to the use of more than one prophylactic and/or therapeutic agents simultaneously or sequentially and in a manner that their respective effects are additive or synergistic.

The term "pharmaceutically acceptable salts" refer to salts prepared from pharmaceutically acceptable non-toxic acids or bases including inorganic acids and bases and organic acids and bases. If the inventive TLR7 ligand prodrug is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the inventive TLR7 ligand prodrug is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The term "prodrug" is intended to mean any chemical entity that after administration is converted via metabolic actions or solvolysis to a different chemical entity that retains biological activity.

The term "TLR7 ligand prodrug" is intended to mean any chemical entity that after administration is converted via metabolic actions or solvolysis to a different chemical entity that retains biological activity and that is a ligand for TLR7. A TLR7 ligand prodrug may itself be a ligand for TLR7, or it may be "masked" in that it does not function efficiently as a TLR7 ligand.

The term "masked TLR7 ligand prodrug" is intended to mean any chemical entity that after administration is converted via metabolic actions or solvolysis to a different chemical entity that retains biological activity and that is a ligand for TLR7, and where the administered chemical entity is a less efficient ligand for TLR7 than the chemical entity arising from metabolic conversion or solvolysis.

The term "a pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the TLR7 ligand, alter the way in which drugs are distributed in and excreted from the body. However, in some cases, metabolism of a drug is required for therapeutic effect. For example, many anticancer drugs of the anti-metabolite class must be converted to their active forms after they have been transported into a cancer cell.

As used herein, unless otherwise specified, the term "alkyl" means a saturated straight chain or branched non-cyclic hydrocarbon having from 1 to 20 carbon atoms, preferably 1-10 carbon atoms and most preferably 1-4 carbon atoms. Representative saturated straight chain alkyls include -methyl, -ethyl, -n-propyl, -n-butyl, -n-pentyl, -n-hexyl, -n-heptyl, -n-octyl, -n-nonyl and -n-decyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. An alkyl group can be unsubstituted or substituted.

As used herein, unless otherwise specified the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Preferably, the aryl group is a monocyclic ring or bicyclic ring. Representative aryl groups include phenyl, tolyl, anthracenyl, fluorenyl, indenyl, azulenyl, phenanthrenyl and naphthyl. A carbocyclic aryl group can be unsubstituted or substituted.

The term "substituted" means that the specified group or moiety bears one or more substituents. The term "unsubstituted" means that the specified group bears no substituents. A "substituted alkyl" or "substituted aryl" is substituted by one or more substituents including halogen (F, Cl, Br, or I), lower alkyl ($C_{1-6}$), —OH, —NO$_2$, —CN, —CO$_2$H, —O-lower alkyl, -aryl, -aryl-lower alkyl, —CO$_2$CH$_3$, —CONH$_2$, —OCH$_2$CONH$_2$, —NH$_2$, —SO$_2$NH$_2$, haloalkyl (e.g., —CF$_3$, —CH$_2$CF$_3$), —O-haloalkyl (e.g., —OCF$_3$, —OCHF$_2$), and the like.

As used herein and unless otherwise indicated, the term "optically pure" or "stereomerically pure" means a composition that comprises one stereoisomer of a compound and is substantially free of other stereoisomers of that compound. For example, a stereomerically pure compound having one chiral center will be substantially free of the opposite enantiomer of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. Since many of the compounds of the invention comprise saccharides which can exist in either the D or L forms, the invention encompasses either or both D and L sugars. As such, for example, a stereomerically pure D sugar will be substantially free of the L form. In an alternative embodiment, the use of L forms of a TLR7 ligand will be substantially free of the D form. Thus, the methods and compositions disclosed herein include in an alternative embodiment the use of such levorotatory sugars or polymers made therefrom.

The compounds of the invention may exhibit the phenomenon of tautomerism. While Formulas I and II cannot expressly depict all possible tautomeric forms, it is to be understood that Formula I is intended to represent any tautomeric form of the depicted compound and are not to be limited merely to a specific compound form depicted by the formula drawings. For example, it is understood that regardless of whether or not the substituents are shown in their enol or their keto form, they represent the same compound (as shown in the Formula IIa example below).

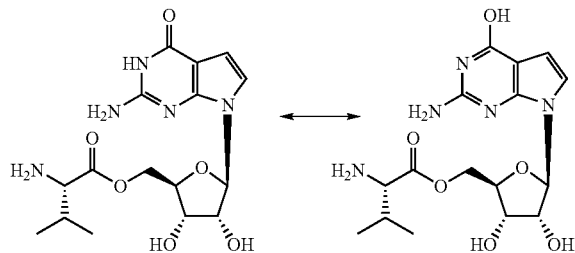

5.2 Identification of TLR7 Ligands

Known TLR7 ligands include, but are not limited to (1) guanosine analogs, such as 7-deazaguanosine and related compounds, including but not limited to those described in Townsend, *J. Heterocyclic Chem,* 13, 1363 (1976), and Seela, et al, *Chem. Ber.,* 114(10), 3395-3402 (1981); 7-allyl, 8-oxoguanosine (loxorabine) and related compounds, including but not limited to those described in Reitz, et al., *J. Med. Chem,* 37, 3561-3578 (1994); 7-methyl, 9-deazaguanosine and related compounds including, but not limited to, those described in Girgis et al., *J. Med. Chem.,* 33, 2750-2755 (1990); 8-bromoguanosine and other 8-halogen substituted purines compounds including, but not limited to, those described in U.S. Pat. No. 4,643,992; 6-amino-9-benzyl-2-butoxy-9H-purin-8-ol, and other 2, 6, 8, 9-substituted purines including, but not limited to, those described in Hirota et al., *J. Med. Chem.,* 45, 5419-5422 (2002), Henry et al., *J. Med. Chem.,*33, 2127-2130 (1990), Michael et al., *J Med Chem.,* 36, 3431-3436 (1993), Furneaux et al., *J. Org. Chem.,* 64 (22), 8411-8412 (1999), Barrio et al; *J. Org. Chem.,* 61, 6084-6085 (1996), U.S. Pat. Nos. 4,539,205, 5,011,828, 5,041,426, 4,880,784, and International Patent Application Publication Nos. WO 94/07904; (2) imidazoquinolines, including but not limited to 1-(4-amino-2-ethoxymethyl-imidazo[4,5-c]quinolin-1-yl)-2-methyl-propan-2-ol (imiquimoid), as described in International Patent Application Publication No. WO 94/17043; 1-isobutyl-1H-imidazo[4,5-c]quinolin-4-ylamine (resiquimoid) as described in International Patent Application Publication No. WO 94/17043 and U.S. patent application Ser. Nos. 10/357,777 (United States Patent Application Publication No. US 2003/0195209), Ser. No. 10/357,733 (United States Patent Application Publication No. US 2003/0186949), Ser. No. 10/358,017(United States Patent Application Publication No. US 2003/0176458), Ser. No. 10/357, 995(United States Patent Application Publication No. US 2003/0162806), Ser. No. 10/165,222 (United States Patent Application Publication No. US 2003/0100764), Ser. No. 10/011,921(United States Patent Application Publication No. US 2003/0065005) and Ser. No. 10/013,059 (United States Patent Application Publication No. US 2002/0173655); U.S. Pat. No. 5,395,937; International Patent Application Publication No. WO 98/17279; and (3) pyrimidine derivatives, including but not limited to 2-amino-6-bromo-5-phenyl-3H-pyrimidin-4-one (bropirimine), and similar substituted pyrimidines including, but not limited to, those described in Wierenga et al., *J. Med. Chem,* 23, 239-240 (1980), Fan et al., *J Heterocyclic Chem.,* 30, 1273 (1993), Skilnick et al., *J. Med. Chem.,* 29, 1499-1504 (1986), Fried, et al., *J. Med. Chem.,* 23, 237-239 (1980), and Fujiwara et al., *Bioorg. Med. Chem. Lett.,* 10(12) 1317-1320 (2000). The entireties of each of the patents, patent publications and publications identified herein are incorporated herein by reference.

In addition to the above TLR7 ligands, additional TLR7 ligands can be readily identified by known screening methods. See, e.g., Hirota et al., *J. Med. Chem.,* 45, 5419-5422 (2002); and Akira S. et al., *Immunology Letters,* 85, 85-95 (2003). Using a variant of one of these known screening methods (as described in Section 6.1), analogs and derivatives of adenine were also identified as TLR7 ligands. Adenine derivatives known in the art are described in European Patent Application Publication Nos. EP 1 035 123, EP 1 043 021, and EP 0 882 727; U.S. Pat. Nos. 6,376,501; 6,329,381; 6,028,076, and United States Patent Application Publication No. US 2003/0162806.

The TLR7 ligands of Formulas Ia-Ih can be synthesized using methods known to one of skill in the art, particularly in light of the references and patents listed above.

5.3 Preparation of TLR7 Ligand Prodrugs

The TLR7 ligand prodrugs of the invention are prepared by making an (a) amide, carbamate, or amidine moiety after conversion of a TLR7 ligand amine substituent, (b) ester, carbonate, carbamate, ether, imidate, acetal, or ketal moiety after conversion of a TLR7 ligand alcohol substituent, (c) acetal or ketal moiety after conversion of a TLR7 ligand amine substituent, (d) imidate moiety after conversion of a TLR7 ligand carbonyl of an amido substituent, (e) deoxygenated moiety after conversion of a TLR7 ligand oxo substituent of pyrimidine or guanosine, or (f) amine. For example, TLR7 ligand prodrugs are prepared by either (1) converting an hydroxyl (OH) substituents of the TLR7 ligand into an amino acid ester, or (2) making an amine substituent of the TLR7 ligand into an amide or carbamate. The process for preparing prodrugs is well known in the art and is described by *Burger's Medicinal Chemistry and Drug Chemistry*, 1, 172-178, 949-982 (1995). See also Bertolini et al., *J. Med. Chem.*, 40, 2011-2016 (1997); Shan, et al., *J. Pharm. Sci.*, 86 (7), 765-767; Bagshawe, *Drug Dev. Res.*, 34, 220-230 (1995); Bodor, *Advances in Drug Res.*, 13, 224-331 (1984); Bundgaard, *Design of Prodrugs* (Elsevier Press 1985); Larsen, *Design and Application of Prodrugs*, Drug Design and Development (Krogsgaard-Larsen et al., eds., Harwood Academic Publishers, 1991); Dear et al., *J. Chromatogr. B*, 748, 281-293 (2000); Spraul et al., *J. Pharmaceutical & Biomedical Analysis*, 10, 601-605 (1992); and Prox et al., *Xenobiol.*, 3, 103-112 (1992).

Schemes 1-18 show a general procedure to prepare representative compounds of Formula II.

Schemes 1-6 describe how 5'-amino acid esters can be synthesized from analogs and derivatives of guanosine.

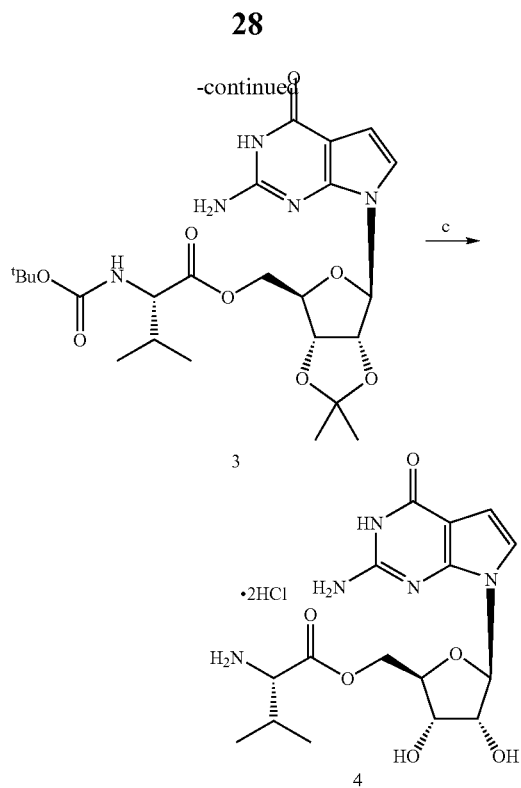

a) 2,2-dimethoxypropane, acetone, DMSO, MeSO$_3$H, 0° C.
b) BOC—NHCHR$^1$CO$_2$H, EDC, DMAP, PhMe, 0° C. - rt
c) anh. HCl, iPrOAc, iPrOH Scheme 1

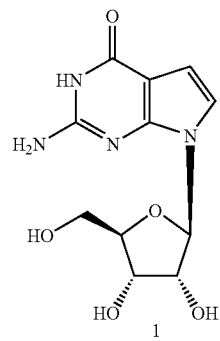

Townsend, *JHC*, 13
1976, 1363
Seela, et al, *Chem. Ber.*,
114, 10, 1981,
3395-3402

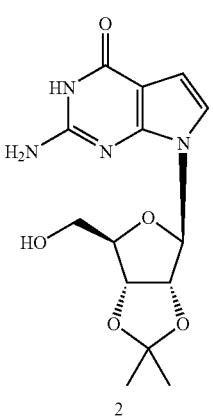

Scheme 2

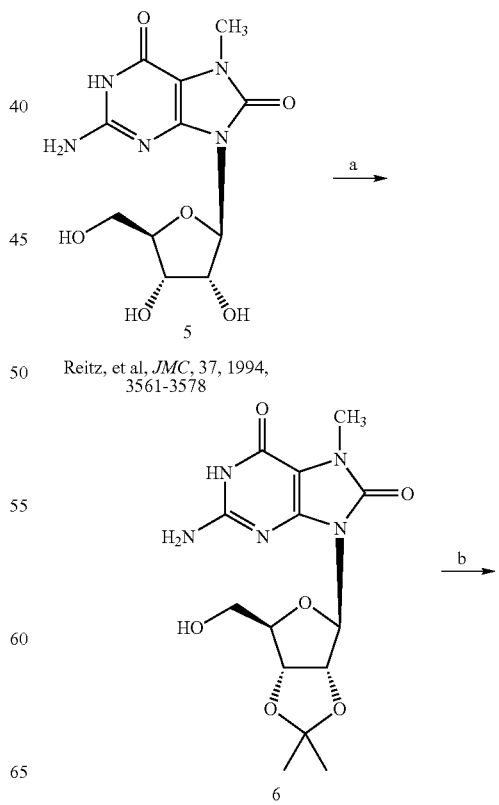

Reitz, et al, *JMC*, 37, 1994,
3561-3578

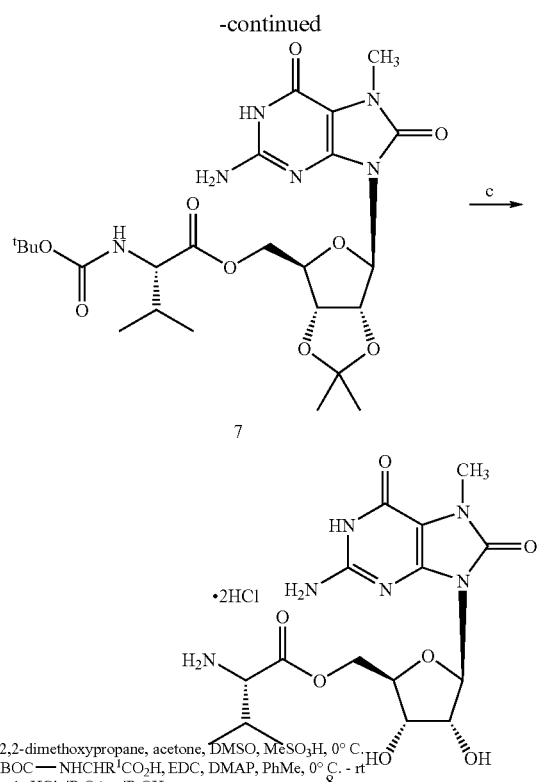
7
a) 2,2-dimethoxypropane, acetone, DMSO, MeSO₃H, 0° C.
b) BOC—NHCHR¹CO₂H, EDC, DMAP, PhMe, 0° C. - rt
c) anh. HCl, iPrOAc, iPrOH
8
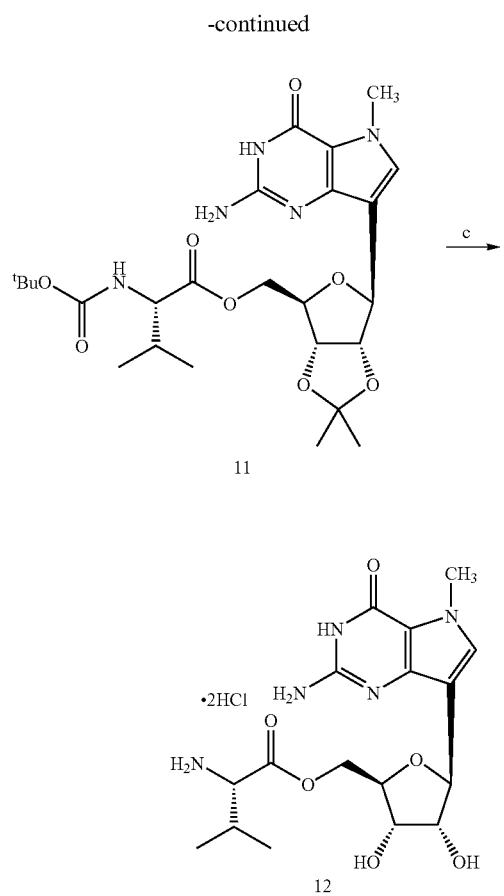
11
12
a) 2,2-dimethoxypropane, acetone, DMSO, MeSO₃H, 0° C.
b) BOC—NHCHR¹CO₂H, EDC, DMAP, PhMe, 0° C. - rt
c) anh. HCl, iPrOAc, iPrOH
Scheme 3
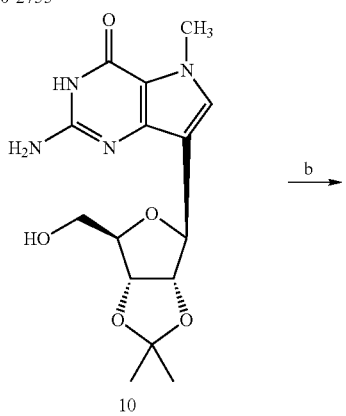
9
Girgis, et al, *JMC*, 33, 1990, 2750-2755
10
Scheme 4
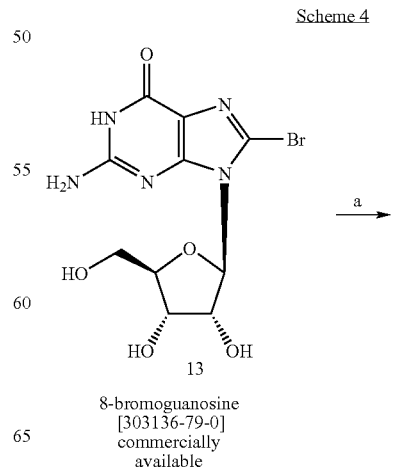
13
8-bromoguanosine
[303136-79-0]
commercially available

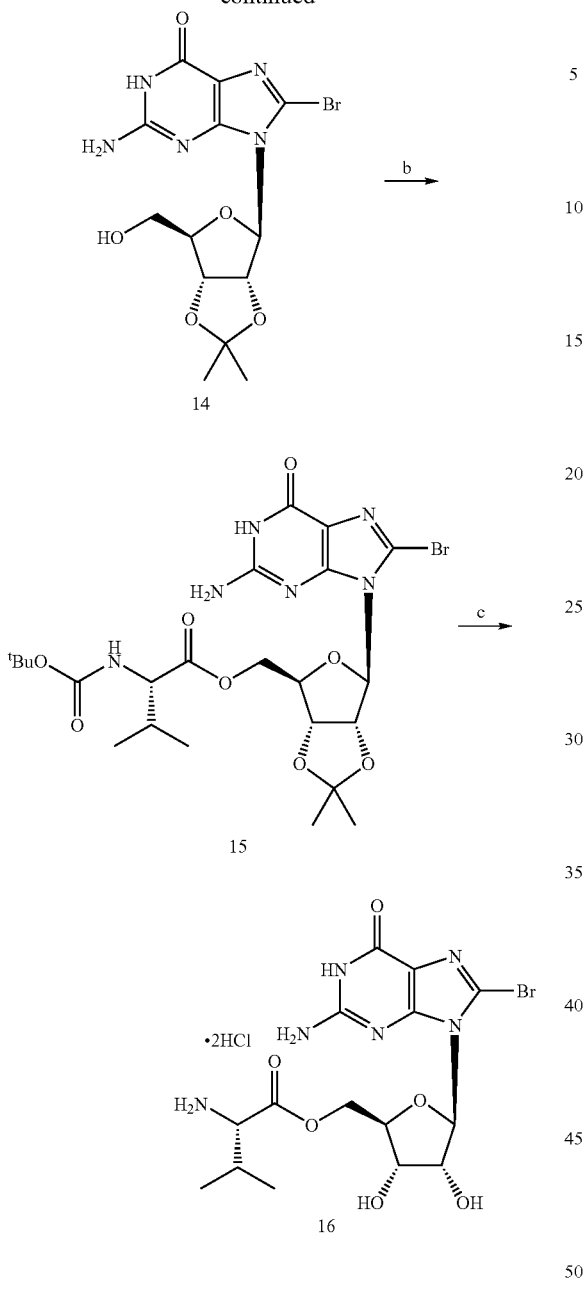

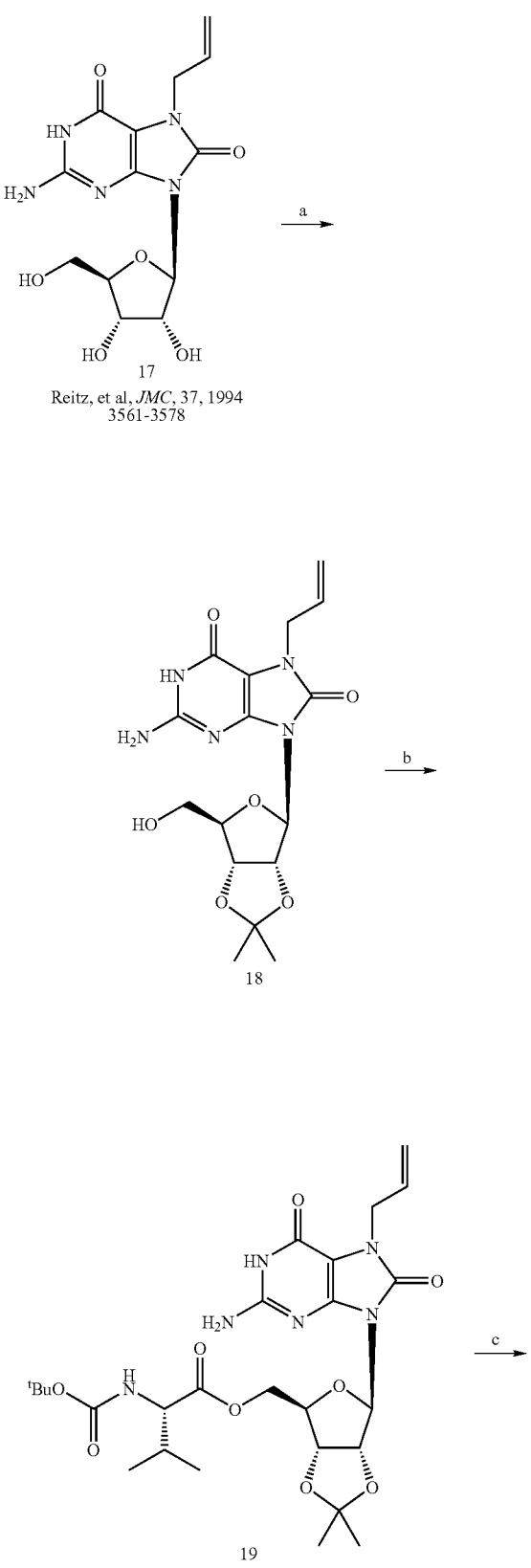

a) 2,2-dimethoxypropane, acetone, DMSO, MeSO$_3$H, 0° C.
b) BOC—NHCHR$^1$CO$_2$H, EDC, DMAP, PhMe, 0° C. - rt
c) anh. HCl, iPrOAc, iPrOH In a typical synthetic route, the 2',3'-hydroxyl groups of the β-D-ribose moiety of Formulaa Ia, Ib, Id, Ie, or Ih can first protected, preferably with an acetonide as shown for 2, 6, 10, or 14. The free 5'-hydroxyl can then be subjected to a variety of esterification methods with a N-protected amino acid to form 3, 7, 11, or 15. The nitrogen of the amino acid ester and the 2',3'-hydroxyls of the ribose unit can then be subjected to various deprotection conditions, preferably concurrently, followed by salt formation of the free amine of the amino acid ester as illustrated for 4, 8, 12, or 16.

-continued

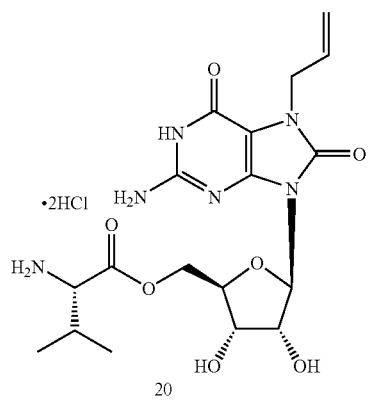
20 a) 2,2-dimethoxypropane, acetone, DMF, MeSO₃H, 0° C.
b) BOC—NHCHR¹CO₂H, EDC, DMAP, PhMe, 0° C. - rt
c) AcCl, CH₃OH Scheme 6

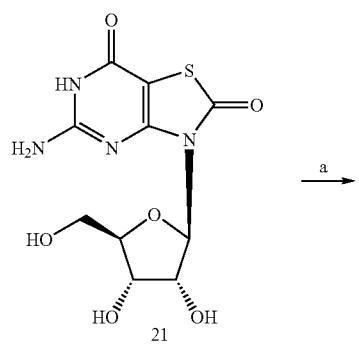
21

Kini, et al, *JMC*, 34, 1991
3006-3010

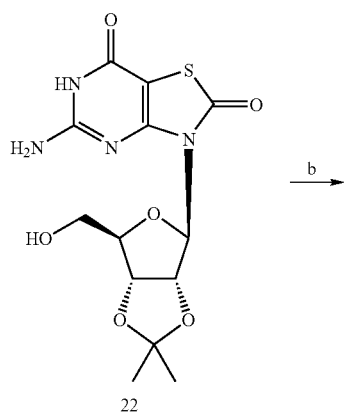
22

-continued

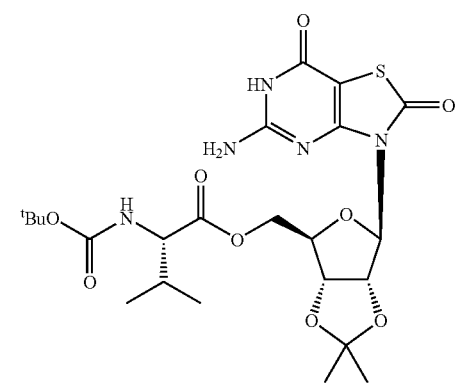
23

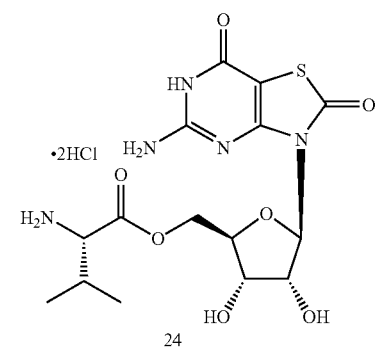
24 a) 2,2-dimethoxypropane, acetone, DMSO, MeSO₃H, 0° C.
b) BOC—NHCHR¹CO₂H, EDC, DMAP, PhMe, 0° C. - rt
c) anh. HCl, iPrOAc, iPrOH In the synthetic routes shown in Schemes 5 and 6, the 2′,3′-hydroxyl groups of the β-D-ribose moiety of compound 17 and 21 were first protected with an acetonide to form 18 and 22 respectively. The free 5′-hydroxyl was then subjected to esterification with a N-tert-butoxycarbonyl valine to form 19 and 23 respectively. The nitrogen of the amino acid ester and the 2′,3′-hydroxyls of the ribose were concurrently deprotected forming the hydrochloride salts as illustrated for 20 and 24.

Schemes 7 and 8 describe how carbamates and carbonates can be synthesized from analogs and derivatives of adenine.

Scheme 7

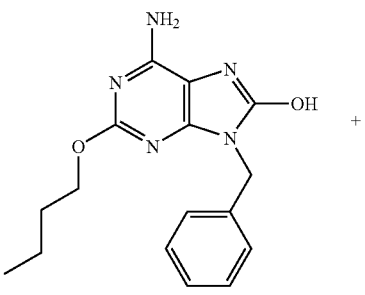
25

Hirota, et al, JMC, 45,
2002, 5419-5422

-continued

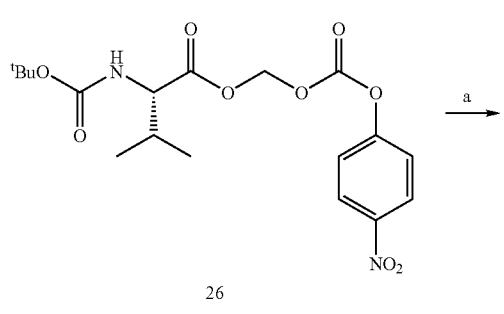

26

Gangwar, et al, JOC, 62, 1997
1356-1362

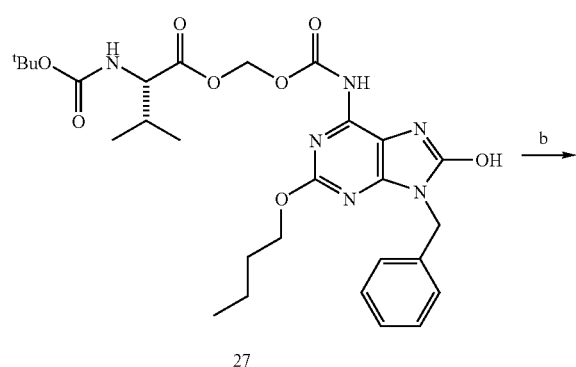

27

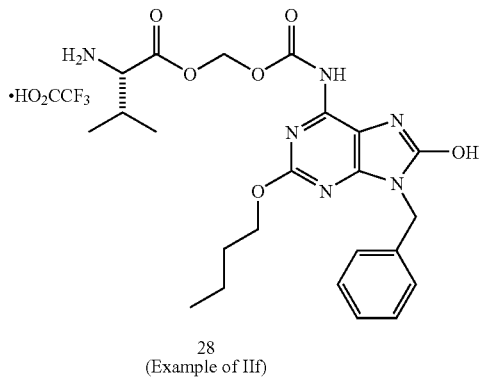

28
(Example of IIf)

a) HOBT, DMF, CH$_2$Cl$_2$, 0° C.
b) TFA, CH$_2$Cl$_2$, 0° C. - rt

In a typical synthetic route, the amino group of Formula If can be subjected to a variety of conditions with carbonates or chloroformates to form carbamates. In the case of 27, the N-terminal protected amine of the resulting amino acid ester can be subjected to deprotection conditions to form salts such as 28.

Scheme 8

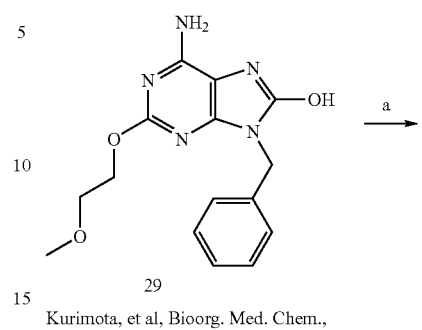

29

Kurimota, et al, Bioorg. Med. Chem.,
12, 2004, p. 1091-1099

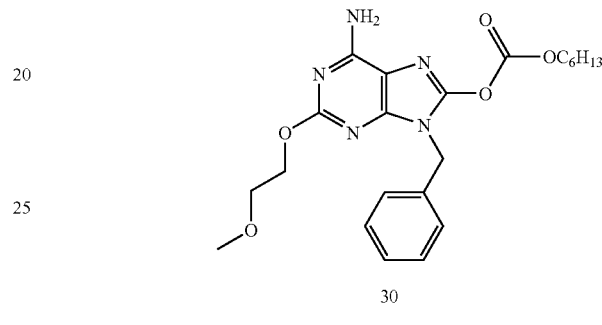

30 a) C$_6$H$_{13}$OC(O)Cl, (iPR)$_2$NEt, CH$_2$Cl$_2$, MeOH, DMAP, 0-35° C.

In Scheme 8 the hydroxyl group of adenine derivative 29 was esterified with n-hexyl chlorofomate to give carbonate 30.

Schemes 9 and 10 describes how carbamates and can be synthesized from imidazoquinoline analogs.

Scheme 9

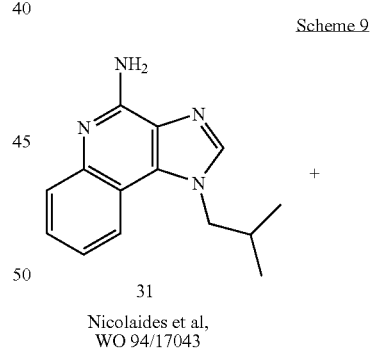

31

Nicolaides et al,
WO 94/17043

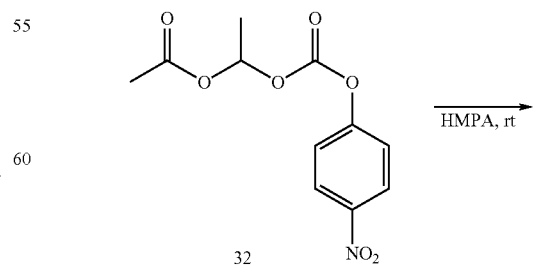

32

Alexander, et al, JMC, 31,
1988, 318-322

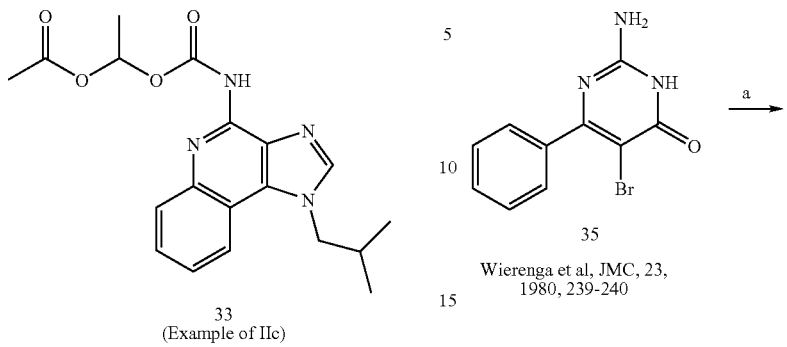

33
(Example of IIc)

In a typical synthetic route, the amino group of analogs of Formula Ic can be subjected to a variety of conditions with carbonates, pyrocarbonates or chloroformates to form carbamates.

Scheme 10

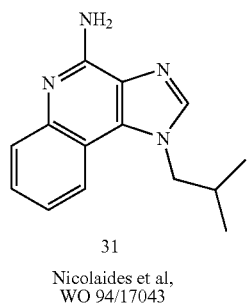

31
Nicolaides et al,
WO 94/17043

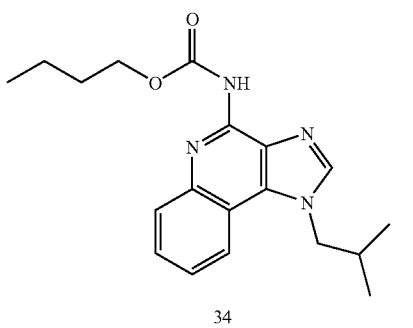

34 a) [C$_5$H$_{11}$OC(O)]$_2$O, NEt$_3$, CHCl$_3$, 40° C.

In Scheme 10 imidazoquinoline 31 was treated with n-pentyl pyrocarbonate to give pentyl carbamate 34.

Schemes 11-12 described how to synthesize carbamates and imidates of pyrimidines of formula Ig.

Scheme 11

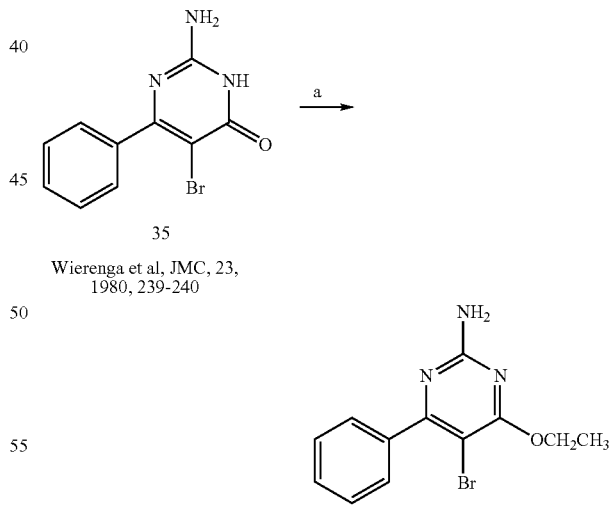

35
Wierenga et al, JMC, 23, 1980, 239-240

36 (Example of IIg)
Fan et al, JHC, 30, 1993, 1273-1276 a) [EtO(CO)]$_2$O, NEt$_3$, DMF, 65° C.

In a typical synthesis of carbamates, the amino group of 35 was subjected to ethyl pyrocarbonate under conditions shown above to form carbamate 36.

Scheme 12

35
Wierenga et al, JMC, 23, 1980, 239-240

37 (Example of IIg)

a) polymer supported PPh$_3$, EtOH, DEAD, THF, rt

In a typical synthesis of imidates, the amino group of 35 was subjected to ethyl alcohol under Mitsunobu type conditions shown above to form ethoxy derivative 37.

Scheme 13 describes how carbamates and can be synthesized from imidazoquinoline analogs.

Scheme 13

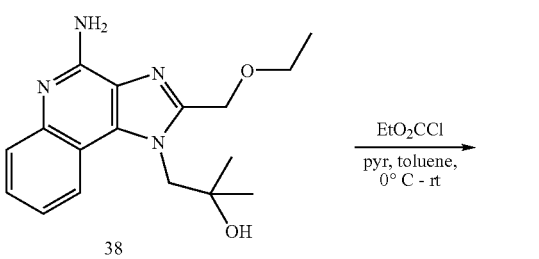

In a typical synthetic route, the amino group of a derivative of Formula Ic can be subjected to a variety of conditions with carbonates, pyrocarbonates or chloroformates to form carbamates.

Scheme 14 shows a general procedure for preparing 7-allyl-2-Amino-9-β-D-ribofuranosyl-7,9-dihydro-purin-8-one.

Scheme 14

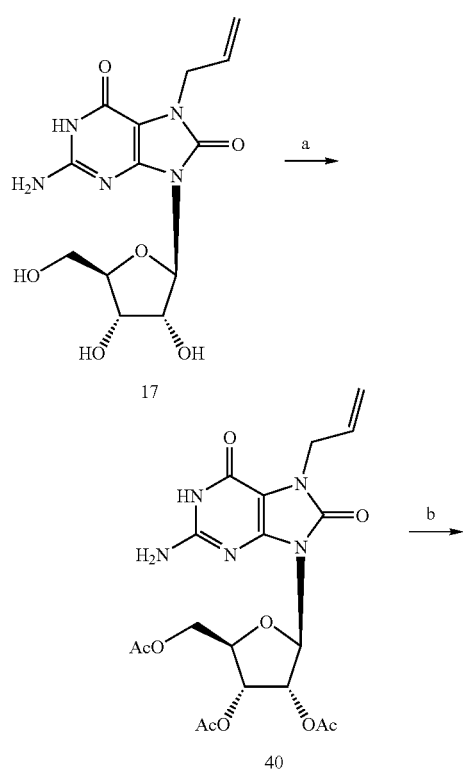

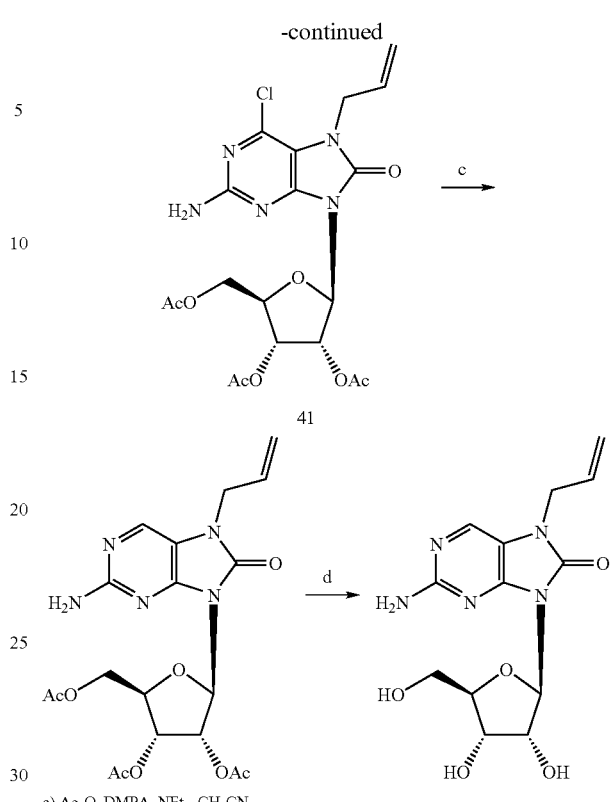

a) Ac₂O, DMPA, NEt₃, CH₃CN
b) POCl₃, 75° C.
c) Zn—Cu, AcOH, 70° C.
d) K₂CO₃, CH₃OH, rt

In a typical synthetic routes, 7-allyl-2-amino-9-β-D-ribofuranosyl-7,9-dihydro-1H-purine-6,8-dione 17, was protected at the 2',3',5'-hydroxyl groups of the β-D-ribose, preferably with acyl groups as shown for 40, can be subjected to a variety of conditions to convert the carbonyl at the C-6 position to various groups, including but not limited to halogen, as shown for 41, that are susceptible to reduction. Following reduction under hetero- or homogeneous reaction conditions, the 2',3',5'-hydroxyls of the ribose unit are then subjected to appropriate deprotection conditions, to produce 43. Compound 43 can further be appropriately modified if so desired.

Scheme 15 shows a general procedure for preparing 7-allyl-2-Amino-6-ethoxy-9-β-D-ribofuranosyl-7,9-dihydro-purin-8-one.

Scheme 15

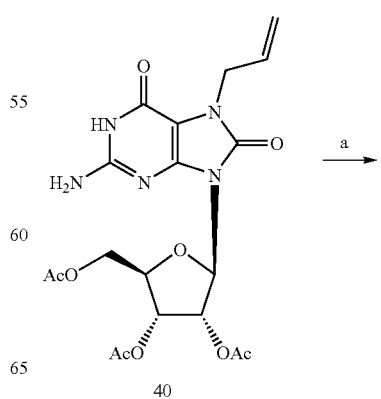

-continued

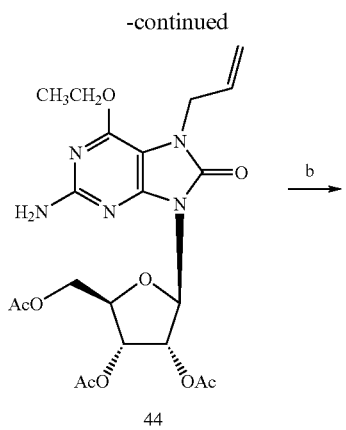

44

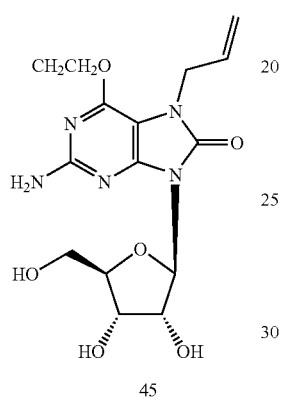

45 a) polymer supported PPh₃, EtOH, DEAD, THF, rt
b) K₂CO₃, CH₃OH, rt

In a typical synthetic route, 40 can be subjected to a variety of conditions to convert the carbonyl at the C-6 position to various imido-ethers, including but not limited to ethyl, as shown for 44. The 2',3',5'-hydroxyls of the ribose unit are then subjected to appropriate deprotection conditions, to produce 45. Compound 45 can further be appropriately modified if so desired.

Scheme 16 describes how ethers can be synthesized from analogs and derivatives of adenine.

Scheme 16

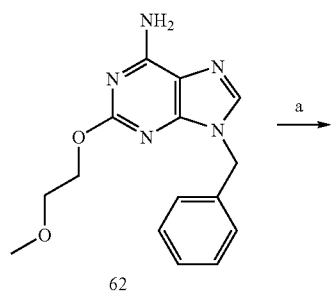

62

Kurimota, et al, Bioorg. Med. Chem., 12, 2004, p. 1091-1099

-continued

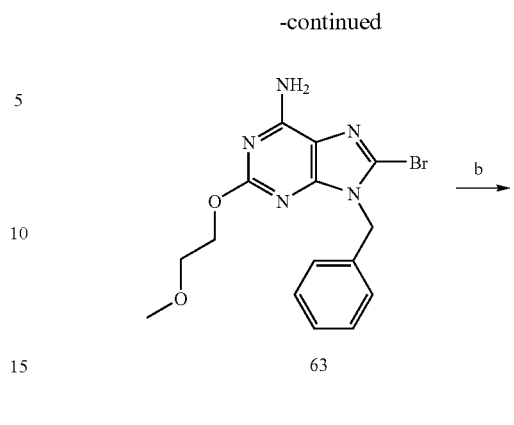

63

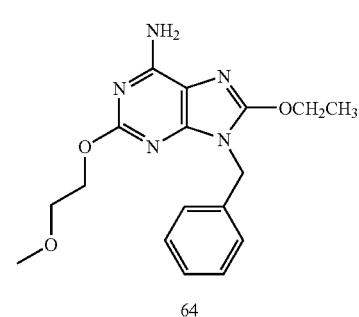

64 a) Br₂, CH₂Cl₂
b) NaOEt, EtOH

In a typical synthetic route, the adenine derivative can be halogenated at C-8. The halogen can then be displaced with an appropriate alkoxide to form derivatives such as 64.

Scheme 17 shows a general procedure for preparing 7-allyl-2-Amino-6-substituted alkoxy-9-β-D-ribofuranosyl-7,9-dihydro-purin-8-ones.

Scheme 17

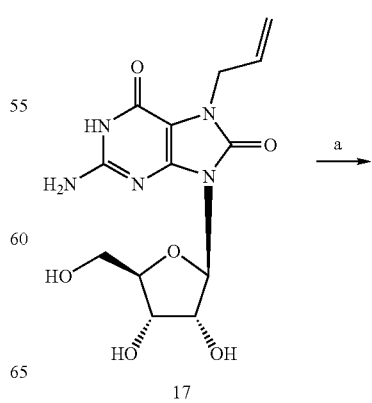

17

43

-continued

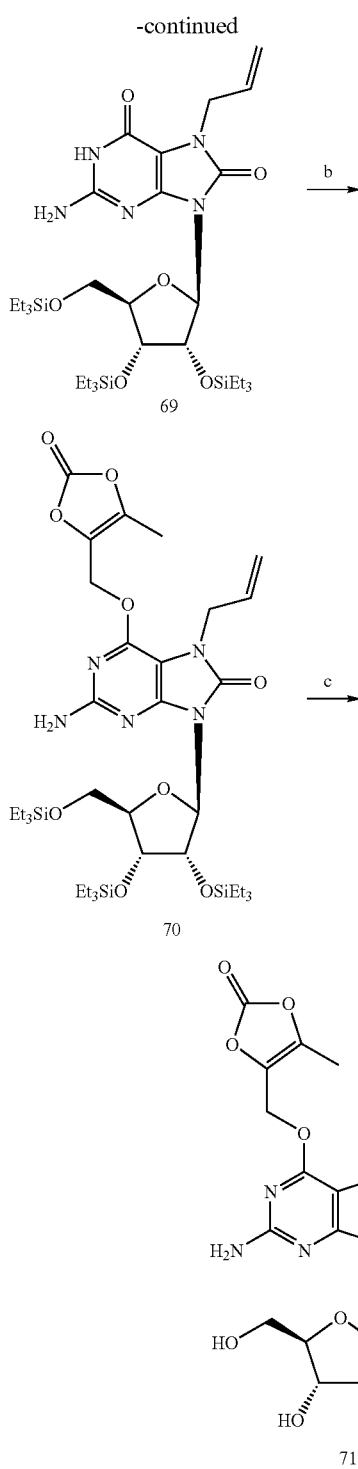

a) Et₃SiCl, imidazole, DMF, rt b) 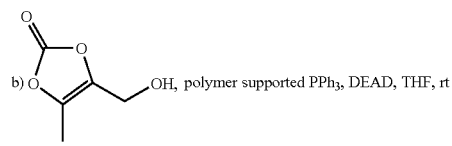 polymer supported PPh₃, DEAD, THF, rt c) HF—NEt₃, CH₃OH, rt

44

In a typical synthetic route, the hydroxyl groups on ribose of 17 can be protected as silyl ethers. The carbonyl at the C-6 position of 69 can be subjected to a variety of conditions to convert the carbonyl to various imido-ethers, including but not limited to the ether of 4-hydroxymethyl-5-methyl-[1,3]dioxol-2-one, as shown for 70. The 2',3',5'-hydroxyls of the ribose unit are then subjected to appropriate deprotection conditions, to produce 71.

Scheme 18 shows a general procedure for preparing 7-allyl-2-Amino-6-substituted alkoxy-9-β-D-ribofuranosyl-7,9-dihydro-purin-8-ones.

Scheme 18

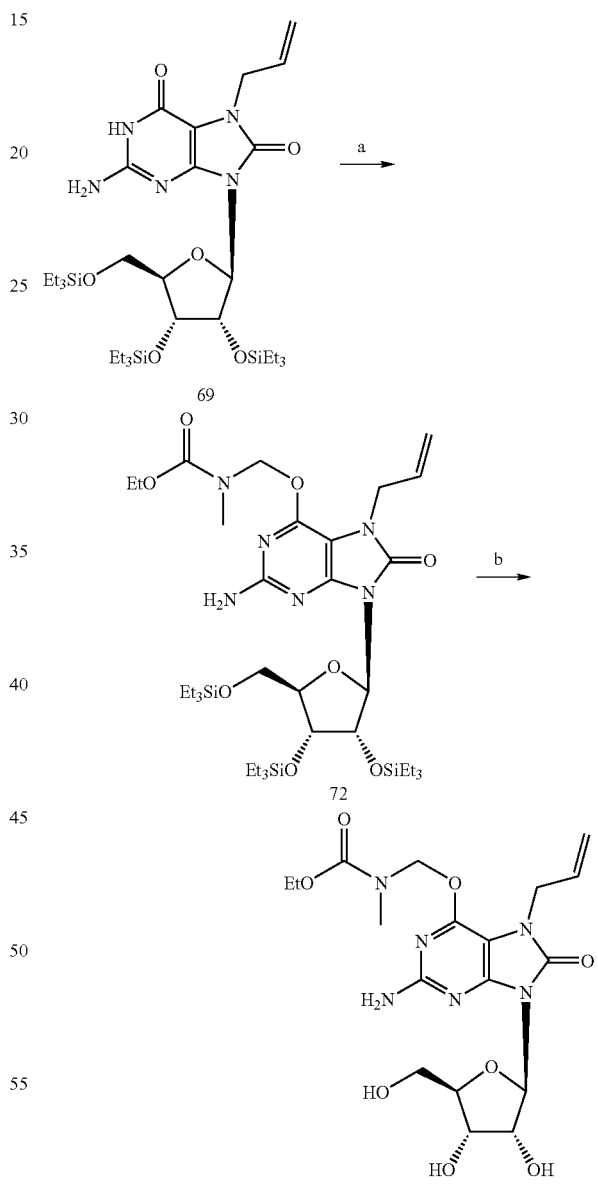

a) HOCH₂N(CH₃)CO₂Et, polymer supported PPh₃, DEAD, THF, rt
b) HF—NEt₃, CH₃OH, rt The carbonyl at the C-6 position of 69 can be subjected to a variety of conditions to convert the carbonyl to various imido-ethers, including but not limited to the ether of N-methyl-N-(hydroxymethyl)urethane, as shown for 72. The 2',3', 5'-hydroxyls of the ribose unit are then subjected to appropriate deprotection conditions, to produce 73. Compound 73 can further be appropriately modified if so desired.

5.4 Methods of Treatment and Prevention of Hepatitis C Viral Infections

The present invention provides methods for treating or preventing a hepatitis C virus infection in a patient in need thereof.

The present invention further provides methods for introducing a therapeutically effective amount of a TLR7 ligand or a prodrug thereof, or combination of such ligands and prodrugs into the blood stream of a patient in the treatment and/or prevention of hepatitis C viral infections.

The magnitude of a prophylactic or therapeutic dose of a TLR7 ligand or TLR7 ligand prodrug of the invention or a pharmaceutically acceptable salt, solvate, hydrate, or stereoisomer thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to viral polymerase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the TLR7 ligand prodrug may be formulated in animal models to achieve a circulating plasma concentration range of the TLR7 ligand that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the TLR7 ligands are exposed to the ligand and the magnitude of response is measured by an appropriate technique. The assessment of the TLR7 ligand potency is then evaluated with respect to the TLR7 ligand prodrug potency, and the degree of conversion of the TLR7 ligand prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a TLR7 ligand of the invention or a pharmaceutically acceptable salt, solvate, hydrate, or stereoisomer thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular TLR7 ligands prodrugs; suitable doses can be predicted on the basis of the aforementioned in vitro measurements, in particular by use of such measurements of the TLR7 ligand to which the TLR7 ligand prodrug is related, and on the basis of animal studies, such that smaller doses will be suitable for those TLR7 ligand prodrugs that show effectiveness at lower concentrations than other TLR7 ligand prodrugs when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day. In a preferred embodiment for compounds such as prodrugs of 3-β-D-ribofuranosylthiazolo[4,5-d]pyrimidines from 200 mg to 8000 mg per day is administered in about one to four divisions a day. Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In a preferred embodiment, the compounds of the invention are administered to provide systemic distribution of the compound within the patient. In a related embodiment, the compounds of the invention are administered to produce a systemic effect in the body.

In another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, β-interferons, alkylating agents, hormones or cytokines. In a preferred embodiment the invention encompasses the administration of an additional therapeutic agent that is HCV specific or demonstrates anti-HCV activity.

The TLR7 ligands prodrugs of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricet®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)),aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lin-
cosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The TLR7 ligand prodrugs of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The TLR7 ligand prodrugs of the invention can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The TLR7 ligands or TLR7 ligand prodrugs of the invention can be administered or formulated in combination with an antifungal agent. Suitable antifingal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The TLR7 ligands or TLR7 ligand prodrugs of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalatei, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone diproprionate, amcinonide, beclomethasone dipropionate, betamethasone, betamethasone benzoate, betamethasone diproprionate, betamethasone sodium phosphate, betamethasone valerate, clobetasol proprionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The TLR7 ligands or TLR7 ligand prodrugs of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the alpha-interferons, beta-interferons, gamma-interferons, adefovir, clevudine, entecavir, and pleconaril.

The TLR7 ligands or TLR7 ligand prodrugs of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114 (IDEC)) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The TLR7 ligands or TLR ligand prodrugs of the invention can be administered or formulated in combination with an agent which inhibits viral enzymes, including but not limited to inhibitors of HCV protease, such as BILN 2061 and inhibitors of NS5b polymerase such as NM107 and its prodrug NM283 (Idenix Pharmaceuticals, Inc., Cambridge, Mass.).

The TLR7 ligands or TLR7 ligand prodrugs of the invention can be administered or formulated in combination with an agent which inhibits HCV polymerase such as those described in Wu, Curr Drug Targets Infect Disord. 2003;3(3): 207-19 or in combination with compounds that inhibit the helicase function of the virus such as those described in Bretner M, et al Nucleosides Nucleotides Nucleic Acids. 2003;22(5-8):1531, or with inhibitors of other HCV specific targets such as those described in Zhang X. IDrugs. 2002;5 (2): 154-8.

The TLR7 ligands or TLR7 ligand prodrugs of the invention can be administered or formulated in combination with an agent that inhibits viral replication.

The TLR7 ligands or TLR ligand prodrugs of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g., IFN-alpha, and IFN-gamma).

The TLR7 ligands or TLR7 ligand prodrugs of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The TLR7 ligands or TLR7 ligand prodrugs of the invention can be administered or formulated in combination with β-interferons which include, but are not limited to, interferon beta-1a, interferon beta-1b.

The TLR7 ligands or TLR7 ligand prodrugs of the invention can be administered or formulated in combination with α-interferons which include, but are not limited to, interferon alpha-1, interferon alpha-2a (roferon), interferon alpha-2b, intron, Peg-Intron, Pegasys, consensus interferon (infergen) and albuferon.

The TLR7 ligands or TLR7 ligand prodrugs of the invention can be administered or formulated in combination with an absorption enhancer, particularly those which target the lymphatic system, including, but not limited to sodium glycocholate; sodium caprate; N-lauryl-γ-D-maltopyranoside; EDTA; mixed micelle; and those reported in Muranishi Crit. Rev. Ther. Drug Carrier Syst., 7-1-33, which is hereby incorporated by reference in its entirety. Other known absorption enhancers can also be used. Thus, the invention also encompasses a pharmaceutical composition comprising one or more TLR7 ligand prodrugs of the invention and one or more absorption enhancers.

The TLR7 ligands or TLR7 ligand prodrugs of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more TLR7 ligands or TLR7 ligand prodrugs of the invention without an additional therapeutic agent.

Pharmaceutical Compositions and Dosage Forms

Pharmaceutical compositions and single unit dosage forms comprising a TLR7 ligand or prodrug of the invention, or a pharmaceutically acceptable salt, hydrate or stereoisomer thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, a pharmaceutical composition encompassed by this embodiment includes a TLR7 ligand or prodrug of the invention, or a pharmaceutically acceptable salt, hydrate or stereoisomer thereof, and at least one additional therapeutic agent. Examples of additional therapeutic agents include, but are not limited to, those listed above in section 5.2.2.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder.

These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise TLR7 ligand prodrugs of the invention, or a pharmaceutically acceptable salt, hydrate, or stereoisomers thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to, those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophilized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g., Remington's Pharmaceutical Sciences, 18th eds., Mack Publishing, Easton Pa. (1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The TLR7 ligands or TLR7 ligand prodrugs of the invention may also be administered directly to the lung by inhalation. For administration by inhalation, a TLR7 ligand can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a TLR7 ligand directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a TLR7 ligand to the lung (see, e.g., Raleigh et al., Proc. Amer. Assoc. Cancer Research Annual Meeting, 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a TLR7 ligand or TLR7 ligand prodrug to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver TLR7 ligands or TLR ligand prodrugs to the lung. Nebulizers create aerosols from liquid drug formulations by using, for example, ultrasonic energy to form fine particles that can be readily inhaled (See e.g., Verschoyle et al., British J. Cancer, 1999, 80, Suppl 2, 96, which is herein incorporated by reference). Examples of nebulizers include devices supplied by Sheffield/Systemic Pulmonary Delivery Ltd, Aventis, and Batelle Pulmonary Therapeutics. See U.S. Pat. Nos. 5,954,047; 5,950,619; 5,970,974, which are herein incorporated by reference.

In a particularly preferred embodiment, an electrohydrodynamic ("EHD") aerosol device is used to deliver TLR7 ligands and TLR7 ligand prodrugs to the lung. EHD aerosol devices use electrical energy to aerosolize liquid drug solutions or suspensions (see, e.g., Noakes et al., U.S. Pat. No. 4,765,539; Coffee, U.S. Pat. No., 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the TLR7 ligands and TLR7 ligand prodrugs formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of TLR7 ligand and TLR7 ligand prodrugs will be known to the skilled artisan and are within the scope of the invention.

Liquid drug formulations suitable for use with nebulizers and liquid spray devices and EHD aerosol devices will typically include a TLR7 ligand or TLR7 ligand prodrug with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the TLR7 ligand or prodrug of a TLR7 ligand. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598; Biesalski, 5,556,611, which are herein incorporated by reference) A TLR7 ligand or prodrug of a TLR7 ligand can also be formulated in rectal or vaginal compositions such as suppositories or retention enemas, e.g., containing conventional suppository bases such as cocoa butter or other glycerides.

In addition to the formulations described previously, a TLR7 ligand or TLR7 ligand prodrug can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver TLR7 ligands and TLR7 ligand prodrugs. Certain organic solvents such as dimethylsulfoxide can also be employed, although usually at the cost of greater toxicity. A TLR7 ligand or prodrug of a TLR7 ligand can also be delivered in a controlled release system. In one embodiment, a pump can be used (Sefton, CRC Crit. Ref Biomed Eng., 1987, 14, 201; Buchwald et al., Surgery, 1980, 88, 507; Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem., 1983, 23, 61; see also Levy et al., Science, 1985, 228, 190; During et al., Ann. Neurol., 1989, 25,351; Howard et al., 1989, J. Neurosurg. 71, 105). In yet another embodiment, a controlled-release system can be placed in proximity of the target of the compounds of the invention, e.g., the lung, thus requiring only a fraction of the systemic dose (see, e.g., Goodson, in Medical Applications of Controlled Release, supra, vol. 2, pp. 115 (1984)). Other controlled-release system can be used (see, e.g. Langer, Science, 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., Remington's Pharmaceutical Sciences, 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a TLR7 ligand prodrug useful for the treatment or prevention of a Hepatitis C virus infection. In other embodiments, the invention provides a pharmaceutical pack or kit comprising one or more containers comprising a TLR7 ligand prodrug useful for the treatment or prevention of a Hepatitis C virus infection and one or more containers comprising an additional therapeutic agent, including but not limited to those listed in section 5.2.2 above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Assays

The TLR7 ligands, TLR ligand prodrugs, compositions and dosage forms of the invention can be tested in vitro or in vivo by a variety of methods known in the art to test activity. See, for example, the methods discussed below and used throughout the examples.

A range of assays for the purpose of evaluating TLR7 activity are available, and are described in the following publications, each of which is incorporated-by-reference: Hirota et al., *J Med Chem.*, 45, 5419-5422 (2002); and Akira S. et al., *Immunology Letters*, 85, 85-95 (2003). For example, one system useful for the assay of TLR7 ligands is where the gene for TLR7 is cloned by methods known to those of skill in the art and transfected into an appropriate cell type such that TLR7 is expressed and coupled to a NFkB-luciferase reporter plasmid. In this cell system, exposure to TLR7 ligand prodrugs in cell culture results in a measurable luminescence signal. See, e.g., Lee et al., *Proc. Nat. Acad. USA*, 100, 6646-6651 (2003); Hemmi et al., *Nat. Immunol.*, 3, 196-200 (2002); and Jurk et al., *Nat. Immunol.*, 3, 499 (2002) (wherein the Lee et al., Hemmi et al., and Jurk et al., references are all incorporated herein by reference).

Another example of an in vitro method is to expose human peripheral blood mononuclear cells (PBMC) to the candidate TLR7 ligand prodrug for a predetermined interval (e.g., 2 hours to 24 hours), followed by measurement of immunologic activity. Such immunologic activity may include induction of the synthesis of cytokines, which can be measured in the culture supernate by ELISA assay of the cytokine protein, such as a Type 1 interferon (interferon alpha, interferon beta) or Type 2 interferon (interferon gamma). Alternatively, the PBMC can be harvested after incubation with the candidate TLR7 ligand prodrug, the PBMC RNA extracted, and the level of induction of immune system genes determined by RNAse protection assays of the extracted RNA. Genes typically induced include 2'5'-OAS, or interferon gamma, but a range of cytokines can be measured. See, e.g., Hirota et al., J. Med. Chem., 45, 5419-5422 (2002).

RNAse protection assays (RPA) are a method known in the art wherein RNA analytes are quantitated by first hybridizing them to a radioalabeled RNA sequence specific for the analyte RNA, followed by digestion with enzymes that selectively degrade single stranded RNA. The sample is then submitted to gel electrophoresis under conditions that resolve the hybridized, protected double stranded RNA. The gel is then autoradiographed to reveal the location and intensity of the bands. These can be quantitated by methods well known in the art. Multiple analyte RNA species can be simultaneously assayed, if the protected fragments are sufficiently different in size to allow their separation by gel electrophoresis. Comparison of the levels of an analyte RNA to control RNA species that is expressed at constant levels in cells provides an internal control that enable changes in levels of the analyte RNA species to be monitored even if the total amount of RNA varies. Such RNAse protection assays can be performed as follows:

RNA is purified from PMBC pellets using the "RNAeasy" kit (Qiagen), according to the manufacturer's instructions. Template sets may be obtained from PharMingen (BD Biosciences); a useful set that is commercially available from this supplier contains materials allowing the assay of TNF-a, IL12 p35, IP10, IL-1a, IL-1b, IL-6, Interferon gamma, and the control RNA species L32 and GAPDH. This template set contains DNA that is appropriate for synthesis of the proper RNA probe for each of the listed genes.

Probe synthesis is performed using the PharMingen in vitro transcription kit provided in the kit. The reaction contains RNase inhibitor; transcription buffer; 50 ng of the tempate set; 0.1375 mM of each of rGTP, rCTP, rATP; 0.003 mM rUTP;10 mM DTT, 0.010 mCi of [alpha 32P] UTP, and 20 Units of T7 RNA polymerase in a volume of 20 microliters. The reaction mixture is incubated for one hour at 37° C., and then stopped by addition of 2 units of RNAse free DNAse, with an additional incubation of 30 minutes at 37° C. The RNA probes synthesized in this incubation are extracted once with 5.2 mM EDTA, 25 µl of Tris Saturated phenol, 25 µL of chloroform, and 4 µg of yeast tRNA, and then extracted with 50 µL of chloroform. The RNA is precipitated by addition of 50 mL of 4M ammonium acetate and 250 µL of ice-cold 100% ethanol, and after incubation at −80° C. for 30 minutes the preparation is centrifuged at high speed for 30 minutes. The pellet is washed in 100% ethanol, and after removal of the ethanol the probe is resuspended and used in the RNAse protection incubation.

The RNAse protection assay uses the probe material prepared above and RNA extracted from PBMC. The PBMC RNA is washed in 100% ethanol, quantitated by absorbance at 260 nm. The RPA is performed as described in the protocol provided in the PharMingen RiboQuant kit. Eight µL of the PBMC RNA samples are mixed with the 2 μL of the probe set in a thin-walled PCR tube, mixed well, briefly centrifuged and then overlaid with mineral oil. The tube is then placed in a 90° C. PCR block, cooled to 56° C., and incubated for 16 hours. The samples are then cooled to 37° C. and RNAse A and RNAse T1 are added. The mixture is incubated for 45 minutes at 30° C., and the reaction stopped with a mix of protease K and yeast tRNA. The RNA is extracted with phenol-chloroform, and then precipitated from the phenol-chloroform with ammonium acetate-ethanol. The pellet is washed with ethanol and resuspended in buffer for electrophoresis. The samples are analysed by gel electrophoresis by methods well known in molecular biology.

A number of assays may be employed in accordance with the present invention in order to determine the degree of anti-viral activity of a compound of the invention such as cell culture, animal models, and administration to human subjects. The assays described herein may be used to assay viral growth over time to determine the growth characteristics of a virus in the presence of a compound of the invention.

In another embodiment, a virus and a compound of the invention are administered to animal subjects susceptible to infection with the virus. The incidence, severity, length, virus load, mortality rate of infection, etc. can be compared to the incidence, severity, length, virus load, mortality rate of infection, etc. observed when subjects are administered the virus alone (in the absence of a compound of the invention). Anti-virus activity of the compound of the invention is demonstrated by a decrease in incidence, severity, length, virus load, mortality rate of infection, etc. in the presence of the compound of the invention. In a specific embodiment, the virus and the compound of the invention are administered to the animal subject at the same time. In another specific embodiment, the virus is administered to the animal subject before the compound of the invention. In another specific embodiment, the compound of the invention is administered to the animal subject before the virus.

In another embodiment, the growth rate of the virus can be tested by sampling biological fluids/clinical samples (e.g., nasal aspirate, throat swab, sputum, broncho-alveolar lavage, urine, saliva, blood, or serum) from human or animal subjects at multiple time points post-infection either in the presence or absence of a compound of the invention and measuring levels of virus. In specific embodiments, the growth rate of a virus is assayed by assessing the presence of virus in a sample after growth in cell culture, growth on a permissible growth medium, or growth in subject using any method well-known in the art, for example, but not limited to, immunoassay (e.g., ELISA; for discussion regarding ELISAs see, e.g., Ausubel et al., eds, 1994, Current Protocols in Molecular Biology, Vol. I, John Wiley & Sons, Inc., New York at 11.2.1), immunofluorescent staining, or immunoblot analysis using an antibody which immunospecifically recognizes the virus to be assayed or detection of a virus-specific nucleic acid (e.g., by Southern blot or RT-PCR analysis, etc.).

In a specific embodiment, viral titers can be determined by obtaining biological fluids/clinical samples from infected cells or an infected subject, preparing a serial dilution of the sample and infecting a monolayer of cells that are susceptible to infection with the virus (e.g. primary cells, transformed cell lines, patient tissue samples, etc) at a dilution of the virus that allows for the emergence of single plaques. The plaques can then be counted and the viral titer expressed as plaque forming units per milliliter of sample.

In one specific embodiment, the growth rate of a virus in a subject can be estimated by the titer of antibodies against the virus in the subject. Antibody serum titer can be determined by any method well-known in the art, for example, but not limited to, the amount of antibody or antibody fragment in serum samples can be quantitated by, e.g., ELISA.

Additionally, in vivo activity of a TLR7 ligand or prodrug of a TLR7 ligand can be determined by directly administering the compound to a test animal, collecting biological fluids (e.g., nasal aspirate, throat swab, sputum, broncho-alveolar lavage, urine, saliva, blood, or serum) and testing the fluid for anti-virus activity.

In embodiments where samples to be assayed for virus levels are biological fluids/clinical samples (e.g., nasal aspirate, throat swab, sputum, broncho-alveolar lavage, urine, saliva, blood, or serum), the samples may or may not contain intact cells. Samples from subjects containing intact cells can be directly processed, whereas isolates without intact cells may or may not be first cultured on a permissive cell line (e.g. primary cells, transformed cell lines, patient tissue samples, etc) or growth medium (e.g., LB broth/agar, YT broth/agar, blood agar, etc.). Cell suspensions can be cleared by centrifugation at, e.g., 300×g for 5 minutes at room temperature, followed by a PBS, pH 7.4 (Ca++ and Mg++free) wash under the same conditions. Cell pellets can be resuspended in a small volume of PBS for analysis. Primary clinical isolates containing intact cells can be mixed with PBS and centrifuged at 300×g for 5 minutes at room temperature. Mucus is removed from the interface with a sterile pipette tip and cell pellets can be washed once more with PBS under the same conditions. Pellets can then be resuspended in a small volume of PBS for analysis.

In another embodiment, a compound of the invention is administered to a human subject infected with a virus. The incidence, severity, length, viral load, mortality rate of infection, etc. can be compared to the incidence, severity, length, viral load, mortality rate of infection, etc. observed in human subjects infected with a virus in the absence of a compound of the invention or in the presence of a placebo. Anti-viral activity of the compound of the invention is demonstrated by a decrease in incidence, severity, length, viral load, mortality rate of infection, etc. in the presence of the compound of the invention. Any method known in the art can be used to determine anti-viral activity in a subject such as those described previously.

Additionally, in vivo activity of a TLR7 ligand or prodrug of TLR7 ligand can be determined by directly administering the compound to an animal or human subject, collecting biological fluids/clinical samples (e.g., nasal aspirate, throat swab, sputum, broncho-alveolar lavage, urine, saliva, blood, or serum) and testing the biological fluids/clinical samples for anti-viral activity (e.g., by addition to cells in culture in the presence of the virus).

The foregoing has demonstrated the pertinent and important features of the present invention. One of skill in the art will be appreciate that numerous modifications and embodiments may be devised. Therefore, it is intended that the appended claims cover all such modifications and embodiments.

6. EXAMPLES

The following examples are for the purpose of illustration only and are not intended as limiting the scope of the invention.

6.1 TLR7 Ligand Identification

There are three known chemical classes of TLR7 ligands: guanosines, imidazoquinolines, and pyrimidines (see Section 5.2). As described above, additional TLR7 ligands are readily identified by known screening methods. For example, adenine analogs and derivatives were identified as TLR ligands by using the following screening procedure. See Tables 1 and 2.

A stable HEK293-hTLR7 cell line was obtained from Invivogen (San Diego, Calif.), transfected with pNiFty2-Luc, an NF-kB inducible luciferase reporter plasmid (Invivogen) and (dual) stable transfectants selected. The resultant dual (hTLR7/pNiFty2-Luc) cell lines were functionally tested by response to loxoribine and isatoribine as measured by fold luciferase induction relative to a no drug control. The C23 line was chosen due to its satisfactory response and sensitivity profile with these (and other) TLR7 agonists. The biological rationale which connects TLR7 engagement and NF-kB activation has met with widespread acceptance (for a review, see Akira S. et al., *Immunol. Lett.*, 85, 85-95 (2003)) and as a consequence the HEK293-TLR-NF-kB inducible reporter system is accepted as a standard assay which has been consistently used to assay TLR(7) agonists, in either transient or stable system format. See, e.g., Hemmi H. et al., *Nat. Immunol.*, 3, 196-200 (2002); Jurk M. et al., *Nat. Immunol.*, 3, 499 (2002); and Lee J. et al., *Proc. Natl. Acad. Sci. USA*, 100, 6646-51 (2003).

For a typical C23 assay, cells are seeded at $6 \times 10^4$ cells/well in 96 well plates and 4-24 hours later are treated with various concentrations of compound. After 2-48 hours exposure the cell monolayers are lyzed with passive lysis buffer (Promega) and the firefly luciferase assay carried out using the luciferase assay reagent (Promega) as specified by the manufacturer. Relative luciferase activities are expressed as folds of induction compared to the no drug control. A two-fold induction over background is considered a bona fide TLR7 agonist, dependent on this being a statistically significant increase.

TABLE 1

Isatoribine Activates Human TLR7 in HEK293 Assay

| Compound No. | Compound concentration, μM | | | |
|---|---|---|---|---|
| | 50 | 100 | 250 | 500 |
| 21 | 3.1 (±0.2) | 3.4 (±0.1) | 6.2 (±0.5) | 10.9 (±0.7) |

TABLE 2

Adenine Derivative Activates Human TLR7 in HEK293 Assay

| Compound No. | Compound concentration, μM | | | |
|---|---|---|---|---|
| | 1.0 | 3.2 | 10 | 32 |
| 29 | 20.8 (±1.1) | 37.3 (±0.5) | 47.5 (±0.2) | 48.4 (±0.4) |

In Table 1, isatoribine, was added to C23 cells for forty-eight hours, and the cells were then harvested and assayed for luciferase activity. Each time-point was assayed in triplicate. The data displayed is the mean fold induction compared to the no drug control, together with the standard deviation in parentheses.

In Table 2, an adenine derivative 29 was added to C23 cells for twenty-four hours, and the cells were then harvested and assayed for luciferase activity. Each time-point was assayed in triplicate. The data displayed is the mean fold induction compared to the no drug control, together with the standard deviation in parentheses.

6.2 TLR7 Ligands Tested as anti-HCV Agents HCV Viral Load Reduction

Isatoribine investigational drug product was supplied as a 1 mg/mL solution in sterile normal saline contained in a 50 mL vial. Isatoribine was administered in humans by intravenous infusion once daily for 7 days, at 200, 400, 600 or 800 mg per dose. All doses were administered by constant rate infusion over a 60-minute period, except the 800 mg dose was administered over an 80-minute period. The flow rate for each dose was as follows: 3.33 mL/min for the 200 mg dose; 6.67 mL/min for the 400 mg dose; 8.33 mL/min for the 500 mg dose; or 10.0 mL/min for the 600 mg and 800 mg dose.

Four to twelve patients were enrolled in each of the dose groups (200 mg, 400 mg, 600 mg and 800 mg per dose) and received once daily intravenous infusions for 7 days. Prior to dosing, a blood sample was drawn from each patient for assessment of the genotype of the HCV virus.

Plasma HCV RNA was determined at baseline (an average of 2 pre-treatment measurements taken on Day -1 or pre-treatment and on Day 1) and once daily prior to the start of the first daily isatoribine intravenous infusion on Days 2 through 7 for these daily (×7 days) dosing groups. See FIG. 2. The viral load was measured by the branched DNA method (Versant™ v3.0 bDNA assay, Bayer Diagnostics). For plasma HCV RNA, the maximum change from the pre-treatment baseline was estimated using log-transformed values.

Figure 2:
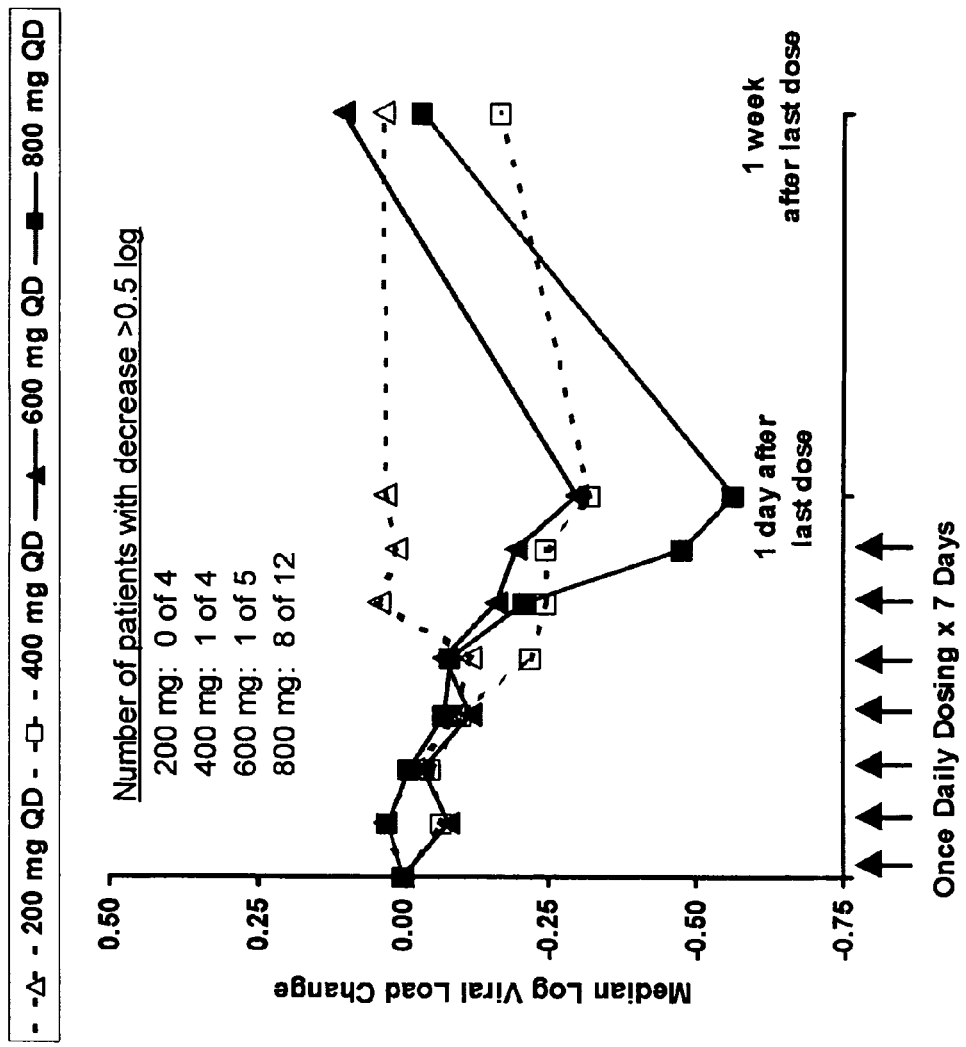
FIG. 2 is a graphical depiction of Viral Load Changes in HCV infected Patients receiving isatoribine.

Plasma HCV RNA decreased over the course of isatoribine treatment, with the larger changes generally occurring in patients who received the higher daily doses (FIG. 2). Eight of 12 patients who received isatoribine 800 mg QD×7 days showed a plasma viral load decrease of more than 0.5 log 10 units, with a mean change in these 12 patients of −0.76 log 10 units and range of −2.85 to +0.21 log 10 units. This decrease in viral load was statistically significant for the 800 mg QD dose group (p=0.008). Plasma viral load declines generally reversed upon cessation of treatment.

HCV Replicon-Based Viral Bioassay

It has been demonstrated that HCV replicons are highly sensitive to the inhibitory effects of interferon-α and interferon-γ. Therefore the HCV replicon becomes a very useful system for measuring the amount of biologically active interferons in supernatants from human PBMCs stimulated with a TLR7 agonist. A quantitative assay was developed which is based on measuring the activity of the luciferase reporter gene that was integrated into an HCV replicon. By using this system, interferons from TLR7 agonist-treated PBMCs were measured and their inhibitory activity was assessed using the luciferase reporter replicon.

Human PBMCs isolated from a healthy donor were placed in replicate cell culture wells ($5 \times 10^6$ cells per well). The PBMCs are incubated in the absence of test compounds at 37° C. in a humidified atmosphere containing 5% $CO_2$ for 24 hours to allow stabilization to the culture conditions, and then the TLR7 ligand or a drug free control is added to replicate wells containing PBMCs from the same donor. The concentrations of TLR7 ligand may be varied to suit the particular experiment, and the PBMC cultures are then incubated at 37° C. in a humidified atmosphere containing 5% $CO_2$ for eight hours. Samples of cell culture supernatant are taken at the eight hour time point (or twenty four hour time point in case of Loxoribine and its prodrugs) from TLR7 ligand treated and control wells and are assayed for interferon-alpha production by ELISA. Supernatants from compound-treated cells and a no-drug control were diluted at 1:10, 1:100, and 1:1000 in RPMI media and applied to a 96-well plate of Huh7 hepatocyte cells containing the luciferase reporter replicon. Cells were incubated for 48 hours at 37° C. in a tissue culture incubator.

After the incubation period, the 96-well plates are washed 2× with PBS and are lysed with passive lysis buffer (Promega). Plates are shaken at room temperature for 20 minutes and standard luciferase assay reagent (Promega) is added to each well by injection and the plate is read on an Lmax luminometer (Molecular Devices). The raw relative light units are converted to a percent inhibition that is compared to the no-drug control wells to determine the level of inhibition observed in the replicon assay. The estimated maximal concentration of interferons required to inhibit HCV replicon replication was determined to be at a 1:10 dilution of supernatant of PBMC-stimulated cells which fell within our test range of the dilution series. For all TLR7 agonists tested, 100% inhibition was observed on the luciferase reporter replicon system at the 1:10 dilution.

The data presented in Tables 3-8 represents the inhibition of the HCV replicon system by the supernatant collected after exposure of PBMC cells to the compound at an initial concentration for the incubation time indicated and diluted as specified in the first column ("PBMC exposed to compound"). A supernatant collected from PBMC cells non-exposed to the compound and diluted as specified in the first column was used as a control ("Blank supernatant"). The PBMC cells were isolated from a single blood donor as specified.

TABLE 3

Antiviral Effect of Isatoribine in the in vitro HCV Replicon Bioassay

No. 1
Incubation time: 8 hours
Initial concentration: 100 μM
Blood donor number: FL72035

| Dilution of supernatant | HCV replicon inhibition, % | |
|---|---|---|
| | Blank PBMC | PBMC exposed to compound |
| 1:100 | 0 | 100 |
| 1:1000 | 0 | 94 |

No. 2
Incubation time: 8 hours
Initial concentration: 100 μM
Blood donor number: FL75287

| Dilution of supernatant | HCV replicon inhibition, % | |
|---|---|---|
| | Blank PBMC | PBMC exposed to compound |
| 1:10 | 0 | 100 |
| 1:100 | 0 | 87 |
| 1:1000 | 0 | 6 |

No. 3
Incubation time: 24 hours
Initial concentration: 100 μM
Blood donor number: FL75864

| Dilution of supernatant | HCV replicon inhibition, % | |
|---|---|---|
| | Blank PBMC | PBMC exposed to compound |
| 1:10 | 0 | 100 |
| 1:100 | 23 | 99 |
| 1:1000 | 0 | 64 |

TABLE 4

Antiviral Effect of Loxoribine in the in vitro HCV Replicon Bioassay

No. 1
Incubation time: 24 hours
Initial concentration: 100 μM
Blood donor number: FL75864

| Dilution of supernatant | HCV replicon inhibition, % | |
|---|---|---|
| | Blank PBMC | PBMC exposed to compound |
| 1:10 | 0 | 100 |
| 1:100 | 23 | 74 |
| 1:1000 | 0 | 17 |

TABLE 5

Antiviral Effect of Imiquimod in the in vitro HCV Replicon Bioassay

No. 1
Incubation time: 8 hours
Initial concentration: 3.2 μM
Blood donor number: FL75287

| Dilution of supernatant | HCV replicon inhibition, % | |
|---|---|---|
| | Blank PBMC | PBMC exposed to compound |
| 1:10 | 0 | 100 |
| 1:100 | 0 | 100 |
| 1:1000 | 0 | 89 |

No. 2
Incubation time: 8 hours
Initial concentration: 3.2 μM
Blood donor number: FL75287

| Dilution of supernatant | HCV replicon inhibition, % | |
|---|---|---|
| | Blank PBMC | PBMC exposed to compound |
| 1:10 | 3 | 100 |
| 1:100 | 13 | 75 |
| 1:1000 | 3 | 1 |

TABLE 6

Antiviral Effect of Resiquimod in the in vitro HCV Replicon Bioassay

No. 1
Incubation time: 8 hours
Initial concentration: 10 μM
Blood donor number: FL75287

| Dilution of supernatant | HCV replicon inhibition, % | |
|---|---|---|
| | Blank PBMC | PBMC exposed to compound |
| 1:10 | 0 | 100 |
| 1:100 | 0 | 98 |
| 1:1000 | 0 | 21 |

TABLE 6-continued

Antiviral Effect of Resiquimod in
the in vitro HCV Replicon Bioassay

No. 2
Incubation time: 8 hours
Initial concentration: 10 µM
Blood donor number: FL75287

| Dilution of supernatant | HCV replicon inhibition, % | |
|---|---|---|
| | Blank PBMC | PBMC exposed to compound |
| 1:10 | 3 | 100 |
| 1:100 | 13 | 88 |
| 1:1000 | 3 | 6 |

TABLE 7

Antiviral Effect of Bropirimine in
the in vitro HCV Replicon Bioassay

No. 1
Incubation time: 8 hours
Initial concentration: 100 µM
Blood donor number: FL72035

| Dilution of supernatant | HCV replicon inhibition, % | |
|---|---|---|
| | Blank PBMC | PBMC exposed to compound |
| 1:10 | 0 | 100 |
| 1:100 | 0 | 95 |
| 1:1000 | 0 | 0 |

No. 2
Incubation time: 8 hours
Initial concentration: 100 µM
Blood donor number: FL72036

| Dilution of supernatant | HCV replicon inhibition, % | |
|---|---|---|
| | Blank PBMC | PBMC exposed to compound |
| 1:10 | 0 | 100 |
| 1:100 | 8 | 95 |
| 1:1000 | 0 | 33 |

TABLE 8

Antiviral Effect of Adenine Derivative
in the in vitro HCV Replicon Bioassay

No. 1
Incubation time: 8 hours
Initial concentration: 0.1 µM
Blood donor number: FL76418
Form of the compound: a TFA salt

| Dilution of supernatant | HCV replicon inhibition, % | |
|---|---|---|
| | Blank PBMC | PBMC exposed to compound |
| 1:10 | 0 | 100 |
| 1:100 | 3 | 73 |
| 1:1000 | 3 | 0 |

TABLE 8-continued

Antiviral Effect of Adenine Derivative
in the in vitro HCV Replicon Bioassay

No. 2
Incubation time: 8 hours
Initial concentration: 0.1 µM
Blood donor number: FL76418
Form of the compound: a TFA salt

| Dilution of supernatant | HCV replicon inhibition, % | |
|---|---|---|
| | Blank PBMC | PBMC exposed to compound |
| 1:10 | 0 | 100 |
| 1:100 | 3 | 64 |
| 1:1000 | 3 | 9 |

6.3 Preparation of TLR7 Ligand Prodrugs

Compounds of the invention can be synthesized using the methodology described in Schemes 1-18 above. Unless otherwise indicated all temperatures are set forth in degrees Celsius and all parts and percentages are by weight. Reagents are purchased from commercial suppliers such as Aldrich Chemical Company or Lancaster Synthesis Ltd. and are used without further purification unless otherwise indicated. Tetrahydrofuran (THF) and N,N-dimethylforamide (DMF) are purchased from Aldrich in Sure Seal bottles and used as received. Unless otherwise indicated, the following solvents and reagents are distilled under a blanket of dry nitrogen. THF and $Et_2O$ are distilled from Na-benzophenone ketyl; $CH_2Cl_2$ (DCM), diisopropylamine, pyridine and $Et_3N$ are distilled from $CaH_2$; MeCN is distilled first from $P_2O_5$, then from $CaH_2$; MeOH is distilled from Mg; PhMe, EtOAc and i-PrOAc are distilled from $CaH_2$; TFAA was purified via simple atmospheric distillation under dry argon.

The reactions set forth are done generally under a positive pressure of argon at an ambient temperature (unless otherwise stated) in anhydrous solvents, and the reaction flasks are fitted with rubber septa for the introduction of substrates and reagents via syringe. Glassware is oven dried and/or heat dried. The reactions are assayed by TLC and terminated as judged by the consumption of starting material. Analytical thin layer chromatography (TLC) is performed on aluminum-backed silica gel 60 F254 0.2 mm plates (EM Science), and visualized with UV light (254 nm) followed by heating with commercial ethanolic phosphomolybdic acid. Preparative thin layer chromatography (TLC) is performed on aluminum-backed silica gel 60 F254 1.0 mm plates (EM Science) and visualized with UV light (254 nm). HPLC is performed on a Waters Micromass ZQ system consisting of a model 2525 binary gradient pump with an Alltech model 800 ELSD detector and a Waters model 996 photodiode array detector.

Work-ups are typically done by doubling the reaction volume with the reaction solvent or extraction solvent and then washing with the indicated aqueous solutions using 25% by volume of the extraction volume unless otherwise indicated. Product solutions are dried over anhydrous $Na_2SO_4$ and/or $Mg_2SO_4$ prior to filtration and evaporation of the solvents under reduced pressure on a rotary evaporator and noted as solvents removed in vacuo. Column chromatography is completed under positive pressure using 230-400 mesh silica gel or 50-200 mesh neutral alumina. Hydrogenolysis is done at the pressure indicated in the examples or at ambient pressure.

$^1$H-NMR spectra is recorded on a Varian Mercury-VX400 instrument operating at 400 MHz and $^{13}$C-NMR spectra are recorded operating at 75 MHz. NMR spectra are obtained as CDCl₃ solutions (reported in ppm), using chloroform as the reference standard (7.27 ppm and 77.00 ppm), CD₃OD (3.4 and 4.8 ppm and 49.3 ppm), DMSO-d₆, or internally tetramethylsilane (0.00 ppm) when appropriate. Other NMR solvents are used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Infrared (IR) spectra are recorded on a Thermo Nicolet Avatar 370 FT-IR as neat oils or solids, and when given are reported in wave numbers (cm⁻¹). Mass spectra reported (+)-ES Thermo Finnegan LCQ LC/MS conducted by the Analytical Chemistry Department at Anadys Pharmaceuticals, Inc. Elemental analyses are conducted by the Atlantic Microlab, Inc. in Norcross, Ga. or by NuMega, in San Diego, Calif. Melting points (mp) are determined on an open capillary apparatus, and are uncorrected.

The described synthetic pathways and experimental procedures utilize many common chemical abbreviations, THF (tetrahydrofuran), DMF (N,N-dimethylformamide), EtOAc (ethyl acetate), DMSO (dimethyl sulfoxide), DMAP (4-dimethylaminopyridine), DBU (1,8-diazacyclo[5.4.0]undec-7-ene), DCM (4-(dicyanomethylene)-2-methyl-6-(4-dimethylamino-styryl)-4-H-pyran), MCPBA (3-chloroperoxybenzoic acid), EDC (1-(3-dimethylaminopropyl)-3-ethylcarbodiimide hydrochloride), HATU (O-(7-azabenzotriazol-1-yl)-1,1,3,3-tetramethyluronium hexafluorophosphate), HOBT (1-hydroxybenzotriazole hydrate), TFAA (trifluoroacetic anhydride), pyBOP (benzotriazol-1-yloxy)tripyrrolidinophosphonium hexafluorophosphate), DIEA (diisopropylethylamine), and the like.

Example 1

7-Allyl-2-amino-9-β-D-ribofuranosyl-7,9-dihydropurin-8-one (43)

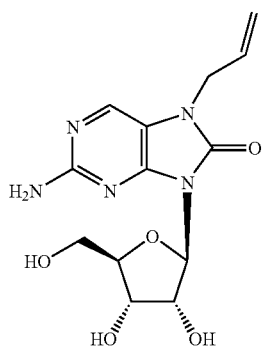

Step 1: Preparation of 7-Allyl-2-amino-9-(2',3',5'-tri-O-acetyl-β-D-ribofuranosyl)-7,9-dihydro-1H-purine-6,8-dione (40)

A heterogeneous mixture of 7-allyl-2-amino-9-β-D-ribofuranosyl-7,9-dihydro-1H-purine-6,8-dione 17 (1.00 g, 2.95 mmol, prepared according to Reitz et al., *JMC*, 37, 3561-3578 (1994)), DMAP (0.036 mg, 0.29 mmol) and NEt₃ (2.05 mL, 14.74 mmol) was stirred in dry acetonitrile (25 mL). Acetic anhydride (0.862 mL, 9.13 mmol) was added slowly to the suspension and the reaction mixture was stirred at ambient temperature for 16 h. The solvent was removed under vacuum and the residue dissolved in dichloromethane (DCM). The organic phase was then washed with saturated aqueous sodium bicarbonate (NaHCO₃), brine and thereafter dried with anhydrous magnesium sulfate (MgSO₄). The solvent was concentrated under vacuum and dried at room temperature under high vacuum to give 1.33 g of 40 (97%) as a pale yellow solid: ¹H NMR (400 MHz, CDCl₃) δ 6.12 (t, J=6.0 Hz, 1H), 6.01 (d, J=3.6 Hz, 1H), 5.89 (m, 1H), 5.82 (t, J=6.0 Hz, 1H), 5.39 (br s, 2H), 5.21 (m, 2H), 4.58 (br s, 2H), 4.51 (m, 1H), 4.32 (m, 2H), 2.16 (s, 3H), 2.15 (s, 3H), 2.10 (s, 3H); MS (+)-ES [M+H]⁺ 466.2 m/z.

Step 2: Preparation of 7-Allyl-2-amino-6-chloro-9-(2',3',5'-tri-O-acetyl-β-D-ribofuranosyl)-7,9-dihydropurin-8-one (41)

Compound 40 (0.65 g, 1.39 mmol) was dissolved in phosphorus oxychloride (10 mL) and heated to 75° C. for 16 h. The reaction mixture was concentrated under vacuum and the crude product dissolved in DCM. The mixture was then washed with NaHCO₃ solution, brine, dried (MgSO4) and filtered. The filtrate was concentrated under vacuum and purified by flash chromatography using 10 to 50% gradient of ethyl acetate in hexanes. Removal of the solvent afforded 280 mg (41%) of the desired product 41: ¹H NMR (400 MHz, CDCl₃) δ 6.04 (d, J=4.0 Hz, 1H), 6.03 (t, J=5.6 Hz, 1H), 5.87 (m, 1H), 5.86 (t, J=5.6 Hz, 1H), 5.18 (m, 4H), 4.59 (d, J=8.0 Hz, 2H), 4.45 (d, J=7.6 Hz, 1H), 4.31 (m, 2H), 2.10 (s, 3H), 2.08 (s, 3H), 2.04 (s, 3H); MS (+)-ES [M+H]⁺ 484.2 m/z.

Step 3: Preparation of 7-Allyl-2-amino-9-(2',3',5'-tri-O-acetyl-β-D-ribofuranosyl)-7,9-dihydro-purin-8-one (42)

Compound 41 (0.27 g, 0.56 mmol) was dissolved in acetic acid and Zn—Cu couple was added to the solution. The mixture was heated at 70° C. for 18 h. The suspended particles were filtered off and the filtrate concentrated under vacuum. The residue was purified by flash chromatography using 10% to 100% gradient of ethyl acetate in hexanes. The solvent was removed to give 150 mg (60%) of 42 as off-white solid: ¹H NMR (400 MHz, CDCl₃) δ 6.05 (t, J=4.0 Hz, 1H), 6.03 (d, J=4.0 Hz, 1H), 5.87 (t, J=6.0 Hz, 1H), 5.83 (m, 1H), 5.48 (br s, 2H), 5.33 (s, 1H), 5.29 (d, J=5.6 Hz, 1H), 4.49 (d, J=3.2 Hz, 1H), 4.46 (d, J=3.2 Hz, 1H), 4.41 (d, J=5.6 Hz, 2H), 4.27 (m, 2H), 2.12 (s, 3H), 2.10 (s, 3H), 2.05 (s, 3H); MS (+)-ES [M+H]+ 450.0 m/z.

Step 4: Preparation of 7-Allyl-2-amino-9-D-β-ribofuranosyl-7,9-dihydro-purin-8-one (43)

To a solution of 42 (0.13 g, 0.29 mmol) in methanol (4 mL) was added solid K₂CO₃ (0.024 g, 0.17 mmol) and the reaction stirred at ambient temperature for 18 h. To the cloudy mixture was added Amberlite CG-50 (0.5 g) and stirred till neutral and filtered. The filtrate was concentrated to give an off-white solid, which was washed with water and dried under high vacuum to give 93.5 mg of pure 43 in quantitative yield as an off white solid: ¹H NMR (400 MHz, d₆-DMSO) δ 7.88 (s, 1H), 6.33 (br s, 2H), 5.85 (m, 1H), 5.66 (d, J=6.0 Hz, 1H), 5.30 (d, J=5.6 Hz, 1H), 5.20 (s, 1H), 5.16 (d, J=8.4 Hz, 1H), 5.01 (d, J=4.8 Hz, 1H), 4.89 (q, J=5.6 Hz, 1H), 4.75 (br s, 1H), 4.35 (d, J=5.2 Hz, 2H), 4.10 (t, J=8.4 Hz, 1) 3.80 (q, J=3.6 Hz, 1H), 3.57 (m, 1H), 3.44 (m, 1H). MS (+)-ES [M+H]+ 324.1 m/z.

Example 2

7-Allyl-2-amino-6-ethoxy-9-β-D-ribofuranosyl-7,9-dihydro-purin-8-one (45)

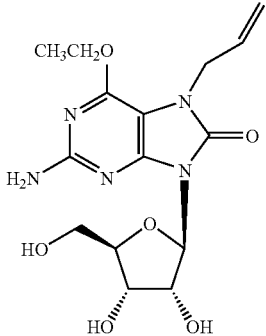

Step 1: Preparation of 7-Allyl-2-amino-6-ethoxy-9-(2′,3′,5′-tri-O-acetyl-β-D-ribofuranosyl)-7,9-dihydro-purin-8-one (44)

To a solution of 40 (0.30 g, 0.64 mmol) in dry THF (15 mL) was added polymer-supported triphenylphosphine (0.89 g, 1.93 mmol) and EtOH (0.11 mL, 1.93 mmol) at room temperature. To the stirring mixture was added diethyl azodicarboxylate (0.12 mL, 0.77 mmol) and stirring continued for 18 h. The spent polymer support was filtered off and the solvent removed under vacuum. The residue was then purified by flash chromatography using 10 to 50% gradient of ethyl acetate in hexanes. Removal of the solvent afforded 85 mg (26%) of the desired product 6 as a clear oil: $^1$H NMR (400 MHz, CDCl$_3$) δ 6.07 (d, J=4.0 Hz, 1H), 6.06 (d, J=4.0 Hz, 1H), 6.01 (d, J=3.6 Hz, 1H), 5.96 (t, J=6.0 Hz, 1H), 5.87 (m, 1H), 5.14 (d, J=2.2 Hz, 1H), 5.15 (m, 1H), 4.80 (br s, 2H), 4.46 (m, 4H), 4.37 (q, J=7.2 Hz, 2H), 4.29 (m, 2H), 2.09 (s, 3H), 2.08 (s, 3H), 2.04 (s, 3H); 1.35 (t, J=7.6 Hz, 3H); MS (+)-ES [M+H]+ 494.1 m/z.

Step 2: Preparation of 7-Allyl-2-amino-6-ethoxy-9-β-D-ribofuranosyl-7,9-dihydro-purin-8-one (45)

To a solution of 44 (0.084 g, 0.17 mmol) in methanol (4 mL) was added solid K$_2$CO$_3$ (0.014 g, 0.17 mmol) and the reaction stirred at ambient temperature for 1 h. To the cloudy mixture was added Amberlite CG-50 (0.5 g) and stirred till neutral and filtered. The filtrate was concentrated and purified by flash chromatography using 100% DCM to 10% of methanol in DCM. Removal of the solvent afforded 62 mg of 7 (99%) as a clear oil:

$^1$H NMR (400 MHz, CDCl$_3$) δ 5.97 (d, J=8.0 Hz, 1H), 5.93 (m, 1H), 5.25 (d, J=32.4, Hz, 1H), 5.21 (s, 1H), 5.02 (t, J=8.0 Hz, 1H), 4.62 (br s, 2H), 4.47 (d, J=5.6 Hz, 2H), 4.25-4.45 (m, 3H), 4.21 (q, J=6.8 Hz, 2H), 3.77 (ABq, Δυ$_{AB}$=0.14, J$_{AB}$=12.4 Hz, 2H), 1.37 (t, J=6.8 Hz, 3H), 1.27 (t, 7.6, 2H); MS (+)-ES [M+H]+ 368.0 m/z.

Example 3

5-Bromo-4-ethoxy-6-phenyl-pyrimidin-2-ylamine (37)

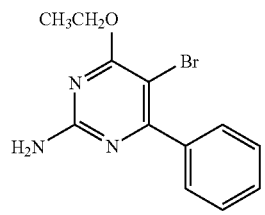

Step 1: Preparation of 5-Bromo-4-ethoxy-6-phenyl-pyrimidin-2-ylamine (37)

In a manner similar to step 2 of Example 2 was prepared the title compound as a white solid from 2-amino-5-bromo-6-phenyl-3H-pyrimidin-4-one 35 (Wierenga, et al., JMC, 23, 239-240 (1980)) in 13% yield: $^1$H NMR (400 MHz, CDCl$_3$) δ 7.61 (m, 2H0, 7.42 (m, 3H), 5.15 (br s, 2H), 4.23 (q, J=7.2 Hz, 2H), 1.44 (t, 6.8 Hz, 3H); MS (+)-ES [M]+ 294.1 [M+2]+296.0 m/z. Elemental analysis for C$_{12}$H$_{12}$BrN$_3$O: calc'd: C, 49.00; H, 4.11; N, 14.29; found: C, 48.94; H, 4.18; N, 14.01.

Example 4

4-(2-Amino-5-bromo-6-phenyl-pyrimidin-4-yloxymethyl)-5-methyl-[1,3]dioxol-2-one (46)

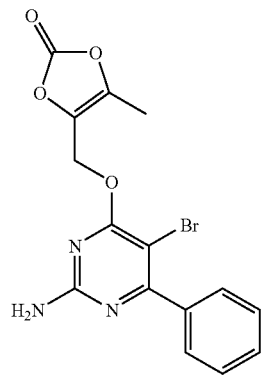

Step 1: Preparation of 4-(2-Amino-5-bromo-6-phenyl-pyrimidin-4-yloxymethyl)-5-methyl-[1,3]dioxol-2-one (46)

In a manner similar to step 2 of Example 2 was prepared the title compound as a white solid from 2-Amino-5-bromo-6-phenyl-3H-pyrimidin-4-one 35 in 4% yield: $^1$H NMR (400 MHz, CDCl$_3$) δ 7.62 (m, 2H), 7.45 (m, 3H), 5.18 (s, 2H), 5.07

(s, 2H), 2.26 (s, H); MS(+)-ES [M]+378.2 [M+2]+ 380.1 m/z. Elemental analysis for C₁₅H₁₂BrN₃O₄: calc'd: C, 47.64; H, 3.20; N, 11.11; found: C, 46.98; H, 3.23; N, 10.70.

Example 5

5-Bromo-4-phenyl-pyrimidin-2-ylamine (48)

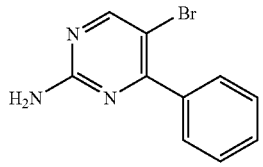

Step 1: Preparation of 4-Phenyl-pyrimidin-2-ylamine (47)

To a solution of bromobenzene (4.43 mL, 42.06 mmol) in dry THF (100 mL) at −78° C. was added BuLi (394 mL, 63.08 mmol) and the mixture left to stir at −78° C. for 2 h. To this was added 2-aminopyrimidine (2.0 g, 21.03 mmol) in hot toluene (80 mL) over a 15 minutes period. The mixture was refluxed for 16 h and allowed to cool to room temperature and carefully quenched with aqueous NaHCO₃. The mixture was filtered and the filtrate concentrated under vacuum. The residue was then dissolved in DCM and washed with aqueous NaHCO₃, brine and dried (MgSO4). The solvent was removed to afford 350 mg of 47 (10%) as a pale yellow solid: ¹H NMR (400 MHz, CDCl₃) δ 8.32 (d, J=4.8 Hz, 1H), 7.97 (m, 2H), 7.45 (m, 3H), 7.02 (J=4.8 Hz, 1H). 5.27 (br s, 2H); MS (+)-ES [M+H]+ 172.2 m/z.

Step 2: Preparation of 5-Bromo-4-phenyl-pyrimidin-2-ylamine (48)

Compound 47 (0.30 g, 1.75 mmol) was dissolved in glacial acetic acid (15 ml) and warmed to 45° C. Br₂ (0.09 mL, 1.75 mmol) was added slowly. The resulting mixture was then allowed to stir at room temperature for 3 h. The solvent was removed under vacuum to a solid residue. This was then transferred onto a filter funnel and washed with DCM, followed by water. The remaining solid was then dried under high vacuum for 16 h to give 197 mg of 13 (45%) as a pale yellow solid: ¹H NMR (400 MHz, d₆-DMSO) δ 8.40 (s, 1H), 7.61 (m, 2H), 7.45 (m, 3H), 6.96 (s, 2H); MS (+)-ES [M]+ 250.0 [M+2]+ 252.0 m/z. Elemental analysis for C₁₀H₈BrN₃: calc'd: C, 48.02; H, 3.22; Br, 31.95; N, 16.80; found: C, 47.91; H, 3.28; Br, 32.15; N, 16.80.

Example 6

(5-Bromo-6-oxo-4-phenyl-1,6-dihydro-pyrimidin-2-yl)-carbamic acid ethyl ester (36)

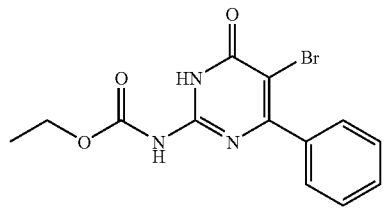

Step 1: Preparation of (5-Bromo-6-oxo-4-phenyl-1,6-dihydro-pyrimidin-2-yl)-carbamic acid ethyl ester (36)

To a solution of 35 (0.25 g, 0.94 mmol) in DMF (8 mL) was added NEt₃ (0.14 mL, 0.99 mmol) and diethyl pyrocarbonate (0.27 mL, 1.89 mmol). The reaction mixture was maintained at 65° C. for 20 h. The solvent was removed and the residue treated with DCM. The resulting mixture was filtered to remove the remaining starting material 35 and the filtrate washed with aqueous NaHCO₃, brine and dried (MgSO₄). The filtrate was concentrated and purified by HPLC (Thomson ODS-A 100A 5 μ150×21.2 mm column; flow rate=30 mL/min; CH₃CN with 0.05% TFA (A), Water with 0.05% TFA (B); Make up pump flow=0.9 mL/min; Make up pump mobile phase; MeOH with 0.05% TFA using a gradient system as follows: t=0; 15% A, 85% B; t=3.0 min; 15% A, 85% B; t=9.5 min; 70% A, 30% B; t=10.0 min; 100% A, 0% B; t=12.0 min; 100% A, 0% B; t=12.5 min; 15% A, 85% B; t=15.0 min; 15% A, 85% B.) to afford 54 mgs of 36 (17%) as a clear oil: ¹H NMR (400 MHz, CDCl₃) δ 7.66 (m, 1H), 7.44 (m, 3H), 4.26 (q, J=7.6 Hz, 2H), 1.32 t, J=6.8 Hz, 3H); MS (+)- ES [M]+ 338.1 [M+2]+ 340.0 m/z. Elemental analysis for C₁₃H₁₂BrN₃O₃: calc'd: C, 46.17; H, 3.58; N, 12.43; found: C, 46.43; H, 3.74; N, 11.95.

Example 7

(5-Bromo-6-oxo-4-phenyl-1,6-dihydro-pyrimidin-2-yl)-carbamic acid pentyl ester (49)

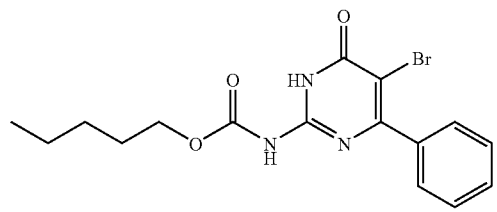

Step 1: Preparation of (5-Bromo-6-oxo-4-phenyl-1,6-dihydro-pyrimidin-2-yl)-carbamic acid pentyl ester (49)

In a manner similar to step 1 of Example 6 the title compound was prepared from 35 and dipentyl pyrocarbonate as a clear oil in 9% yield after HPLC purification (Thomson ODS-A 100A 5μ 150×21.2 mm column; flow rate=30 mL/min; CH₃CN with 0.05% TFA (A), Water with 0.05% TFA (B); Make up pump flow=0.9 mL/min; Make up pump mobile phase; MeOH with 0.05% TFA using a gradient system as follows: t=0; 35% A, 65% B; t=3.0 min; 35% A, 65% B; t=10 min; 100% A, 0% B; t=12.0 min; 100% A, 0% B; t=12.5 min; 35% A, 65% B; t=15.0 min; 35% A, 65% B.). ¹HNMR (400 MHz, CDCl₃) δ 7.69 (br s, 1H), 7.67 (m, 2H), 7.43 (d, J=2.0 Hz, 3H), 4.17 (t, J=7.2 Hz, 2H), 1.64 (t, J=6.8 Hz, 2H), 1.34 (m, 4H), 0.92 (t, J=6.4 Hz, 3H); MS (+)-ES [M]+ 380.1 [M+2]+ 382.1 m/z.

Example 8

(1-Isobutyl-1H-imidazo[4,5-c]quinolin-4-yl)-carbamic acid pentyl ester (34)

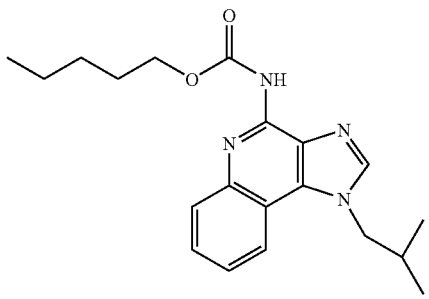

Step 1: Preparation of (1-Isobutyl-1H-imidazo[4,5-c]quinolin-4-yl)-carbamic acid pentyl ester (34)

To a suspension of 1-Isobutyl-1H-imidazo[4,5-c]quinolin-4-ylamine 31 (0.15 g, 0.62 mmol, prepared according to the procedure given in WO94/17043) in CHCl$_3$ (5 mL) was added NEt$_3$ (0.09 mL, 0.65 mmol) and dipentyl pyrocarbonate (0.231 g, 0.94 mmol). The mixture was stirred at 40° C. for 60 h. The reaction mixture was washed with aqueous NaHCO$_3$, brine and dried over MgSO$_4$. The filtrate was concentrated and purified by flash chromatography using a 10% to 70% gradient of ethyl acetate in hexanes to give 50.5 mg of 34 (23%) as a white solid: $^1$H NMR (400 MHz, CDCl$_3$) δ 8.31 (br s, 1H), 8.15 (t, J=8.0 Hz, 2H), 7.85 (t, J=7.2 Hz, 1H), 7.77 (t, J=8.0 Hz, 1H), 4.43 (d, J=7.6 Hz, 2H), 4.36 (t, J=7.2 Hz, 2H), 2.31 (m, 1H), 1.75 (t, J=6.8 Hz, 2H), 1.36 (m, 4H), 1.06 (d, J=6.4 Hz, 6H), 0.89 (t, J=6.8 Hz, 2H); MS (+)-ES [M+H]$^+$ 355.3 m/z.

Example 9

(1-Isobutyl-1H-imidazo[4,5-c]quinolin-4-yl)-carbamic acid ethyl ester (50)

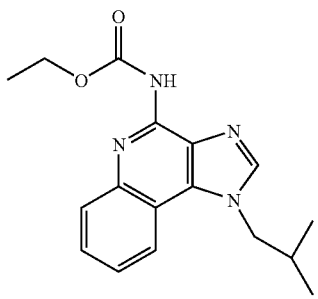

Step 1: Preparation of (1-Isobutyl-1H-imidazo[4,5-c]quinolin-4-yl)-carbamic acid ethyl ester (50)

In a manner similar to step 1 of Example 8 was prepared the title compound as a white solid from 31 and diethyl pyrocarbonate in 67% yield as a white solid: $^1$H NMR (400 MHz, CDCl$_3$) δ 9.32 (br s, 2H), 8.2 (d, J=8.0 Hz, 2H) 8.12 (d, J=8.0 Hz, 1H), 7.83 (t, J=7.2 Hz, 1H), 7.74 (t, J=8.0 Hz,1H) 4.43 (m, 4H), 2.35 (m, 1H), 1.39 (t, J=7.2 Hz, 3H), 1.08 (d, J=6.4 Hz, 6H); MS (+)- ES [M+H]$^+$ 313.2 m/z.

Example 10

Carbonic acid 6-amino-9-benzyl-2-(2-methoxy-ethoxy)-9H-purin-8-yl ester ethyl ester (51)

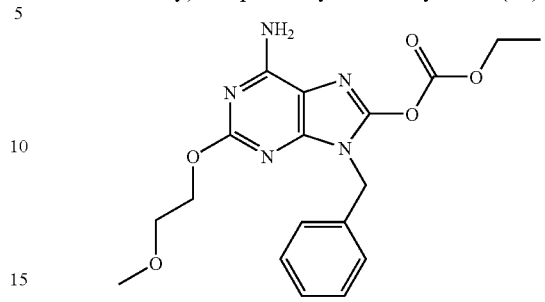

Step 1: Preparation of Carbonic acid 6-amino-9-benzyl-2-(2-methoxy-ethoxy)-9H-purin-8-yl ester ethyl ester (51)

6-Amino-9-benzyl-2-(2-methoxy-ethoxy)-9H-purin-8-ol, 29 (11.75 mg, 0.027 mmol, prepared according to the procedure described by Kurimota, et al., *Bioorg. Med. Chem.*, 12, 1091-109 (2004) was suspended in CH$_2$Cl$_2$ (0.6 mL) and cooled to 0° C. DIEA (11.96 μL, 0.068 mmol) and ethyl chloroformate (3.86 mg, 0.036 mmol, added as a 10% by volume solution in dichloromethane) were then added to the suspension. The reaction mixture was stirred at 0° C. for 10 minutes then allowed to warm to room temperature for 15 minutes. TLC of the reaction mixture shows that starting material remained. The reaction mixture was heated to 35° C., DMAP (cat.), methanol (60 μL portions) was added to dissolve 29, and additional aliquots of ethyl chloroformate (3.86 mg, 0.036 mmol, added as a 10% by volume solution in dichloromethane) were added until the reactions was complete. The crude mixture was purified by flash chromatography using a 0 to 100% gradient of ethyl acetate in hexane. The desired peaks were collected and concentrated in-vacuo to yield 8.5 mg (80%) of compound 51 as a white solid: $^1$H NMR (400 MHz, CDCl$_3$) δ 7.45 (d, J=Hz, 2H), 7.27 (m, 3H), 4.98 (s, 2H), 4.46 (m, 4H), 3.74 (m, 2H), 3.42 (s, 2H), 1.46 (t, 3H); MS [M+H]+ m/z 388.3.

Examples 11-20 were prepared from 6-amino-9-benzyl-2-(2-methoxy-ethoxy)-9H-purin-8-ol, 29 and the appropriate chloroformate according to the procedure described in Example 10.

Example 11

Carbonic acid 6-amino-9-benzyl-2-(2-methoxy-ethoxy)-9H-purin-8-yl ester propyl ester (52)

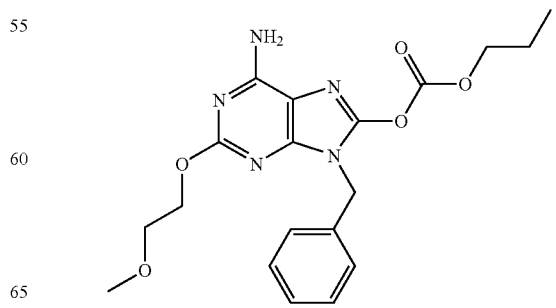

86% yield as a white solid: $^1$H NMR (400 MHz, CDCl$_3$) δ 7.45 (d, J=6.4 Hz, 2H), 7.27 (m, 3H), 4.98 (s, 2H), 4.46 (m, 4H), 3.74 (t, J=5.2 Hz, 2H), 3.42 (s, 3H), 1.46 (t, J=7.6 Hz, 3H); MS [M+H]$^+$ m/z 402.2.

Example 12

Carbonic acid 6-amino-9-benzyl-2-(2-methoxy-ethoxy)-9H-purin-8-yl ester isobutyl ester (53)

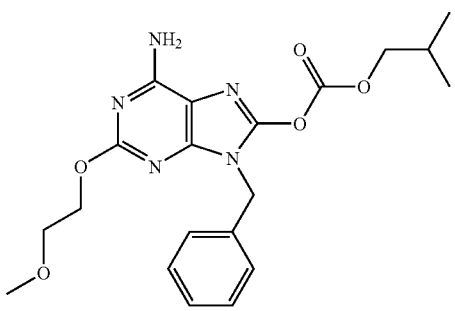

92% yield as a white solid: $^1$H NMR (400 MHz, CDCl$_3$) δ 7.45 (d, J=6.4 Hz 2H), 7.27 (m, 3H), 4.99 (s, 2H), 4.45 (m, 2H), 4.17 (d, J=7.4 Hz, 2H), 3.73 (t, J=4.8 Hz, 2H), 3.4 (s, 3H), 2.15 (m, 1H), 1.06 (d, J=6.8 Hz, 6H); MS [M+H]+m/z 416.3.

Example 13

Carbonic acid 6-amino-9-benzyl-2-(2-methoxy-ethoxy)-9H-purin-8-yl ester pentyl ester (54)

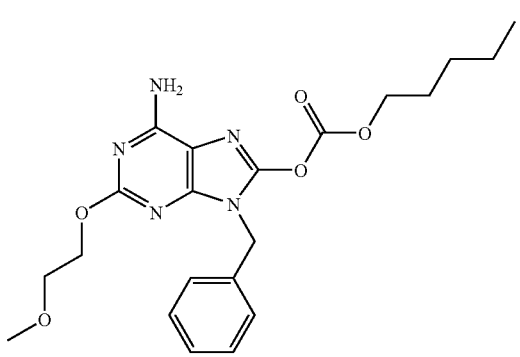

92% yield as a white solid: $^1$H NMR (400 MHz, CDCl$_3$) δ 7.45 (d, J=6.4 Hz, 2H), 7.27 (m, 3H), 4.99 (s, 2H), 4.45 (t, J=4.8 Hz, 2H), 4.39 (t, J=7.2 Hz, 2H), 3.73 (t, J=5.2 Hz, 2H), 3.4 (s, 3H), 2.15 (m, 1H), 1.82 (m, 2H), 1.40 (m, 4H), 0.93 (t, J=6.8 Hz, 3H); MS [M+H]+m/z 430.2.

Example 14

Carbonic acid allyl ester 6-amino-9-benzyl-2-(2-methoxy-ethoxy)-9H-purin-8-yl ester (55)

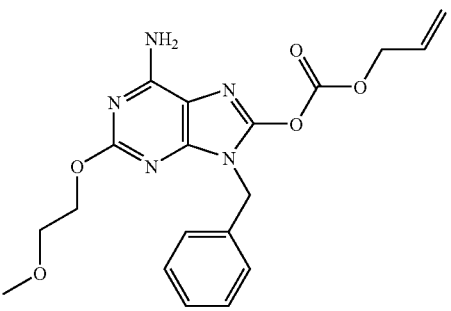

93% yield as a white solid: $^1$H NMR (400 MHz, CDCl$_3$) δ 7.46 (d, J=6.0 Hz, 2H), 7.25 (m, 3H), 6.0 (m, 1H), 5.5 (m, 1H), 5.35 (m, 1H), 4.99 (s, 2H), 4.89 (d, J=2.4 Hz, 2H), 4.46 (t, J=4.8 Hz, 2H), 3.74 (d, J=5.2 Hz, 2H), 3.42 (s, 3H); MS [M+H]+m/z 400.2.

Example 15

Carbonic acid 6-amino-9-benzyl-2-(2-methoxy-ethoxy)-9H-purin-8-yl ester 4-chloro-butyl ester (56)

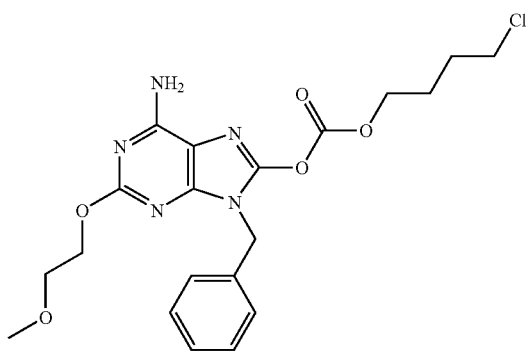

98% yield as a white solid: 1H $^1$H NMR (400 MHz, CDCl$_3$) δ 7.44 (d, J=6.0 Hz, 2H), 7.25 (m, 3H), 4.98 (s, 2H), 4.45 (m, 4H), 3.63 (t, J=5.2 Hz, 2H), 3.42 (s, 3H), 1.99 (m, 4H); MS [M+H]+m/z 450.2.

Example 16

Carbonic acid 6-amino-9-benzyl-2-(2-methoxy-ethoxy)-9H-purin-8-yl ester butyl ester (57)

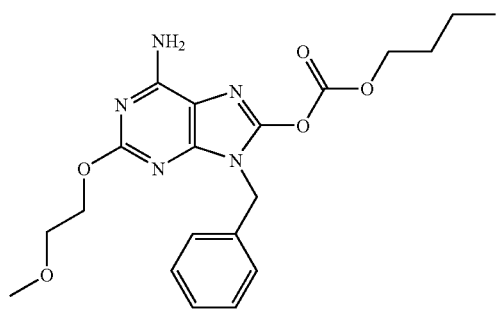

100% yield as a white solid: $^1$H NMR (400 MHz, CDCl$_3$) δ 7.45 (d, J=6.0 Hz, 2H), 7.27 (m, 3H), 4.99 (s, 2H), 4.46 (m, 2H), 4.41 (t, J=4.4 Hz, 2H), 3.73 (t, J=7.2 Hz, 2H), 3.42 (s, 3H), 1.79 (m, 2H), 1.48 (m, 2H), 0.96 (t, J=7.6 Hz, 3H); MS [M+H]+m/z 416.2.

Example 17

Carbonic acid 6-amino-9-benzyl-2-(2-methoxy-ethoxy)-9H-purin-8-yl ester phenyl ester (58)

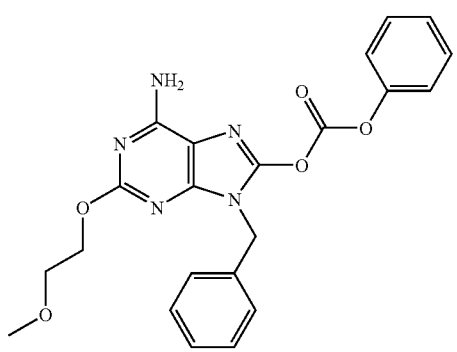

100% yield as a white solid: $^1$H NMR (400 MHz, CDCl$_3$) δ 7.52 (d, J=6.8 Hz, 2H), 7.41 (m, 2H), 7.30 (m, 3H), 7.25 (m, 3H), 4.99 (s, 2H), 4.47 (t, J=4.8 Hz, 2H), 3.75 (t, J=4.8 Hz, 2H), 3.43 (s, 3H); MS [M+H]+m/z 436.2.

Example 18

Carbonic acid 6-amino-9-benzyl-2-(2-methoxy-ethoxy)-9H-purin-8-yl ester 2,2-dimethyl-propyl ester (59)

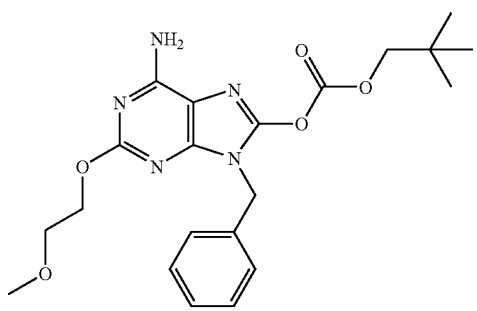

100% yield as a white solid: $^1$H NMR (400 MHz, CDCl$_3$) δ 7.43 (d, 2H), 7.25 (m, 3H), 4.99 (s, 2H), 4.47 (t, 2H), 4.08 (s, 2H), 3.75 (t, 2H), 3.42 (s, 3H), 1.07 (s, 9H); MS [M+H]+m/z 430.2.

Example 19

Carbonic acid 6-amino-9-benzyl-2-(2-methoxy-ethoxy)-9H-purin-8-yl ester heptyl ester (60)

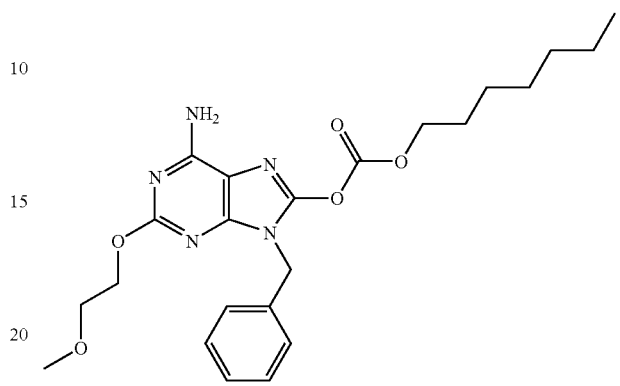

100% yield as a white solid: $^1$H NMR (400 MHz, CDCl$_3$) δ 7.45 (d, J=6.0 Hz, 2H), 7.27 (m, 3H), 4.99 (s, 2H), 4.46 (t, J=5.2 Hz, 2H), 4.39 (t, J=7.2 Hz, 2H), 3.74 (t, J=5.2 Hz, 2H), 3.42 (s, 3H), 1.8 (m, 2H), 1.4 (m, 2H), 1.3 (m, 6H) 0.87 (t, J=7.2 Hz, 3H); MS [M+H]+m/z 458.3.

Example 20

Carbonic acid 6-amino-9-benzyl-2-(2-methoxy-ethoxy)-9H-purin-8-yl ester hexyl ester (30)

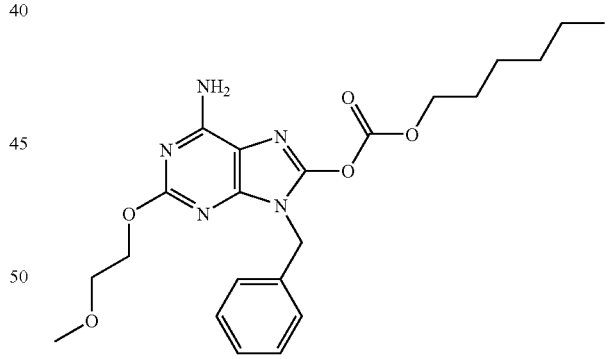

74% yield as a white solid: $^1$H NMR (400 MHz, CDCl$_3$) δ 7.45 (d, J=5.6 Hz, 2H), 7.27 (m, 3H), 4.98 (s, 2H), 4.45 (t, J=4.8 Hz, 2H), 4.41 (t, J=6.8 Hz, 2H), 3.73 (t, J=4.4 Hz, 2H), 3.42 (s, 3H), 1.81 (m, 2H), 1.34 (m, 2H), 1.31 (m, 2H), 1.26 (m, 2H), 0.89 (t, J=2 Hz, 3H); MS [M+H]+m/z 444.4.

Examples 22 and 23 were prepared from 9-benzyl-2-(2-methoxy-ethoxy)-9H-purin-6-ylamine, 62, via 9-benzyl-8-bromo-2-(2-methoxy-ethoxy)-9H-purin-6-ylamine, 63 and sodium ethoxide or methoxide respectively according to the procedures of Kurimoto et al., *Bioorg. Med. Chem.*, 12, 1091-1099 (2004).

Example 21

9-Benzyl-2-(2-methoxy-ethoxy)-9H-purin-6-ylamine (62)

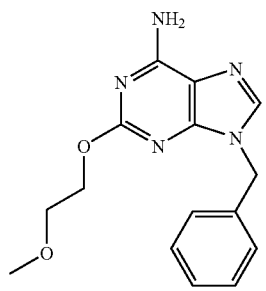

100% yield as a brown solid: $^1$H NMR (400 MHz, CDCl$_3$) δ 7.59 (s, 1H), 7.27 (m, 5H), 5.83 (s, 2H), 5.26 (s, 2H), 4.49 (t, J=4.8 Hz, 2H), 3.75 (t, J=5.2 Hz, 2H), 3.43 (s, 3H); MS [M+H]$^+$ m/z 300.2.

Example 22

9-Benzyl-8-ethoxy-2-(2-methoxy-ethoxy)-9H-purin-6-ylamine (64)

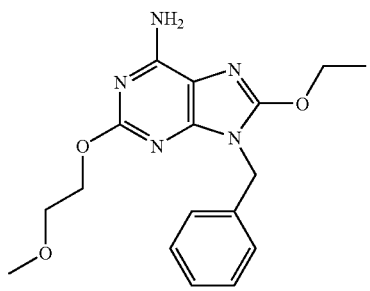

91% yield as a brown solid: $^1$H NMR (400 MHz, d$_6$-DMSO) δ 7.24 (m, 2H), 7.24 (m, 3H), 5.00 (s, 2H), 4.42 (m, 2H), 4.27 (t, J=4.8 Hz, 2H), 3.58 (t, J=4.8 Hz, 2H), 3.26 (s, 3H), 1.32 (t, J=7.2 Hz, 3H); MS [M+H]$^+$ m/z 344.1.

Example 23

9-Benzyl-8-methoxy-2-(2-methoxy-ethoxy)-9H-purin-6-ylamine (65)

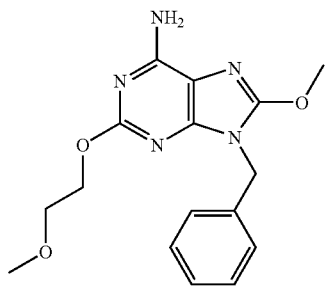

91% yield as a brown solid: $^1$H NMR (400 MHz, d$_6$-DMSO) δ 7.28 (m, 2H), 7.22 (m, 3H), 6.86 (s, 2H), 5.01 (s, 2H), 4.26 (t, J=4.4 Hz, 2H), 4.02 (s, 3H), 3.58 (t, J=4.8 Hz, 2H), 3.25 (s, 3H); MS [M+H]$^+$ m/z 330.2.

Example 24

7-Allyl-2-Amino-9-(5'-O-L-valinyl-β-D-ribofuranosyl)-7,9-dihydro-1H-purine-6,8-dione (68)

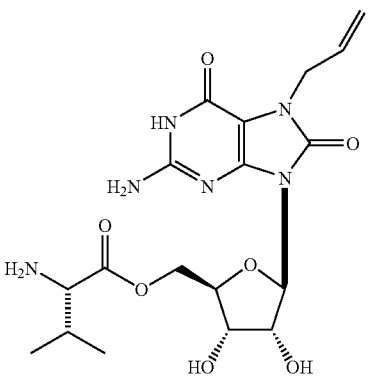

Step 1: Preparation of 7-Allyl-2-amino-9-(2', 3'-O-isopropylidene-β-D-ribofuranosyl)-7,9-dihydro-1H-purine-6,8-dione (66)

Compound 17 (0.17 g, 0.49 mmol) was dissolved in DMF (4.0 mL) and acetone (3.0 mL) was added to the solution. To the mixture was added 2,2-dimethoxypropane (0.18 mL, 1.47 mmol) and MeSO$_3$H (0.02 mL, 0.05 mmol). The reaction mixture was stirred at ambient temperature for 20 h and quenched with saturated aqueous NaHCO$_3$. The aqueous phase was then extracted (4×) with CH$_2$Cl$_2$. The combined organic phase was dried (MgSO$_4$), filtered and concentrated under vacuum to afford 130 mg of 66 in 70% yield as a white solid: $^1$H NMR (400 MHz, CD$_3$OD) δ 5.97 (d, J=2.4 Hz, 1H), 5.93 (m, 1H), 5.34 (dd, J=4.4, 2.0 Hz, 1H), 5.15 (m, 1H), 5.12 (dd, J=7.6, 1.2 Hz, 1H), 4.98 (m, 1H), 4.52 (d, J=5.6, 2H), 4.16 (m, 1H), 3.71 (m, 2H), 1.56 (s, 3H), 1.36 (s, 3H); MS (+)-ES [M+H]$^+$ 380.0 m/z.

Step 2: Preparation of 7-Allyl-2-amino-9-(2',3'-O-isopropylidene-5'-N-tert-butoxycarbonyl-L-valinyl)-β-D-ribofuranosyl)-7,9-dihydro-1H-purine-6,8-dione (67)

A mixture of 66 (0.13 g, 0.34 mmol), BOC-Valine (0.08 g, 0.36 mmol), EDC (0.07 g, 0.38 mmol), DMAP (0.05 g, 0.38 mmol) in THF (8.0 mL) and pyridine (0.8 mL) under N$_2$ atmosphere was stirred at ambient temperature for 16 h. The solvents were removed under vacuum and the residue dissolved in EtOAc. The organic phase was washed with saturated aqueous NaHCO$_3$, brine, dried (MgSO$_4$) and filtered. The filtrate was concentrated under vacuum and the purified by flash chromatography using a 2% to 5% gradient of MeOH in CH$_2$Cl$_2$ to give 180 mg of 67 (91%) as pale yellow solid: $^1$H NMR (400 MHz, CDCl$_3$) δ 6.07 (s, 1H), 5.80 (m, 1H), 5.56 (br s, 2H), 5.41 (d, J=5.6 Hz, 1H), 5.15 (m, 3H), 4.97 (br s, 1H), 4.53 (br s, 2H), 4.46 (m, 1H), 4.32 (m, 2H), 4.20 (m, 1H), 2.11 (m, 1H), 1.56 (s, 3H), 1.44 (s, 9H), 1.36 (s, 3H), 0.93 (d, J=6.8 Hz, 3H), 0.84 (d, J=6.8 Hz, 3H); MS (+)-ES [M]$^+$ 578.9 m/z.

Step 3: 7-Allyl-2-Amino-9-(5'-O-L-valinyl-β-D-ribofuranosyl)-7,9-dihydro-1H-purine-6,8-dione (68)

To a solution of 67 (0.18 g, 0.311 mmols) in MeOH (10 mL) was added AcCl (0.86 mL, 12.07 mmol) under $N_2$ atmosphere. The reaction mixture was left to stir at ambient temperature for 18 h and thereafter carefully neutralized with saturated aqueous $NaHCO_3$. To the mixture was added silica gel and concentrated under vacuum. The residue was purified by flash chromatography using a 10% to 20% gradient of MeOH in $CH_2Cl_2$ to give 80 mg of 68 (59%) as a white solid: $^1$H NMR (400 MHz, $d_6$-DMSO) δ 6.72 (br s, 2H), 5.84 (m, 1H), 5.59 (d, J=4.8 Hz, 1H), 5.43 (d, J=5.6 Hz, 1H), 5.15 (br s, 1H), 5.07 (d, J=12 Hz, 1H), 5.0 (d, J=18.8 Hz, 1H), 4.77 (q, J=4.8 Hz, 1H), 4.36 (m, 3H), 4.26 (t, J=4.4 Hz, 1H), 4.20 (m, 1H), 3.93 (m, 1H), 3.57 (br s, 1H), 2.01 (m, 1H), 0.86 (d, J=4.4 Hz, 3H), 0.85 (d, J=5.2 Hz, 3H); MS (+)-ES $[M+H]^+$ 439.1 m/z.

Example 25

7-Allyl-2-amino-9-β-D-ribofuranosyl-6-(5-methyl-2-oxo-[1,3]dioxol-4-ylmethoxy)-7,9-dihydro-purin-8-one (71)

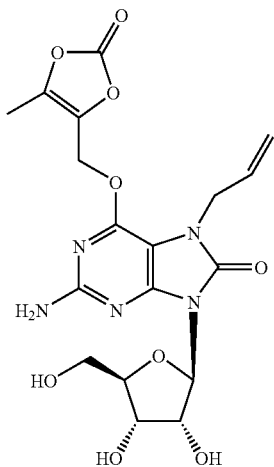

Step 1: Preparation of 7-Allyl-2-amino-9-(2',3,5'-tris-O-triethylsilanyl-β-D-ribofuranosyl)-7,9-dihydro-1H-purine-6,8-dione (69)

To a solution of 17 (0.46 g, 1.36 mmol) and imidazole (0.93 g, 13.64 mol) in DMF (13 mL) was added chlorotriethylsilane (0.92 mL, 5.46 mmol) dropwise and stirred at ambient temperature for 2.5 h. The reaction mixture was treated with saturated aqueous $NaHCO_3$ and the resulting two phases separated. The aqueous phase was washed with diethyl ether (2×). The organic layers were combined and washed with water, dried ($MgSO_4$) and concentrated after filtration. The residue was purified by flash chromatography using a 2% to 10% gradient of MeOH in $CH_2Cl_2$ to give 830 mg of 69 (89%) as pale yellow oil: $^1$H NMR (400 MHz, $CDCl_3$) δ 5.92 (m, 1H), 5.85 (d, J=6.8 Hz, 1H), 5.3 (m, 1H), 5.15-5.23 (m, 2H), 5.09 (br s, 2H), 4.54 (d, J=4.4 Hz, 2H), 4.33 (m, 1H), 3.98 (m, 1H), 3.67-3.80 (m, 2H), 0.85-1.02 (m, 26H), 0.48-0.71 (m, 19H): MS (+)-ES $[M]^+$ 682.6 m/z.

Step 2: Preparation of 7-Allyl-2-amino-9-(2'3',5'-tris-O-triethylsilanyl-β-D-ribofuranosyl)-6-(5-methyl-2-oxo-[1,3]dioxol-4-ylmethoxy)-7,9-dihydro-purin-8-one (70)

In a manner similar to Step 1 of Example 2, compound 70 was prepared from compound 69 and 4-hydroxymethyl-5-methyl-[1,3]dioxol-2-one (prepared according to the procedure of Alepegiani, *Syn. Comm.*, 22(9), 1277-82 (1992)) in 5% yield as a white solid after HPLC purification (Thomson ODS-A 100A 5u 50×21.2 mm column; flow rate=30 mL/min; $CH_3CN$ with 0.05% TFA (A), Water with 0.05% TFA (B); Make up pump flow=1.0 mL/min; Make up pump mobile phase; MeOH with 0.05% TFA using a gradient system as follows: t=0; 50% A, 50% B; t=2.0 min; 50% A, 50% B; t=5.0 min; 100% A, 0% B; t=9.5 min; 100% A, 0% B; t=10.0 min; 50% A, 50% B; t=13.0 min; 50% A, 50% B.); MS (+)-ES $[M]^+$ 794.1 m/z.

Step 3: Preparation of 7-Allyl-2-amino-9-β-D-ribofuranosyl-6-(5-methyl-2-oxo-[1,3]dioxol-4-ylmethoxy)-7,9-dihydro-purin-8-one (71)

To a solution of 70 (9.0 mg, 0.012 mmol) in MeOH (1.5 mL) was added $3HFNEt_3$ (0.01 mL, 0.07 mmol) and stirred at ambient temperature for 16 h. The solvent was removed under vacuum and the residue purified by flash chromatography. The desired product was eluted with 2% to 5% gradient of MeOH in $CH_2Cl_2$ to afford 3.26 mg of 71 (64%) as white solid: $^1$H NMR (400 MHz, $CDCl_3$) 5.96 (d, J=7.6 Hz, 1H), 5.85 (m, 1H), 5.17 (m, 4H), 4.96 (t, J=7.2 Hz, 1H), 4.47 (d, J=6.0 Hz, 2H), 4.25 (J=5.2 Hz, 1H), 4.24 (s, 1H), 3.81 (ABq, $\Delta\upsilon_{AB}$=0.17, $J_{AB}$=11.6 Hz, 2H), 2.22 (s, 3H): MS (+)-ES $[M+H]^+$ 452.4 m/z.

Example 26

(7-Allyl-2-amino-9-β-D-ribofuranosyl-8-oxo-8,9-dihydro-7H-purin-6-yloxymethyl)-methyl-carbamic acid ethyl ester (73)

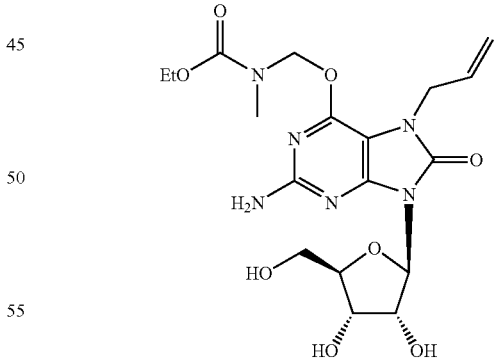

Step 1: Preparation of (7-Allyl-2-amino-9-(2',3',5'-tris-O-triethylsilanyl-β-D-ribofuranosyl)-8-oxo-8,9-dihydro-7H-purin-6-yloxymethyl)-methyl-carbamic acid ethyl ester (72)

In a manner similar to Step 1 of Example 2 compound 72 was prepared in 4% yield from compound 69 and N-methyl-N-(hydroxymethyl)urethane (Kelper, *JOC*, 52, 1987, p.453-

455) as a white solid after HPLC purification: $^1$H NMR (400 MHz, CDCl$_3$) δ 5.94 (m, 1H), 5.82 (d, J=6.4 Hz, 1H), 5.53 (br s, 1H), 5.23-5.29 (m, 2H), 5.15 (t, J=9.6 Hz, 1H), 4.57 (d, J=5.2 Hz, 2H), 4.35 (br s, 1H), 4.21 (m, 2H), 3.96 (br s, 1H), 3.73 (m, 2H), 3.06 (s, 3H), 1.30 (m, 4H), 0.87-1.01 (m, 24H), 0.57-0.68 (m, 19H): MS (+)-ES [M+H]$^+$ 797.7 m/z.

Step 2: Preparation of (7-Allyl-2-amino-9-β-D-ribofuranosyl-8-oxo-8,9-dihydro-7H-purin-6-yloxymethyl)-methyl-carbamic acid ethyl ester (73)

In a manner similar to Step 3 of Example 25 was prepared the title compound 73 in 64% as a white solid after HPLC purification (Thomson ODS-A 100A 5μ 50×21.2 mm column; flow rate=30 mL/min; CH$_3$CN with 0.05% TFA (A), Water with 0.05% TFA (B); Make up pump flow=1.0 mL/min; Make up pump mobile phase; MeOH with 0.05% TFA using a gradient system as follows: t=0; 50% A, 50% B; t=2.0 min; 50% A, 50% B; t=5.0 min; 100% A, 0% B; t=9.5 min; 100% A, 0% B; t=10.0 min; 50% A, 50% B; t=13.0 min; 50% A, 50% B.). $^1$H NMR (400 MHz, CDCl$_3$) δ 5.92 (m, 1H), 5.92 (d, J=7.6 Hz, 1H), 5.51 (m, 2H), 5.22 (d, J=15.6 Hz, 1H), 5.16 (d, J=9.2 Hz, 1H), 4.92 (t, J=7.2 Hz, 1H), 4.57 (d, J=6.0, 2H), 4.40 (d, J=6.0, 11H), 4.21 (m, 3H), 3.79 (ABq, Δυ$_{AB}$=0.178, J$_{AB}$=14.0 Hz, 2H), 3.06 (s, 3H), 1.31 (t, J=7.2 Hz, 3H): MS (+)-ES [M]$^+$ 455.4 m/z.

Example 27

5-Amino-3-(5'-O-L-valinyl-β-D-ribofuranosyl)thiazolo [4,5-d]pyrimidine-2,7-dione Dihydrochloride (24)

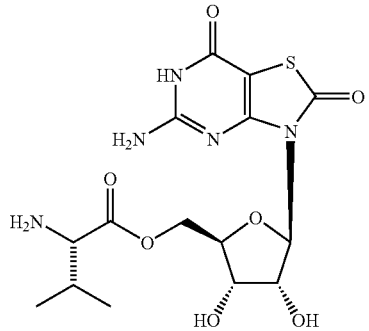

Step 1: Preparation of 5-Amino-3-(2',3'-O-isopropylidene-β-D-ribofuranosyl) thiazolo[4,5-d]pyrimidine-2,7-dione (22)

To a heterogeneous mixture of 21 (5.37 g, 17.0 mmol, prepared according to the procedure given in U.S. Pat. No. 5,041,426 (Example 2), which is incorporated by reference in its entirety) in acetone (40 mL) contained in a 250 mL Morton flask was added successively 2,2-DMP (6.26 mL, 50.9 mmol), DMSO (6.6 mL), and MeSO$_3$H (220 μL, 3.39 mmol) at room temperature. The reaction mixture was stirred vigorously, becoming homogeneous and golden yellow as the diol was consumed. TLC analysis (SiO$_2$, 10% MeOH—CHCl$_3$) indicated reaction completion after 6 h. Undissolved solids were removed via gravity filtration using fluted Whatman type 1 filter paper. This was followed by pouring of the filtrate into 10 volumes of ice water (~400 mL), resulting in immediate precipitation of a white solid. After a brief period of stirring, NaHCO$_3$ (285 mg, 3.39 mmol) dissolved in water (10 mL) was added to neutralize the MeSO$_3$H. Vigorous stirring in the Morton reactor was continued for 15 min, whereupon the mixture was filtered through a coarse scintered glass funnel. The solid material was washed with ice water (100 mL), air dried, then dried further under high vacuum at 65° C., affording 5.36 g (88%) of the acetonide 22 as a white solid: mp 280-81° C.; $^1$H (DMSO-d$_6$) δ 1.28 (s, 3H), 1.47 (s, 3H), 3.43-3.55 (m, 2H), 3.95-3.99 (m, 1H), 4.77-4.80 (m, 1H), 4.88-4.91 (m, 1H), 5.24-5.26 (m, 1H), 5.99 (s, 1H), 6.97 (br s, 2H), 11.25 (s, 1H).

Step 2: Preparation of 5-Amino-3-(2',3'-O-isopropylidene-5'-N-tert-butoxycarbonyl-L-valinyl)-β-D-ribofuranosyl)-thiazolo[4,5-d]pyrimidine-2,7-dione (23)

To a solution of N-butoxycarbonyl-(L)-valine (671 mg, 2.81 mmol) in THF (9 mL) at 0° C. was added EDC (588 mg, 3.07 mmol). The resultant homogeneous mixture was stirred 45 min at 0° C., at which point it had become heterogeneous, and solid acetonide 2 from Step 1 above (1.00 g, 2.81 mmol) was added as one portion. Subsequently added was solid DMAP (522 mg, 4.27 mmol). The reaction mixture was permitted to reach room temperature, and stirred an additional 5 h, whereupon it was concentrated at 25° C. via rotary evaporation to a yellow syrup. The residue was dissolved in EtOAc (50 mL), partitioned with 1 N HCl (10 mL) followed by neutralization of acid with saturated aqueous NaHCO$_3$ (10 mL). The acidic aqueous phase was further extracted with EtOAc (2×50 mL), and then partitioned with the basic aqueous phase. The combined organic phases were dried over Na$_2$SO$_4$, filtered through a short pad of SiO$_2$, and concentrated, affording 1.480 g (96%) of Boc-protected amino acid ester 23 as a foam: mp 158° C. (dec); $^1$H (CDCl$_3$) δ 0.86 (d, J=7.0, 3H), 0.95 (d, J=7.0, 3H), 1.35 (s, 3H), 1.44 (s, 9H), 1.56 (s, 3H), 1.75 (br s, 1H), 2.08-2.19 (m, 1H), 4.20-4.24 (m, 2H), 4.30-4.37 (m, 11), 4.56 (dd, J=11.0, 5.9, 1H), 4.96 (dd, J=6.2, 3.7, 1H), 5.11 (br d, J=8.8, 1H), 5.29 (br d, J=6.6, 1H), 5.88 (br s, 2H), 6.23 (s, 11H).

Step 3: Preparation of 5-Amino-3-(5'-O-L-valinyl-β-D-ribofuranosyl)thiazolo[4,5-d]pyrimidine-2,7-dione Dihydrochloride (24)

A stream of HCl gas was passed through a bubbler of concentrated H$_2$SO$_4$, and subsequently directed (via fritted dispersion tube) into a 250 mL 3-neck Morton flask containing dry isopropyl acetate (80 mL) at 0° C. until a saturated solution was obtained. To this was added a solution of the Boc-amino acid ester from Step 2 above (5.53 g, 9.95 mmol) in isopropyl acetate (30 mL), resulting in the formation of a white solid precipitate within 5 min. To this was added 10% (v/v) IPA (11 mL). The reaction mixture was warmed to room temperature, then stirred 12 h. The heterogeneous reaction mixture was diluted with dry toluene (100 mL). Filtration using a medium pore scintered glass funnel under N$_2$ provided an off-white, amorphous solid. Trituration of the solid in dry THF was followed by filtration and vacuum drying at 65° C., affording 3.677 g (81%) of the title compound 24 as a white solid: mp 166-68° C. (dec); $^1$H (DMSO-d$_6$) δ 0.90 (d, J=7.0, 3H), 0.94 (d, J=7.0, 3H), 2.14-2.18 (m, 1H), 3.83-3.85 (m, 1H), 3.96-4.00 (m, 1H), 4.23-4.28 (m, 2H), 4.42 (dd, J=11.7, 3.4, 1H), 4.75 (dd, J=10.3, 5.5, 1H), 5.81 (d, J=4.4, 1H), 6.46 (br s, 3H), 7.23 (br s, 2H), 8.47 (s, 3H), 11.5 (br s, 1H). Elemental analysis for C$_{15}$H$_{21}$N$_5$O$_7$S.2HCl: calc'd: C, 36.89; H, 4.75; Cl, 14.52; N, 14.34; S, 6.57; found: C, 37.03: H, 4.74; Cl, 14.26; N, 14.24; S, 6.42.

Example 28

5-Acetylamino-3-(2',3',5'-tri-O-acetyl-β-D-ribofuranosyl)thiazolo [4,5-d]pyrimidine-2,7(6H)-dione (74)

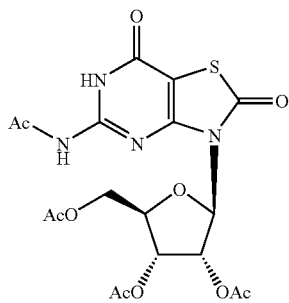

Step 1: Preparation of 5-Acetylamino-3-(2',3',5'-tri-O-acetyl-β-D-ribofuranosyl)thiazolo[4,5-d]pyrimidine-2,7(6H)-dione (74)

Anhydrous 21 (8.0 g, 39.5 mmol) was dissolved in dry pyridine (65 mL). DMAP (3.1 g, 25.3 mmol) and acetic anhydride (19.1 mL 202.4 mmol) were added sequentially. The reaction was allowed to progress for 2 h at room temperature, whereupon it was quenched with saturated NaHCO$_3$ (100 mL) and extracted with DCM (3×200 mL). The organic phase was concentrated, and then triturated with ether. This provided 12.5 g (103%) of slightly impure 5-acetylamino-3-(2,3,5-tri-O-acetyl-β-D-ribofuranosyl)thiazolo-[4,5-d]pyrimidin-2,7(6H)-dione as a white solid 74: mp 246.7-248.1° C.; R$_f$=0.20 (SiO$_2$, 50% EtOAc-CHCl$_3$); $^1$H NMR (400 MHz, d$_6$-DMSO) δ 12.23 (s, 1H), 11.85 (s, 1H), 5.97 (m, 2H), 5.48 (t, J=6, 1H), 4.35-4.40 (m, 1H), 4.25-4.31 (m, 1H), 4.08-4.18 (m, 1H), 2.49 (s, 3H), 2.07 (s, 3H), 2.01 (s, 3H), 2.00 (s, 3H).

Example 29

5-Amino-3-(2',3',5'-tri-O-acetyl-β-D-ribofuranosyl)thiazolo[4,5-d]pyrimidine-2,7(6H)-dione (75)

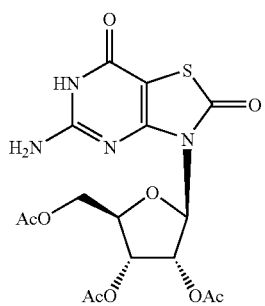

Step 1: Preparation of 5-Amino-3-(2',3',5'-tri-O-acetyl-β-D-ribofuranosyl)thiazolo[4,5-d]pyrimidine-2,7(6H)-dione (75)

To a suspension of 21 (5.00 g, 15.8 mmol) in acetonitrile (160 mL) at 0° C. was added successively Et$_3$N (11.0 mL, 79.0 mmol), DMAP (195 mg, 1.59 mmol), and Ac$_2$O (4.47 mL, 47.4 mmol). The reaction mixture was stirred at room temperature for 2 h, whereupon it was concentrated to a brown syrup. The residue was purified by flash column chromatography (silica, MeOH/CHCl$_3$=1-10%) to afford 6.22 g (89%) of triacetate 75 as a white solid: mp 198-199° C.; $^1$H (400 MHz, d$_6$-DMSO) δ 11.34 (s, 1H), 7.02 (br s, 2H), 5.90 (m, 2H), 5.51 (t, J=6.0 Hz, 1H), 4.36 (dd, J=12.4, 3.2 Hz, 1H), 4.21 (m, 1H), 4.08 (q, J=6.0 Hz, 1H), 2.06 (s, 3H), 2.06 (s, 3H), 2.00 (s, 3H); MS (+)-ES [M+H]$^+$ m/z 443.3.

Example 30

5-Amino-7-ethoxy-3-β-D-ribofuranosyl-thiazolo[4,5-d]pyrimidin-2-one (77)

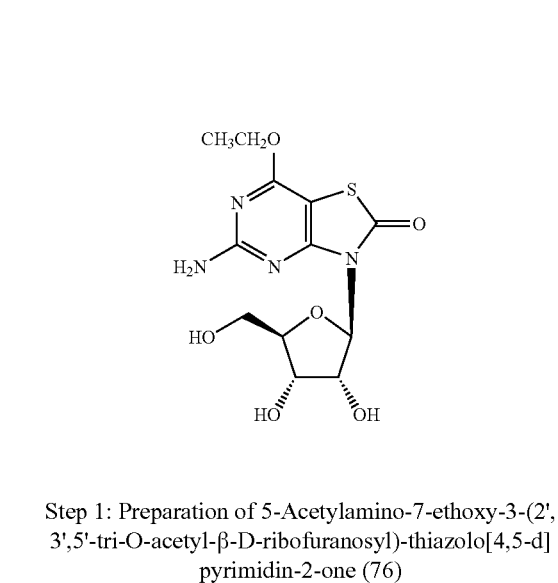

Step 1: Preparation of 5-Acetylamino-7-ethoxy-3-(2',3',5'-tri-O-acetyl-β-D-ribofuranosyl)-thiazolo[4,5-d]pyrimidin-2-one (76)

In a manner similar to Example 2, step 1, 76 was prepared from 74 and ethanol in 72% yield as a white foam: MS (+)-ES [M+H]$^+$ m/z 513. R$_f$=0.45 (75% Ethyl acetate-CHCl$_3$).

Step 2: Preparation of 5-Amino-7-ethoxy-3-β-D-ribofuranosyl-thiazolo[4,5-d]pyrimidine-2-one (77)

In a manner similar to Example 2, step 2, the title compound was prepared from 76 in 65% yield as a white solid: $^1$H NMR (400 MHz, d$_6$-DMSO) δ 6.87 (s, 2H), 5.85 (d, J=4.8 Hz, 1H), 5.27 (d, J=5.6 Hz, 1H), 4.96 (d, J=5.2 Hz, 1H), 4.78 (m, 1H), 4.66 (m, 1H), 4.36 (m, 2H), 4.09 (m, 1H), 3.74 (m, 1H), 3.58 (m, 1H), 3.40 (m, 1H), 1.29 (m, 3H); MS (+)-ES [M+H]$^+$ m/z 445, [2M+H]$^+$ m/z 689. R$_f$=0.2 (50% THF-CHCl$_3$). Elemental Analysis for C$_{12}$H$_{16}$N$_4$O$_6$S.0.25H$_2$O: calc'd: C, 41.31; H, 4.77; N, 16.06; S, 9.19. Found: C, 41.24; H, 4.71; N, 15.89; S, 9.06.

Example 31

5-Amino-7-methoxy-3-β-D-ribofuranosyl-thiazolo[4,5-d]pyrimidin-2-one (79)

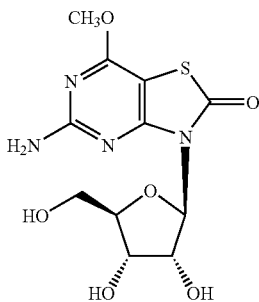

Step 1. Preparation of 5-Acetylamino-7-methoxy-3-(2',3',5'-tri-O-acetyl-β-D-ribofuranosyl)-thiazolo[4,5-d]pyrimidin-2-one (78)

In a manner similar to Example 2, step 1, 77 was prepared from 74 and methanol in 65% yield as a white foam: MS (+)-ES [M+H]$^+$ 499. $R_f$=0.5 (75% Ethyl acetate-CHCl$_3$).

Step 2: Preparation of 5-Amino-7-methoxy-3-β-D-ribofuranosyl-thiazolo[4,5-d]pyrimidin-2-one (79)

In a manner similar to Example 2, step 2, the title compound was prepared from 78 in 78% yield as a white solid: $^1$H NMR (400 MHz, d$_6$-DMSO) δ 6.91 (s, 2H), 5.86 (d, J=5.2 Hz, 1H), 5.28 (d, J=5.2 Hz, 1H), 4.96 (d, J=5.2 Hz, 1), 4.77 (m, 1H), 4.66 (m, 1H), 4.09 (m, 1H), 3.90 (s, 3H), 3.75 (m, 1H), 3.56 (m, 1H), 3.43 (m, 1H); MS (+)-ES [M+H]$^+$ 331. $R_f$=0.2 (50% THF-CHCl$_3$). Elemental Analysis for C$_{11}$H$_{14}$N$_4$O$_6$S.0.25 H$_2$O: calc'd: C, 39.46; H, 4.37; N, 16.73; S, 9.58. Found: C, 39.59; H, 4.17; N, 16.55; S, 9.52.

Example 32

(5-Amino-2-oxo-3-β-D-ribofuranosyl-2,3-dihydro-thiazolo[4,5-d]pyrimidin-7-yloxymethyl)-carbamic acid ethyl ester (82)

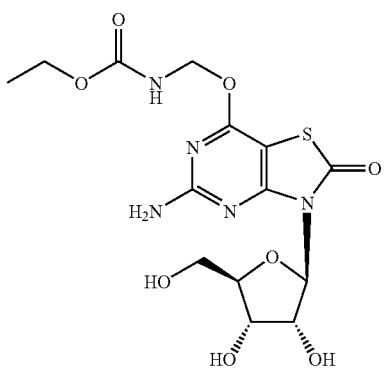

Step 1: Preparation of 5-Amino-3-(2',3',5'-tris-O-triethylsilanyl-β-D-ribofuranosyl)-thiazolo[4,5-d]pyrimidin-2,7-dione (80)

To a suspension of 21 (1.00 g, 3.16 mmol) in DMF (20 mL) at room temperature was added successively imidazole (753 mg, 11.06 mmol), DMAP (39 mg, 0.32 mmol), and chlorotriethylsilane (1.64 mL, 9.80 mmol). The reaction mixture was stirred at room temperature for 2 h, whereupon it was quenched by saturated NaHCO$_3$ solution (20 mL). The mixture was extracted with CHCl$_3$ (3×20 mL), dried over MgSO$_4$ and concentrated. The residue was purified by flash column chromatography (silica, MeOH/CHCl$_3$=1-5%) to afford 1.91 g (92%) of compound 80 as a white solid: $^1$H (400 MHz, d$_6$-DMSO) δ 5.99 (s, 1H), 5.62 (br s, 2H), 5.19 (dd, J=4.4, 6.0 Hz, 1H), 4.35 (dd, J=2.8, 4.4 Hz, 1H), 3.99 (m, 1H), 3.77 (dd, J=7.6, 10.8 Hz, 1H), 3.68 (dd, J=4.8, 10.4 Hz, 1H), 1.10 (t, J=7.1 Hz, 3H), 0.96 (t, J=7.1 Hz, 3H), 0.89 (t, J=7.1 Hz, 3H), 0.68 (q, J=7.1 Hz, 2H), 0.61 (q, J=7.1 Hz, 2H), 0.54 (m, 2H); MS (+)-ES [M+H]$^+$ m/z 660.0.

Step 2: Preparation of 5-Amino-3-(2',3',5'-tris-O-triethylsilanyl-β-D-ribofuranosyl)-2,3-dihydro-thiazolo[4,5-d]pyrimidin-7-yloxymethyl)-carbamic acid ethyl ester (81)

In a manner similar to Step 1 of Example 2, compound 81 was prepared from 80 and N-ethylurethane as a white solid in 31% yield: [M+H]+ 760.5; $^1$H NMR (400 MHz, CDCl$_3$) δ 6.43 (br s, 2H), 6.09 (t, J=7.6 Hz, 1H), 5.94 (d, J=6.0 Hz, 1H), 5.31 (d, J=4.8 Hz, 2H), 5.19 (dd, J=6.0, 4.8 Hz, 1H), 4.35 (dd, J=4.8, 2.8 Hz, 1H), 4.19 (q, J=6.4 Hz, 2H), 3.98 (m, 1H), 3.76 (dd, J=10.8, 7.6 Hz, 1H), 3.68 (dd, J=10.4, 4.8 Hz, 1H), 1.29 (t, J=6.8 Hz, 3H), 1.02 (t, J=8.0 Hz, 3H), 0.96 (t, J=7.6 Hz, 3H), 0.90 (t, J=8.0 Hz, 3H), 0.69 (q, J=8.0 Hz, 2H), 0.61 (q, J=8.0 Hz, 2H), 0.55 (m, 2H); [M+H]$^+$ 760.5.

Step 3: Preparation of (5-Amino-2-oxo-3-β-D-ribofuranosyl-2,3-dihydro-thiazolo[4,5-d]pyrimidin-7-yloxymethyl)-carbamic acid ethyl ester (82)

A solution of 81 (244 mg, 321 μmol), 5M HF in pyridine (321 μL, 1.60 mmol) and THF (3.20 mL) were stirred at room temperature for 5 h. Removal of the solvents under vacuum left a residue that was purified by flash chromatography (SiO$_2$, 10% MeOH—CHCl$_3$) to afford 82 (119 mg, 90%) as a white solid: $^1$H NMR (400 MHz, d$_6$-DMSO) δ 8.43 (br s, 1H), 7.76 (br s, 2H), 5.82 (d, J=5.2 Hz, 1H), 5.78 (s, 2H), 5.32 (d, J=5.6 Hz, 1H), 5.24 (dd, J=6.0, 4.8 Hz, 1H), 5.00 (d, J=5.6 Hz, 1H), 4.82 (q, J=5.6 Hz, 1H), 4.68 (t, J=6.0, 1H), 4.11 (q, J=5.2 Hz, 1H), 4.09 (q, J=7.2 Hz, 2H), 3.78 (q, J=5.6 Hz, 1H), 3.60 (m, 1H), 3.46 (m, 1H), 1.21 (t, J=7.2 Hz, 3H); [M+H]$^+$ 418.2.

Example 33

(5-Amino-2-oxo-3-β-D-ribofuranosyl-2,3-dihydro-thiazolo[4,5-d]pyrimidin-7-yloxymethyl)-methyl-carbamic acid ethyl ester (84)

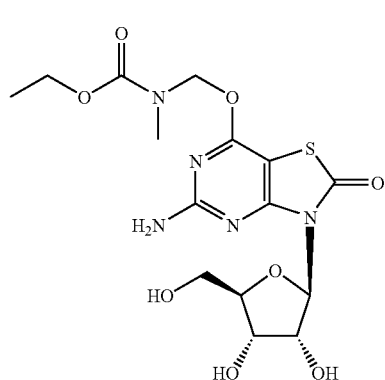

Step 1: Preparation of (5-Amino-2-oxo-3-(2',3',5'-tri-O-acetyl-β-D-ribofuranosyl)-2,3-dihydro-thiazolo[4,5-d]pyrimidin-7-yloxymethyl)-methyl-carbamic acid ethyl ester (83)

In a manner similar to Example 2, step 1, compound 83 was prepared from 75 and N-methyl-N-(hydroxymethyl)urethane as a white solid in 24% yield: $R_f$=0.4 (33% EtOAc-CHCl$_3$); $^1$H NMR (400 MHz, CDCl$_3$) δ 11.49 (br s, 1H), 6.08 (d, J=4.0 Hz, 1H), 5.75 (t, J=6.0 Hz, 1H), 5.53 (s, 2H), 4.49 (dd, J=13.5, 8.4 Hz, 1H), 4.30 (m, 5H), 3.62 (q, J=7.2 Hz, 2H), 2.30 (s, 3H), 2.12 (s, 3H), 2.09 (s, 3H), 2.08 (s, 3H), 1.36 (t, J=6.8 Hz, 3H), 1.20 (t, J=6.8 Hz, 3H); [M+H]$^+$ 614.2.

Step 2: Preparation of (5-Amino-2-oxo-3-β-D-ribofuranosyl-2,3-dihydro-thiazolo[4,5-d]pyrimidin-7-yloxymethyl)-methyl-carbamic acid ethyl ester (84)

In a manner similar to Example 1, step 4, the title compound was prepared from 83 as a white solid in 20% yield: $^1$H NMR (400 MHz, d$_6$-DMSO) δ 7.86 (br s, 2H), 5.82 (d, J=4.8 Hz, 1H), 5.47 (s, 2H), 5.31 (d, J=5.2 Hz, 1H), 5.00 (d, J=5.6 Hz, 1H), 4.82 (q, J=5.2 Hz, 1H), 4.67 (q, J=5.6 Hz, 1H), 4.18 (q, J=6.4 Hz, 2H), 4.12 (m, 1H), 3.78 (q, J=6.0 Hz, 1H), 3.60 (m, 1H), 3.47 (m, 1H), 3.30 (s, 3H), 1.27 (t, J=6.8 Hz, 3H); [M+H]$^+$ 432.3.

Example 34

5-Amino-7-(5-methyl-2-oxo-[1,3]dioxol-4-ylmethoxy)-3-(2',3',5'-tri-O-acetyl-β-D-ribofuranosyl)-thiazolo[4,5-d]pyrimidin-2-one (85)

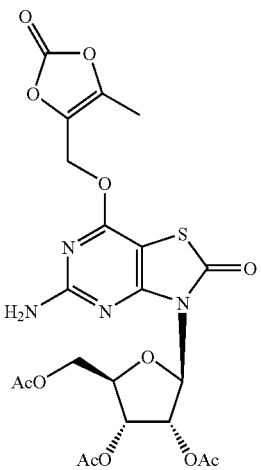

Step 1: Preparation of 5-Amino-7-(5-methyl-2-oxo-[1,3]dioxol-4-ylmethoxy)-3-(2',3',5'-tri-O-acetyl-β-D-ribofuranosyl)-thiazolo[4,5-d]pyrimidin-2-one (85)

To a solution of triacetate 75 (1.55 g, 3.50 mmol) in THF (50 mL) at 0° C. was added polymer supported-triphenylphosphine (4.95 g, 10.50 mmol, Argonaut). To this mixture was added 4-hydroxymethyl-5-methyl-[1,3]dioxol-2-one (0.91 g, 7.00 mmol), prepared according to the procedure of Alepegiani, *Syn. Comm.*, 22(9), 1277-82 (1992) Diethyl azodicarboxylate (0.73 ml, 4.60 mmol) was then added dropwise. The resulting mixture was stirred at room temperature for 48 h, filtered and washed with MeOH and CHCl$_3$. The filtrate was concentrated and purified by flash column chromatography (silica, acetone/CHCl$_3$=10-20%) to afford dioxolone derivative 85 (1.38 g, 71%) as white solid: $^1$H (400 MHz, d$_6$-DMSO);δ 7.06 (s, 2H), 6.00 (d, J=4.0 Hz, 1H), 5.92 (dd, J=6.6, 4.4 Hz, 1H), 5.56 (t, J=6.4 Hz, 1H), 5.30 (s, 2H), 4.38 (dd, J=11.6, 3.6 Hz, 1H), 4.25 (t, J=3.6 Hz, 1H), 4.10 (q, J=6.0 Hz, 1H), 2.23 (s, 3H), 2.08 (s, 3H), 2.07 (s, 3H), 2.00 (s, 3H); MS (+)-ES [M+H]$^+$ m/z 555.3. Elemental Analysis calc'd for C$_{21}$H$_{22}$N$_4$O$_{12}$S.Me$_2$CO: C, 47.06; H, 4.61; N, 9.15; S, 5.23. Found: C, 47.25; H, 4.37; N, 9.53; S, 5.52.

Example 35

5-Amino-7-(5-methyl-2-oxo-[1,3]dioxol-4-yl-methoxy)-3-β-D-ribofuranosyl-thiazolo[4,5-d]pyrimidin-2-one (87)

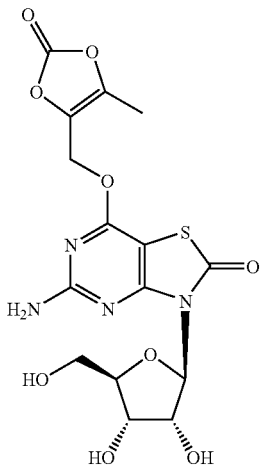

Step 1: Preparation of 5-Amino-7-(5-methyl-2-oxo-[1,3]dioxol-4-ylmethoxy)-3-(2',3',5'-tris-O-triethylsilanyl-β-D-ribofuranosyl)-thiazolo[4,5-d]pyrimidin-2-one (86)

In a manner similar to Example 34, compound 86 was prepared from 80 and 4-hydroxymethyl-5-methyl-[1,3]dioxol-2-one as a white solid in 45% yield: $^1$H NMR (400 MHz, CDCl$_3$) δ 6.06 (d, J=6.0 Hz, 1H), 5.21 (dd, J=6.0, 4.8 Hz, 1H), 5.18 (d, J=3.2 Hz, 2H), 4.94 (br s, 2H), 4.38 (dd, J=4.8, 2.8 Hz, 1H), 4.00 (m, 1H), 3.79 (dd, J=11.2, 8.0 Hz, 1H), 3.69 (dd, J=10.8, 5.2 Hz, 1H), 2.23 (s, 3H), 1.02 (t, J=8.0 Hz, 3H), 0.96 (t, J=7.6 Hz, 3H), 0.89 (t, J=8.4 Hz, 3H), 0.70 (q, J=7.6 Hz, 2H), 0.61 (q, J=8.0 Hz, 2H), 0.53 (m, 2H); [M+H]$^+$ 771.5.

Step 2: Preparation of 5-Amino-7-(5-methyl-2-oxo-[1,3]dioxol-4-ylmethoxy)-3-β-D-ribofuranosyl-thiazolo[4,5-d]pyrimidin-2-one (87)

In a manner similar to Steps 3 of Example 32, the title compound was prepared from 86 as a white solid in 89% yield: $^1$H NMR (400 MHz, d$_6$-DMSO) δ 7.03 (br s, 2H), 5.90 (d, J=5.2 Hz, 1H), 5.33 (s, 2H), 5.02 (d, J=4.8 Hz, 1H), 4.83 (q, J=5.6 Hz, 1H), 4.71 (t, J=6.0 Hz, 1H), 4.14 (q, J=5.2 Hz, 1H), 3.80 (q, J=4.8 Hz, 1H), 3.62 (m, 1H), 3.47 (m, 1H), 2.27 (s, 3H); [M+H]$^+$ 429.2.

Example 36

5-Amino-3-β-D-ribofuranosyl-3H-thiazolo-[4,5-d]pyrimidin-2-one (90)

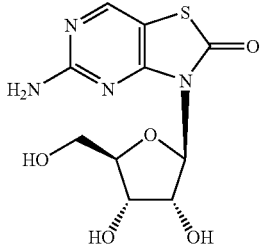

Step 1: Preparation of 5-Amino-7-thioxo-3-(2',3',5'-tri-O-acetyl-β-D-ribofuranosyl)-thiazolo[4,5-d]pyrimidin-2-one (88)

To a solution of 75 (1 g, 2.26 mmol) in pyridine (50 mL) was added at room temperature P$_2$S$_5$ (2.13 g, 4.79 mmol). The solution was refluxed gently (bath temperature 130-140° C.) for 29 h. The reaction mixture was evaporated to dryness in vacuo. The excess P$_2$S$_5$ was decomposed by the addition of H$_2$O (40 mL) at 60° C. The mixture was stirred for 1 h at 60° C. and then cooled to room temperature. The mixture was extracted with CHCl$_3$ (3×40 mL). The dried (MgSO4) organic layer was evaporated to yield a syrup, which was purified by flash column chromatography (silica, acetone/CHCl$_3$=15%) to afford 0.93 g (90%) of 88 as a yellow solid: $^1$H (400 MHz, d$_6$-DMSO) δ 12.50 (s, 1H), 7.35 (br s, 2H), 5.89 (m, 2H), 5.51 (t, J=6.4 Hz, 1H), 4.36 (dd, J=12.0, 4.0 Hz, 1H), 4.24 (m, 1H), 4.10 (q, J=6.0 Hz, 1H), 2.07 (s, 3H), 2.06 (s, 3H), 2.01 (s, 3H); MS (+)-ES [M+H]$^+$ m/z 459.3.

Step 2: Preparation of 5-Amino-3-(2',3',5'-tri-O-acetyl-β-D-ribofuranosyl)-3H-thiazolo[4,5-d]pyrimidin-2-one (89)

A suspension of Raney® 2800 nickel (3 big spatula, prewashed with H$_2$O, MeOH and acetone) in acetone (50 mL) was stirred at refluxing for 1 h. Triacetate 88 (0.93 g, 2.03 mmol) was subsequently added into the above suspension at reflux. The mixture was stirred for 5 min, cooled to room temperature over 30 min. The reaction was quenched by bubbling H$_2$S (g) into the mixture for 2 h. The resulting mixture was filtered through a short pad of Celite® and washed with EtOH. The filtrate was concentrated and purified by flash column chromatography (silica, MeOH/CHCl$_3$=1-2%) to afford 0.52 g (60%) of 89 as a white solid: mp 121-123° C.; $^1$H (400 MHz, d$_6$-DMSO) δ 8.38 (s, 1H), 6.93 (s, 2H), 6.03 (d, J=3.6 Hz, 1H), 5.93 (dd, J=6.4, 3.6 Hz, 1H), 5.58 (t, J=6.0 Hz, 1H), 4.38 (dd, J=11.6, 3.6 Hz, 1H), 4.26 (m, 1H), 4.11 (q, J=6.0 Hz, 1H), 2.08 (s, 3H), 2.07 (s, 3H), 2.00 (s, 3H); MS (+)-ES [M+H]$^+$ m/z 427.2. Elemental Analysis calc'd for C$_{16}$H$_{18}$N$_4$O$_8$S.0.5 CH$_3$OH.0.25H$_2$O: C, 44.34; H, 4.62; N, 12.54; S 7.17. Found: C, 44.54; H, 4.88; N, 12.16; S, 7.17.

Step 3: Preparation of 5-Amino-3-β-D-ribofuranosyl-3H-thiazolo[4,5-d]pyrimidin-2-one (90)

To a solution of 89 (0.52 g, 1.22 mmol) in MeOH (20 mL) was added K$_2$CO$_3$ (25 mg, 0.18 mmol). The reaction was stirred at room temperature overnight, then neutralized with AcOH (21 μL, 0.36 mmol). The resulting mixture was stirred at room temperature for additional 30 min, concentrated, and triturated with H$_2$O (2 ml) to afford 0.33 g of compound 90 (89%) as a white solid: mp 220° C. (Dec); $^1$H (400 MHz, d$_6$-DMSO) δ 8.34 (s, 1H), 6.85 (s, 2H), 5.90 (d, J=4.8 Hz, 1H), 5.31 (d, J=5.6 Hz, 1H), 4.98 (d, J=5.6 Hz, 1H), 4.81 (q, J=5.2 Hz, 1H), 4.67 (t, J=6.0 Hz, 1H), 4.11 (q, J=5.2 Hz, 1H), 3.77 (dd, J=10.8, 4.8 Hz, 1H), 3.58 (m, 1H), 3.44 (m, 1H); MS(+)-ES [M+H]$^+$ m/z 301.1. Elemental Analysis calc'd for C$_{10}$H$_{12}$N$_4$O$_5$S.0.3H$_2$O: C, 39.29; H, 4.15; N, 18.33; S 10.49. Found: C, 39.51; H, 4.18; N, 17.95; S, 10.27.

Example 37

5-Amino-3-(2',3'-di-O-acetyl-β-D-ribofuranosyl)-3H-thiazolo[4,5-d]pyrimidin-2-one (93)

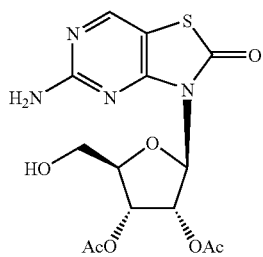

Step 1: Preparation of 5-Amino-3-(5'-O-tert-butyl-dimethylsilanyl-β-D-ribofuranosyl)-3H-thiazolo[4,5-d]pyrimidin-2-one (91)

To a solution of 90 (0.68 g, 2.28 mmol) in DMF (10 mL) was added imidazole (0.54 g, 7.93 mmol) and tert-butyldimethylsilyl chloride (0.68 g, 4.56 mmol) sequentially. The reaction mixture was stirred at room temperature for 2 h, at which point it was concentrated and purified by flash column chromatography (silica, MeOH/CHCl$_3$; gradient=5-20%) to afford 0.49 g (52%) 91 as a white solid: $^1$H (400 MHz, d$_6$-DMSO) δ 8.33 (s, 1H), 6.87 (s, 2H), 5.90 (d, J=4.0 Hz, 1H), 5.33 (d, J=5.6 Hz, 1H), 5.00 (d, J=5.2 Hz, 1H), 4.79 (q, J=5.2 Hz, 1H), 4.16 (q, J=5.2 Hz, 1H), 3.77 (m, 2H), 3.64 (dd, J=12.0, 7.2 Hz, 1H), 0.84 (s, 9H), 0.00 (s, 6H); MS(+)-ES [M+H]$^+$m/z 415.4.

Step 2: Preparation of 5-Amino-3-(2',3'-di-O-acetyl, 5'-O-tert-butyl-dimethylsilanyl-β-D-ribofuranosyl)-3H-thiazolo[4,5-d]pyrimidin-2-one (92)

To a solution of 91 (0.20 g, 0.48 mmol) in acetonitrile (5 mL) at 0° C. was added successively Et$_3$N (0.26 mL, 1.86 mmol) and Ac$_2$O (91 μL, 0.96 mmol). The reaction mixture was stirred at room temperature for 24 h, whereupon it was concentrated and purified by flash column chromatography (silica, acetone/CHCl$_3$: gradient=5-10%) to afford 0.22 g (92%) of 92 as a white solid: $^1$H (400 MHz, d$_6$-DMSO) δ 8.36 (s, 1H), 6.90 (s, 2H), 6.00 (m, 2H), 5.57 (t, J=6.0 Hz, 1H), 4.07 (q, J=5.2 Hz, 1H), 3.77 (m, 2H), 2.07 (s, 3H), 2.06 (s, 3H), 0.83 (s, 9H), 0.00 (d, J=2.4 Hz, 6H); MS (+)-ES [M+H]$^+$ m/z 499.5.

Step 3: Preparation of 5-Amino-3-(2,3'-di-O-acetyl-β-D-ribofuranosyl)-3H-thiazolo[4,5-d]pyrimidin-2-one (93)

To a solution of 92 (0.22 g, 0.44 mmol) in THF (5 mL) in a plastic vial was added HF/pyridine (0.70 mL). The reaction was stirred for 2 h, concentrated and purified by flash column chromatography (silica, MeOH/CHCl$_3$: gradient=5-10%) to afford 0.17 g (100%) of the title compound as a white solid: mp 109-111° C.; $^1$H (400 MHz, d$_6$-DMSO) δ 8.37 (s, 1H), 6.91 (s, 2H), 6.00 (m, 2H), 5.48 (t, J=6.0 Hz, 1H), 4.91 (t, J=6.0 Hz, 1H), 4.04 (dd, J=10.4, 6.0 Hz, 1H), 3.64 (m, 1H), 3.52 (m, 1H), 2.08 (s, 3H), 2.05 (s, 3H); MS (+)–ES [M+H]$^+$ m/z 385.3. Elemental Analysis calc'd for C$_{14}$H$_{16}$N$_4$O$_7$S.0.5 CH$_3$OH.0.2 CHCl$_3$: C, 41.61; H, 4.32; N, 13.21; S 7.56: Found: C, 41.73; H, 4.29; N, 12.86; S. 7.33.

Example 38

[2-Ethoxymethyl-1-(2-hydroxy-2-methyl-propyl)-1H-imidazo[4,5-c]quinolin-4-yl]-carbamic acid ethyl ester (39)

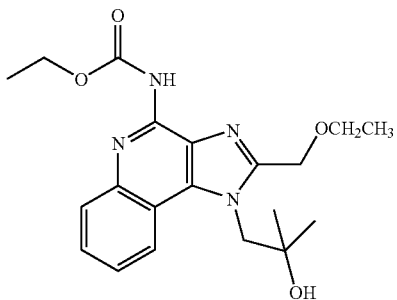

Step 1: Preparation of [2-Ethoxymethyl-1-(2-hydroxy-2-methyl-propyl)-]H-imidazo[4,5-

In a manner similar to step 1 of Example 8 except, substituting MeOH as the solvent, was prepared the title compound from 1-(4-amino-2-ethoxymethyl-imidazo[4,5-c]quinolin-1-yl)-2-methyl-propan-2-ol (38) (prepared according to the procedure given in International Publication No. WO 94/17043) and diethyl pyrocarbonate as an oil in 39% yield: $^1$H NMR (400 MHz, CDCl$_3$) δ 8.36 (d, J=8.0 Hz, 1H), 8.05 (d, J=8.0 Hz, 1H), 7.70 (t, J=7.2 Hz, 1H), 7.61 (t, J=8.0 Hz, 1H), 4.96 (br s, 2H), 4.80 (s, 2H), 4.39 (q, J=7.2 Hz, 2H), 3.62 (q, J=7.2 Hz, 2H), 1.40 (t, J=7.2 Hz, 3H), 1.36 (br s, 6H), 1.24 (t, J=6.8 Hz, 3H); MS(+)-ES [M+H]$^+$ 387.4 m/z.

6.4 Masking Effect of TLR7 Ligand Prodrugs

A typical experiment would use human peripheral blood mononuclear cells (PBMC) isolated from a healthy donor and placed in replicate cell culture wells; typically, 2×10$^6$ to 5×10$^6$ cells are placed in each well. The PBMC are incubated in the absence of test compounds at 37° C. in a humidified atmosphere containing 5% CO$_2$ for 24 hours to allow stabilization to the culture conditions, and then 100 micromolar isatoribine, the TLR7 ligand and a corresponding TLR7 ligand prodrug are added to separate wells containing PBMC from the same donor; untreated controls are included. The concentrations of TLR7 ligand and TLR7 ligand prodrug may be varied to suit the particular experiment, and the PBMC cultures are then incubated at 37° C. in a humidified atmosphere containing 5% CO$_2$ for a period of time ranging from two hours to 48 hours. Samples of cell culture supernate media are taken during the incubation. These are assayed for cytokine production by ELISA. Additionally the amount of TLR7 ligand and TLR7 ligand prodrug remaining at the end of the incubation may be assayed by LC-MS. Cytokine production is calculated relative to production in the isatoribine control, following subtraction of the cytokine production in untreated controls. The cytokine results are compared to determine the extent that the TLR7 ligand is more active than the corresponding TLR7 ligand prodrug.

Thus, if the TLR7 ligand generates more interferon alpha (a conveniently measured cytokine) than does the corresponding TLR7 ligand prodrug after a similar duration of exposure and concentration, the TLR7 ligand prodrug may be deemed a "masked" TLR7 ligand prodrug. The magnitude of reduction in cytokine production that constitutes "masking" may be as little as a 25% reduction relative to the parent TLR, since this would afford a corresponding increase in administered dose for a given level of tolerability.

Tables 9 through 14 provide data illustrating that TLR7 ligands of multiple chemical classes can be masked. The examples shown demonstrate substantial masking relative to the parent TLR7 ligand. The chemical substitutions shown are exemplary, and in no way restrictive of the invention, since additional chemical substitutions may also exhibit masking and are contemplated in the invention. Masking can be achieved by introduction of substitutions at a range of locations on any TLR7 ligand, and as shown can incorporate a variety of chemical linkages. It will be appreciated that the preferred substitution and linkage may vary for different parent TLR7 ligands.

TABLE 9

Masking of Isatoribine Prodrugs

| Parent molecule and its prodrugs | Compound No. | Amount of INFa relative to that induced by isatoribine at 100 μM, % |
|---|---|---|
| Parent molecule: Isatoribine | 21 | 100 |
| Prodrug: Amino acid ester | 24 | 1 |
| Prodrug: Deoxy | 93 | 0 |
| Prodrug: 6-Ethoxy | 77 | 0 |
| Prodrug: 6-Methoxy | 79 | 0 |
| Prodrug: Aminal | 84 | 0 |
| Prodrug: Aminal | 82 | 0 |
| Prodrug: Dioxolenone | 85 | 0 |

The masked property of isatoribine prodrugs can be demonstrated in a PBMC assay. The results of the PBMC assay (Table 9) show the amount of INFa released after exposure of the parent compound and its prodrugs for either 8 hours (val-isatoribine, 24) or 24 hours (other prodrugs) at the initial concentration of 100 μm. The amount of the released INFa was normalized to that induced by 100 μM of isotoribine at 100 μM in the same blood donor with the same exposure time.

TABLE 10

Masking of Loxoribine Prodrugs

| Parent molecule and its prodrugs | Compound No. | Amount of INFa relative to that induced by isatoribine at 100 μM, % |
|---|---|---|
| Parent molecule: Loxoribine | 17 | 50 |
| Prodrug: 6-Ethoxy | 45 | 0 |
| Prodrug: Deoxy | 43 | 0 |
| Prodrug: Valyl ester | 68 | 0 |

The masked property of loxoribine prodrugs can be demonstrated in a PBMC assay. The results of the PBMC assay (Table 10) show the amount of INFa released after exposure of the parent compound and its prodrugs for 24 hours at the initial concentration 100 μM. The amount of the released INFa was normalized to that induced by 100 μM of isotoribine at 100 μM in the same blood donor with the same exposure time.

TABLE 11

Masking of Imiquimod Prodrugs

| Parent molecule and its prodrugs | Compound No. | Amount of INFa relative to that induced by isatoribine at 100 μM, % |
|---|---|---|
| Parent molecule: Imiquimod | 31 | 60-76* |
| Prodrug: Pentyl carbamate | 34 | 0 |
| Prodrug: Ethyl carbamate | 50 | 0 |

*Results of two experiments with three different donors

The masked property of imiquimod prodrugs can be demonstrated in a PBMC assay. The results of the PBMC assay (Table 11) show the amount of INFa released after exposure of the parent compound and its prodrugs for 24 hours at the initial concentration 100 μM. The amount of the released INFa was normalized to that induced by 100 μM of isatoribine at 100 μM in the same blood donor with the same exposure time.

TABLE 12

Masking of Resiquimod Prodrugs

| Parent molecule and its prodrugs | Compound No. | Amount of INFa relative to that induced by isatoribine at 100 μM, % |
|---|---|---|
| Parent molecule: Resiquimod | 39 | 95 @ 1 μM |
| Prodrug: Ethyl Carbamate | 38 | 9 @ 100 μM |

The masked property of resiquimod prodrugs can be demonstrated in a PBMC assay. The results of the PBMC assay (Table 12) show the amount of INFa released after exposure of the parent compound and its prodrugs for 24 hours at the initial concentrations of either 1 or 100 μM. The amount of the released INFa was normalized to that induced by 100 μM of isatoribine at 100 μM in the same blood donor with the same exposure time.

TABLE 13

Masking of Bropirimine Prodrugs

| Parent molecule and its prodrugs | Compound No. | Amount of INFa relative to that induced by isatoribine at 100 μM, % |
|---|---|---|
| Parent molecule: Bropirimine | 35 | 22 |
| Prodrug: Deoxy | 48 | 0 |
| Prodrug: Ethoxy | 37 | 0 |
| Prodrug: Ethyl carbamate | 36 | 0 |
| Prodrug: Pentyl carbamate | 49 | 0 |

The masked property of bropirimine prodrugs can be demonstrated in a PBMC assay. The results of the PBMC assay (Table 13) show the amount of INFa released after exposure of the parent compound and its prodrugs for 24 hours at the initial concentration of 100 µM. The amount of the released INFa was normalized to that induced by 100 µM of Isatoribine at 100 µM in the same blood donor with the same exposure time.

TABLE 14

Masking of Adenine Prodrugs

| Parent molecule and its prodrugs | Compound No. | Amount of INFa relative to that induced by isatoribine at 100 µM, % |
|---|---|---|
| Parent molecule | 29 | 128 @ 0.1 µM |
| Prodrug: Methoxy | 65 | 0 @ 100 µM |
| Prodrug: Ethoxy | 64 | 0 @ 10 µM |
| Prodrug: Deoxy | 62 | 0 @ 0.1 µM |
| Prodrug: Ethyl carbonate | 51 | 18 @ 32 µM |
| Prodrug: Pentyl carbonate | 54 | 15 @ 10 µM |

The masked property of adenine prodrugs can be demonstrated in a PBMC assay. The results of the PBMC assay (Table 14) show the amount of INFa released after exposure of the parent compound and its prodrugs for 24 hours at different initial concentrations specified in the table. The amount of the released INFa was normalized to that induced by 100 µM of isatoribine at 100 µM in the same blood donor with the same exposure time.

TLR7 ligand prodrugs can also be assessed in vitro for their conversion to the active parent TLR7 ligand. This can be measured by incubation of the prodrug in blood, plasma, or in a cell culture of hepatocytes. At selected time intervals, samples are taken to determine the amount of prodrug remaining and the amount of TLR7 ligand produced. Such determinations are readily made by use of analytical tools known in the art such as LC-MS. The determination of the extent of conversion of a masked TLR7 ligand prodrug to the parent TLR7 ligand is useful in interpreting data wherein masking is apparent at shorter times but diminishes upon long incubations in the PBMC assay described herein. The rate of conversion of the prodrug to the TLR7 ligand may be determined to ensure that the cytokine results arise predominately from exposure to prodrug rather than from exposure to TLR7 ligand generated by rapid conversion of the prodrug under the conditions of the experiment.

6.5 Biological Testing of TLR7 Ligand Prodrugs Demonstrating

Increased Oral Availability and Decreased Side-Effects

Oral Availability

The improved bioavailability of TLR7 ligand prodrugs can be assessed by performing studies in vivo. In such experiments, the candidate prodrugs are administered by oral administration to mice, rats, monkeys, and/or dogs, and blood samples are taken at selected intervals. The blood samples are analysed for both the prodrug and the desired TLR7 ligand. Additional blood or liver samples may be analyzed for the presence of interferons and other cytokines that indicate functional activation of the TLR7 pathway in vivo. Desired candidates will demonstrate a blood exposure to the prodrug and also demonstrate a blood exposure to the desired TLR7 ligand of about 10% to 99% of the applied dose, as measured on a molar basis.

A representative example is the result obtained with the TLR7 ligand prodrug val-isatoribine (24), which as described below in the mouse and dog generated significant amounts of the parent TLR7 ligand isatoribine (21) in the blood. See U.S. patent application Ser. No. 10/305,061 (incorporated herein by reference in its entirety).

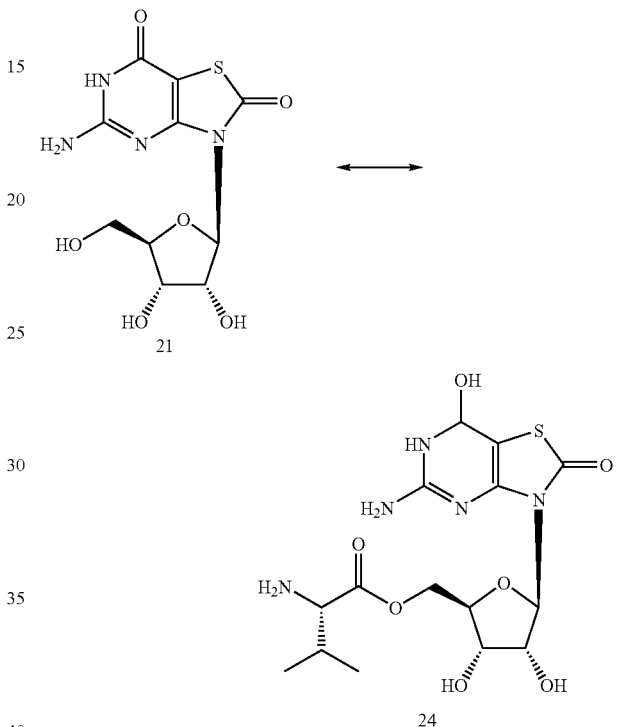

Interferon Alpha (Mu-IFN-α) Concentrations in Mice

The normal mouse provides a useful system for the assessment of the degree to which the inventions described herein provide material improvement in the oral delivery of 21 (isatoribine). Not only can one measure the plasma concentrations of isatoribine arising from oral administration of the said prodrug(s) but also the extensive immunological research conducted in the mouse has provided reagents suitable for measuring the levels of interferon alpha, a cytokine of interest reflecting one of the desired biologic activities of isatoribine.

We have used the murine system in a series of experiments that demonstrate that 24, the 5'-valine ester of 21 (val-isatoribine) elicits an interferon response substantially improved over that resulting from administration of isatoribine itself.

Table 15 records the results of an assay for murine interferon alpha in the plasma of mice that were dosed two times with isatoribine, formulated in bicarbonate, at a level of 50 mg/kg by the oral route. It is evident that no interferon was measurable even when the dose was repeated after an interval of four hours.

TABLE 15

Interferon Alpha (Mu-IFN-α) Plasma Concentration (pg/mL) in Mice Following Two Oral 50 mg/kg Doses of Isatoribine 4 Hours Apart

| Time, h | Individual Value | | | Mean | SD |
|---|---|---|---|---|---|
| First Dose | | | | | |
| 0.00 | $BQL^{50}$ | $BQL^{125}$ | $BQL^{50}$ | 0.00 | 0.00 |
| 0.03 | $BQL^{25}$ | $BQL^{250}$ | $BQL^{25}$ | 0.00 | 0.00 |
| 0.08 | $BQL^{25}$ | $BQL^{25}$ | $BQL^{25}$ | 0.00 | 0.00 |
| 0.25 | $BQL^{50}$ | $BQL^{25}$ | $BQL^{25}$ | 0.00 | 0.00 |
| 0.50 | $BQL^{25}$ | $BQL^{25}$ | $BQL^{25}$ | 0.00 | 0.00 |
| 1.00 | $BQL^{25}$ | $BQL^{25}$ | $BQL^{25}$ | 0.00 | 0.00 |
| 1.50 | $BQL^{100}$ | $BQL^{25}$ | $BQL^{25}$ | 0.00 | 0.00 |
| 2.00 | $BQL^{25}$ | $BQL^{75}$ | $BQL^{25}$ | 0.00 | 0.00 |
| 3.00 | $BQL^{25}$ | $BQL^{25}$ | $BQL^{25}$ | 0.00 | 0.00 |
| 4.00 | $BQL^{25}$ | $BQL^{25}$ | $BQL^{25}$ | 0.00 | 0.00 |
| Second Dose | | | | | |
| 4.03 | $BQL^{25}$ | $BQL^{25}$ | $BQL^{25}$ | 0.00 | 0.00 |
| 4.08 | $BQL^{25}$ | $BQL^{25}$ | $BQL^{25}$ | 0.00 | 0.00 |
| 4.25 | $BQL^{25}$ | $BQL^{25}$ | $BQL^{25}$ | 0.00 | 0.00 |
| 4.50 | $BQL^{50}$ | $BQL^{37.5}$ | $BQL^{50}$ | 0.00 | 0.00 |
| 5.00 | $BQL^{50}$ | $BQL^{50}$ | $BQL^{50}$ | 0.00 | 0.00 |
| 5.50 | $BQL^{37.5}$ | $BQL^{37.5}$ | $BQL^{37.5}$ | 0.00 | 0.00 |
| 6.00 | $BQL^{50}$ | $BQL^{41.3}$ | $BQL^{37.5}$ | 0.00 | 0.00 |
| 7.00 | $BQL^{50}$ | $BQL^{50}$ | $BQL^{50}$ | 0.00 | 0.00 |
| 8.00 | $BQL^{50}$ | $BQL^{25}$ | $BQL^{50}$ | 0.00 | 0.00 |

$BQL^n$—Below Elevated Quantifiable Limit <n pg/mL.

Table 16 records the results of assays for murine interferon alpha in the plasma of mice that first were dosed with bicarbonate and then four hours later were dosed orally with isatoribine, formulated in bicarbonate, at a level of 50 mg/kg. Interferon was reported in the plasma from four mice, including two that had received the bicarbonate vehicle dose. All the values reported in this experiment were low, and the reported interferon levels were not consistently reported for all three mice assessed at each time point, suggesting that these signals may be artifacts arising from measurement near the lower limits of the assay.

TABLE 16

Interferon Alpha (Mu-IFN-α) Plasma Concentration (pg/mL) in Mice Following One Vehicle Dose and One 50 mg/kg Doses of Isatoribine 4 Hours Later

| Time, h | Individual Value | | | Mean | SD |
|---|---|---|---|---|---|
| First Dose | | | | | |
| 0.00 | $BQL^{50}$ | $BQL^{100}$ | $BQL^{62.5}$ | 0.00 | 0.00 |
| 0.03 | $BQL^{50}$ | $BQL^{50}$ | $BQL^{37.5}$ | 0.00 | 0.00 |
| 0.08 | $BQL^{50}$ | $BQL^{50}$ | $BQL^{50}$ | 0.00 | 0.00 |
| 0.25 | $BQL^{50}$ | $BQL^{62.5}$ | $BQL^{50}$ | 0.00 | 0.00 |
| 0.50 | $BQL^{50}$ | $BQL^{50}$ | $BQL^{50}$ | 0.00 | 0.00 |
| 1.00 | $BQL^{50}$ | $BQL^{50}$ | $BQL^{100}$ | 0.00 | 0.00 |
| 1.50 | $BQL^{50}$ | $BQL^{100}$ | $BQL^{50}$ | 0.00 | 0.00 |
| 2.00 | 34.9 | $BQL^{25}$ | $BQL^{25}$ | 11.6 | 20.15 |
| 3.00 | $BQL^{25}$ | $BQL^{25}$ | $BQL^{25}$ | 0.00 | 0.00 |
| 4.00 | $BQL^{25}$ | 35.4 | $BQL^{100}$ | 11.8 | 20.44 |
| Second Dose | | | | | |
| 4.03 | $BQL^{25}$ | $BQL^{25}$ | $BQL^{25}$ | 0.00 | 0.00 |
| 4.08 | $BQL^{25}$ | $BQL^{25}$ | $BQL^{25}$ | 0.00 | 0.00 |
| 4.25 | $BQL^{25}$ | $BQL^{25}$ | $BQL^{25}$ | 0.00 | 0.00 |
| 4.50 | $BQL^{100}$ | $BQL^{25}$ | 133.2 | 44.4 | 76.90 |
| 5.00 | 74.9 | $BQL^{50}$ | NR | 37.5 | 52.96 |
| 5.50 | $BQL^{250}$ | $BQL^{75}$ | $BQL^{25}$ | 0.00 | 0.00 |
| 6.00 | $BQL^{25}$ | $BQL^{75}$ | $BQL^{75}$ | 0.00 | 0.00 |
| 7.00 | $BQL^{50}$ | $BQL^{50}$ | $BQL^{25}$ | 0.00 | 0.00 |
| 8.00 | $BQL^{25}$ | $BQL^{25}$ | $BQL^{25}$ | 0.00 | 0.00 |

$BQL^n$—Below Elevated Quantifiable Limit <n pg/mL.
NR—Not reportable.

Table 17 records the results of assays for murine interferon alpha in the plasma of mice that were dosed orally with val-isatoribine, dissolved in bicarbonate, at a dose that is equivalent to 50 mg/kg of isatoribine on a molar basis. It is evident that interferon was readily measurable at 1.0 hour, 1.5 hours, and 2.0 hours after dosing. Interferon was detected in all mice assayed at a given time point, indicating the reliability of the effect following val-isatoribine administration. Thus a single administration of val-isatoribine was superior to either a single dose or a repeated dose of isatoribine.

TABLE 17

Plasma Concentration (pg/mL) of Interferon Alpha (Mu-IFN-α) in Mice Following a Single 73.0 mg/kg Dose of Val-Isatoribine

| Time, h | Individual Value | | | Mean | SD |
|---|---|---|---|---|---|
| 0.00 | BQL | $BQL^{125}$ | $BQL^{25}$ | 0.00 | 0.00 |
| 0.25 | BQL | BQL | BQL | 0.00 | 0.00 |
| 0.50 | $BQL^{25}$ | $BQL^{25}$ | BQL | 0.00 | 0.00 |
| 0.75 | BQL | BQL | $BQL^{25}$ | 0.00 | 0.00 |
| 1.00 | 173.2 | 125.1 | 89.0 | 129.1 | 42.24 |
| 1.50 | 202.9 | 145.9 | 294.8 | 214.5 | 75.13 |
| 2.00 | 49.2 | 137.9 | 138.3 | 108.5 | 51.33 |
| 3.00 | $BQL^{25}$ | NR | NR | 0.00 | 0.00 |
| 4.00 | $BQL^{25}$ | 27.6 | BQL | 9.20 | 15.90 |
| 5.00 | BQL | $BQL^{25}$ | $BQL^{25}$ | 0.00 | 0.00 |

BQL—Below the Quantifiable Limit <12.5 pg/mL
$BQL^n$—Below the Elevated Quantifiable Limit <n pg/mL
NR—Not Reportable The data tabulated in Tables 15, 16, and 17 may be also considered from the point of view of the incidence of measurable interferon levels. Interferon was detected in the plasma of only 4 of the 114 mice used in the studies of isatoribine, whereas 10 of the 30 mice dosed with val-isatoribine had detectable interferon in their plasma. Thus, the prodrug increased the proportion of mice exhibiting an interferon response from 4% to 30% and the magnitude of both the average and peak response was increased twofold (100%).

In other experiments, plasma levels of isatoribine and interferon alpha were measured in mice that were dosed with isatoribine by the intravenous route, and these levels were compared to the levels of isatoribine and interferon alpha arising after oral administration of val-isatoribine. These data are summarized in FIG. 1. In this figure it is evident that the levels of interferon alpha induced by oral val-isatoribine ("val-isator") (at 50 mg/kg isatoribine molar equivalent) was similar to that from intravenous isatoribine ("isator") at 25 mg/kg. Thus, oral val-isatoribine provides levels of isatoribine and interferon that are approximately 50% of those observed after intravenous administration of isatoribine itself.

Beagle Dog

The effect of a prodrug (val-isatoribine, 24) on the systemic exposure to isatoribine (21) after oral administration to beagle dogs was investigated. Isatoribine was prepared in sodium bicarbonate solution. Val-isatoribine and isatoribine were prepared as the following formulations, which were chosen to ensure solubility:

Formulation 1: Isatoribine in sodium bicarbonate solution, 1 and 4 mg/mL.

Formulation 2: Val-isatoribine in phosphate buffered saline, 1.62 and 6.48 mg/mL, equivalent to 1 and 4 mg/mL of isatoribine on a molar basis.

Four male and four female adult beagle dogs weighing between 15 to 27 kg and approximately 1-2 years old were used at the beginning of the study. The animals were divided into 2 groups of 2 males and 2 females each. The test material was administered by gavage on Days 1 and 8, allowing a 7 day washout period between administrations. Blood samples (2 mL) were collected from each animal at predose, 15, 30 minutes, 1, 2, 3, 4, 6, 8 and 10 hours into lithium heparin tubes after each dosing. The plasma was frozen at −70° C. until analysis. The plasma was analyzed for isatoribine by an HPLC-MS/MS assay.

The pharmacokinetic parameters for isatoribine arising from isatoribine or val-isatoribine in each dog are summarized in Tables 18 and 19. The ratios for the key pharmacokinetic parameters defining the maximum concentration (Cmax) and total exposure as measured by the area under the time-concentration curve (AUC) for the prodrug and the bicarbonate solution at the 50 mg/kg dose are summarized in Table 20. For the prodrug 24, the Cmax ratio was 2.98±0.695 and the AUC ratio was 2.38±0.485. These results indicate that at 50 mg/kg dose, the prodrug val-isatoribine provided substantially higher Cmax and greater bioavailability than isatoribine in bicarbonate solution.

The ratios for the Cmax and AUC for the prodrug to the bicarbonate solution for the 10 mg/kg dose are summarized in Table 21. For the prodrug, the Cmax ratio was 2.24±0.249 and the AUC ratio was 1.82±0.529. These results indicate that at 10 mg/kg dose, the prodrug val-isatoribine provided higher Cmax and greater bioavailability than isatoribine in bicarbonate solution.

Thus, the maximum concentrations of isatoribine achieved after oral dosing are at least doubled, and the systemic exposure to isatoribine is enhanced by approximately 2-fold following oral administration of the prodrug val-isatoribine, compared to isatoribine itself, at both 10 and 50 mg/kg dose.

TABLE 18

Pharmacokinetic Parameters of Isatoribine in Dogs dosed at 50 mg/kg

| Animal Number | | Dosing Period 1 Formulation Isatoribine Dose, mg/kg molar equivalent isatoribine 50 | Dosing Period 2 Formulation Val-isatoribine Dose, mg/kg molar equivalent isatoribine 50 |
|---|---|---|---|
| Dog 3517322 | Cmax, ng/mL | 3038.7 | 11741.5 |
| | Tmax, h | 0.50 | 0.50 |
| | AUC(0-inf), ng · h/mL | 15227.0 | 33038.1 |
| | $T_{1/2}$, h | 6.4 | 2.4 |
| Dog 3521451 | Cmax, ng/mL | 3354.0 | 10652.1 |
| | Tmax, h | 1.00 | 1.00 |
| | AUC(0-inf), ng · h/mL | 9422.2 | 26552.7 |
| | $T_{1/2}$, h | 1.9 | 1.6 |
| Dog 3528707 | Cmax, ng/mL | 8915.3 | 20340.6 |
| | Tmax, h | 0.50 | 0.50 |
| | AUC(0-inf), ng · h/mL | 29701.7 | 53273.0 |
| | $T_{1/2}$, h | 2.2 | 2.3 |
| Dog 3532828 | Cmax, ng/mL | 6134.7 | 15987.9 |
| | Tmax, h | 0.50 | 0.50 |
| | AUC(0-inf), ng · h/mL | 12069.7 | 32987.0 |
| | $T_{1/2}$, h | 1.4 | 1.6 |

TABLE 19

Pharmacokinetic Parameters of Isatoribine in Dogs Dosed at 10 mg/kg

| Animal Number | | Dosing Period 1 Formulation Isatoribine Dose, mg/kg molar equivalent isatoribine 10 | Dosing Period 2 Formulation Val-isatoribine Dose, mg/kg molar equivalent isatoribine 10 |
|---|---|---|---|
| Dog 3524523 | Cmax, ng/mL | 4091.5 | 8594.6 |
| | Tmax, h | 1.00 | 0.50 |
| | AUC(0-inf), ng · h/mL | 13305.8 | 17166.2 |
| | $T_{1/2}$, h | 2.1 | 1.7 |
| Dog 3526402 | Cmax, ng/mL | 1859.5 | 4047.0 |
| | Tmax, h | 1.00 | 1.00 |
| | AUC(0-inf), ng · h/mL | 5774.4 | 10548.9 |
| | $T_{1/2}$, h | 1.6 | 2.2 |
| Dog 357450 | Cmax, ng/mL | 1620.3 | 4228.7 |
| | Tmax, h | 0.50 | 1.00 |
| | AUC(0-inf), ng · h/mL | 4387.3 | 11158.0 |
| | $T_{1/2}$, h | 1.5 | 2.3 |
| Dog 354708 | Cmax, ng/mL | 2781.2 | 5784.8 |
| | Tmax, h | 0.50 | 0.50 |
| | AUC(0-inf), ng · h/mL | 7522.1 | 12259.1 |
| | $T_{1/2}$, h | 1.6 | 2.0 |

TABLE 20

Ratio of Pharmacokinetic Parameters of Isatoribine in Dogs Dosed at 50 mg/kg

| Animal Number | Formulation | Isatoribine | Val-isatoribine |
|---|---|---|---|
| Dog 3517322 | Cmax Ratio | 1.00 | 3.86 |
| | AUC Ratio | 1.00 | 2.17 |
| Dog 3521451 | Cmax Ratio | 1.00 | 3.18 |
| | AUC Ratio | 1.00 | 2.82 |
| Dog 3528707 | Cmax Ratio | 1.00 | 2.28 |
| | AUC Ratio | 1.00 | 1.79 |
| Dog 3532828 | Cmax Ratio | 1.00 | 2.61 |
| | AUC Ratio | 1.00 | 2.73 |

TABLE 20-continued

Ratio of Pharmacokinetic Parameters of
Isatoribine in Dogs Dosed at 50 mg/kg

| Animal Number | Formulation | Isatoribine | Val-isatoribine |
|---|---|---|---|
| | Mean Cmax Ratio | N/A | 2.98 |
| | SD Cmax Ratio | N/A | 0.695 |
| | Mean AUC Ratio | N/A | 2.38 |
| | SD AUC Ratio | N/A | 0.485 |

TABLE 21

Ratio of Pharmacokinetic Parameters of
Isatoribine in Dogs Dosed at 10 mg/kg

| Animal Number | Formulation | Isatoribine | Val-isatoribine |
|---|---|---|---|
| Dog 3524523 | Cmax Ratio | 1.00 | 2.10 |
| | AUC Ratio | 1.00 | 1.29 |
| Dog 3526402 | Cmax Ratio | 1.00 | 2.18 |
| | AUC Ratio | 1.00 | 2.20 |
| Dog 3527450 | Cmax Ratio | 1.00 | 2.61 |
| | AUC Ratio | 1.00 | 2.54 |
| Dog 355708 | Cmax Ratio | 1.00 | 2.08 |
| | AUC Ratio | 1.00 | 1.63 |
| | Mean Cmax Ratio | N/A | 2.24 |
| | SD Cmax Ratio | N/A | 0.249 |
| | Mean AUC Ratio | N/A | 1.82 |
| | SD AUC Ratio | N/A | 0.529 |

The prodrug val-isatoribine is preferred for several reasons. First, the prodrug is easily formulated to provide a high proportion of active agent. This results in small capsule sizes for a given dose, which is an advantage for an oral product. Second, at the doses tested, val-isatoribine provides plasma levels of isatoribine that are well within the range desirable for biologic effect after oral administration, which is not the case for isatoribine itself.

Cynomolgus Monkey

From two to four male or female cynomolgus monkeys were used on the animal testing study. The study compound was formulated in a vehicle appropriate for animal oral or intravenous administration. The vehicles used were either as aqueous buffers or a solutions containing Cremophor. Animals were dosed via oral gavage or intravenous bolus injection for each test article. Blood samples (approximately 0.5 mL) were collected at predetermined time points (usually, pre-dose, 15, 30, and 45 minutes and at 1, 1.5, 2, 2.5, 3, 4, 8 and 24 hours post-dose), placed into tubes containing disodium EDTA. The samples were placed on wet ice following collection, and plasma separated as rapidly as possible. The plasma samples were aliquoted into a single vial, and stored frozen at approximately −20° C. until shipped on dry ice to the Sponsor. Animals were given food and water approximately 4 hours after the dose.

The plasma samples were analyzed for a prodrug and a parent compound using well-known LCMS/MS quantitation techniques by triple quadrupole instruments, i.e Sciex API3000. The quantitation results for the parent compound delivered by oral administration of the parent compound itself or by its prodrug administered orally were used to calculate the area-under-the-cureve (AUC) values from time zeto to 24 hours (PO AUCO-24 h). The comparison of the AUC values for the parent compound delivered into systemic circulation with that delivered by the prodrug allowed calculating relative oral bioavalibility of the prodrug. See results provided in Tables 22-26. When the AUC data for the parent compound delivered by the parent compound itself after its intravenous administration were available (AUC IV), it allowed calculating the absolute oral bioavailability by deviding the PO AUC (0-24 h) for the prodrug by the IV AUC (0-24 h) for the parent moleclule.

TABLE 22

Oral bioavailability of Isatoribine and its Prodrugs in Monkeys

| Parent molecule and its prodrugs | Structure | Oral bioavailability in cynomolgus monkey, % |
|---|---|---|
| Parent molecule: Isatoribine | 21 | 3 |
| Prodrug: Amino acid ester | 24 | 7-9* |
| Prodrug: Deoxy | 93 | 80 |
| Prodrug: 6-Ethoxy | 77 | 28 |
| Prodrug: 6-Methoxy | 79 | 21 |
| Prodrug: Aminal | 84 | 14 |
| Prodrug: Aminal | 82 | 4 |
| Prodrug: Dioxolenone | 85 | 17 |

*Average of multiple experiments at different doses.

TABLE 23

Oral bioavailability of Loxoribine and its Prodrugs in Monkeys

| Parent molecule and its prodrugs | Compound No. | Oral bioavailability in cynomolgus monkey, % |
|---|---|---|
| Parent molecule: Loxoribine | 17 | 2 |
| Prodrug: 6-Ethoxy | 45 | 9 |
| Prodrug: Deoxy | 43 | 13 |

TABLE 24

Oral bioavailability of Imiquimod and its Prodrugs in Monkeys

| Parent molecule and its prodrugs | Compound No. | Oral bioavailability in cynomolgus monkey, % |
|---|---|---|
| Parent molecule: Imiquimod | 31 | 100 AUC(0-24 h) = 9.0 |
| Prodrug: Pentyl carbamate | 34 | 555 AUC(0-24 h) = 50 |
| Prodrug: Ethyl carbamate | 50 | 234 AUC(0-24 h) = 21.1 |

TABLE 25

Oral bioavailability of Bropirimine and its Prodrugs in Monkeys

| Parent molecule and its prodrugs | Compound No. | Oral bioavailability in cynomolgus monkey, % |
|---|---|---|
| Parent molecule: Bropirimine | 35 | 100 |
| Prodrug: Deoxy | 48 | 137* |
| Prodrug: Ethoxy | 37 | 94 |
| Prodrug: Ethyl carbamate | 36 | 33 |
| Prodrug: Pentyl carbamate | 49 | 6 |

*The oral bioavailability exceeding 100% may be associated with gender differences since the parent compound was studied in male monkeys and the prodrug was studied in female monkeys.

TABLE 26

Oral bioavailability of Adenine Prodrugs in Monkeys

| Parent molecule and its prodrugs | Compound No. | Oral bioavailability in cynomolgus monkey, % |
|---|---|---|
| Parent molecule: | 29 | 46 |
| Prodrug: Methoxy | 65 | 1.3 |
| Prodrug: Ethoxy | 64 | 4.6 |
| Prodrug: Deoxy | 62 | 0.7 |
| Prodrug: Pentyl carbonate | 54 | 9.7 |

Reduction of Gastrointestinal Irritancy

TLR7 ligand prodrugs of the invention also demonstrate unexpected and greatly reduced toxicology effects, and in particular reduced GI irritancy.

The gastrointestinal ("GI") tract is lined with substantial immune tissue (e.g., Peyer's patches, etc.). TLR7 ligand prodrugs offer the prospect of masking the active structure as the agent passes through lymphoid tissue lining the gut, which should minimize activation of this tissue and thereby reduce GI irritancy.

Robins et al. have shown that elimination of the 5'-hydroxyl of isatoribine nucleoside eliminates activity. See Robins et al., *Adv. Enzyme Regul.*, 29, 97-121 (1989). Without being limited to any particular theory, it was hypothesized that blockade of this hydroxyl site by an ester substitution would similarly eliminate activity but allow transport in the systemic circulation, where the valine ester would be cleaved and result in exposure to isatoribine.

We have found that the hypothesis was confirmed. Formal toxicology studies of intravenously administered isatoribine and orally administered isatoribine and val-isatoribine were conducted in beagle dogs. The toxicology results for orally administered isatoribine are from a study conducted by ICN/Nucleic Acid Research Institute.

We compared in the dog the oral toxicology of 21 and 24, and the intravenous toxicology of 21. We observed that the oral toxicology of 24 was much more like intravenous 21 than it was like oral 21. In particular, the dose limiting toxicology of oral 3 was similar in nature to that of intravenous 21, and occurred at blood exposures that were similar to those observed after intravenous 21. In contrast, oral 21 had a different limiting toxicity (gastrointestinal lesions) and this toxicity was observed at a dose lower than the toxic dose of either intravenous 21 or oral 24. Also, emesis was observed in dogs treated with oral 21 at doses lower than the dose of oral 24 that resulted in emesis. See Table 27. Other systems for assessment of emesis also are known, such as in ferrets, allowing comparison of oral and intravenous administration of compounds. See, e.g., Strominger N. et al., *Brain Res. Bull*, 5, 445-451 (2001).

In each case the compound was administered as a solution, by gavage or by intravenous infusion. Multiple parameters were assessed, as is customary in a toxicology study. In the studies providing higher potential exposure to isatoribine, the plasma concentration of isatoribine was assessed by a LC/MS method. The notable GI findings were graded and are listed in Table 27.

TABLE 27

Effect on GI Tolerance in Dogs after Dosing of Isatoribine (21) or Val-Isatoribine (24) Ranked by Systemic Exposure (AUC) to Isatoribine in Toxicology Studies.

| Isatoribine equivalent applied dose (mg/kg) | $AUC_{0-24\,hrs}$ (µg · hr/ml) | Oral Isatoribine | | IV Isatoribine | | Oral Val-Isatoribine | |
|---|---|---|---|---|---|---|---|
| | | Emesis or loose stool | GI lesions or Irritation | Emesis or loose stool | GI lesions or irritation | Emesis or loose stool | GI lesions or irritation |
| 2.5 | n.d | Neg. | Neg. | | | | |
| 5 | n.d. | + | Neg. | | | | |
| 10 | n.d. | ++ | ++ | | | | |
| 8.1 | 11.4 | | | | | Neg. | Neg. |
| 16 | 15.6 | | | | | Neg. | Neg. |
| 12.5 | 19.5 | | | Neg. | Neg. | | |
| 32 | 31.7 | | | | | Neg. | Neg. |
| 25 | 42.8 | | | Neg. | Neg. | | |
| 64 | 71 | | | | | Neg. | Neg. |
| 130 | 75.3 | | | | | + | Neg. |
| 50 | 87.8 | | | + | Neg. | | |
| 260 | 127 | | | | | ++ | Neg. |

TABLE 27-continued

Effect on GI Tolerance in Dogs after Dosing of Isatoribine (21) or Val-Isatoribine (24) Ranked by Systemic Exposure (AUC) to Isatoribine in Toxicology Studies.

| Isatoribine equivalent applied dose (mg/kg) | $AUC_{0-24\,hrs}$ (µg · hr/ml) | Oral Isatoribine Emesis or loose stool | Oral Isatoribine GI lesions or Irritation | IV Isatoribine Emesis or loose stool | IV Isatoribine GI lesions or irritation | Oral Val-Isatoribine Emesis or loose stool | Oral Val-Isatoribine GI lesions or irritation |
|---|---|---|---|---|---|---|---|
| 390 | 180 | | | | | +++ | Neg. |
| 100 | 209 | | | ++ | Neg. | | |

For orally administered isatoribine the principal findings were related to GI tolerability as measured by GI irritancy. The clinical signs noted in Table 27 were emesis and/or loose stools. These clinical signs were more frequent in the 10 mg/kg group, and in one animal at this dose a bloody stool was noted. Gross histopathologic evaluation of the GI tract noted multiple, scattered red lesions on the intestinal mucosa in four of eight dogs at 10 mg/kg, which on microscopic evaluation revealed cellular congestion and hemorrhage, as might be expected for an ongoing localized inflammatory process. The GI effects established the NOAEL as 5 mg/kg.

Intravenously administered isatoribine resulted in emesis and/or loose stools as a common finding in dogs; this effect occurred at substantially higher applied doses than orally administered isatoribine. No lesions were seen in the GI tract either at necropsy or histopathologic evaluation of tissues. The GI toxicity did not affect the NOAEL, which was established as 12.5 mg/kg on the basis of other findings.

Orally administered val-isatoribine demonstrated a toxicology profile similar to intravenously administered isatoribine. At higher applied doses, emesis and loose stools were observed. No GI lesions were found, although this was a focus of evaluation in this study. As for intravenously administered isatoribine, the NOAEL was established on the basis of other findings. The correspondence of observed toxicity to systemic exposures of isatoribine is of interest in this study; the threshold of isatoribine AUC for observation of emesis and loose stools is similar for intravenously administered isatoribine and orally administered val-isatoribine (Table 27).

The data in Table 27 indicate that orally administered val-isatoribine provides an improved toxicity profile over orally administered isatoribine, and is consistent with the hypothesis that chemical masking of the activity of isatoribine is afforded by chemically substituting an ester at the 5'-hydroxyl position of the nucleoside. As illustrated in Tables 9 through 14, it is possible to chemically mask any TLR7 ligand using a variety of substituents. Engineering this substitution to be cleavable upon entry into the body affords systemic exposure to the useful activity of the compound without the limiting GI toxicity arising from the anatomical structure of the GI tract. As illustrated in Tables 22 through 25, it is possible to design the chemical substitution on a masked TLR7 ligand to be cleavable after administration. Thus, masked TLR7 ligand prodrugs can be generated for any TLR7 ligand. This enables administration of doses that are substantially higher on a molar basis than otherwise would be acceptable, with the result of greater efficacy and reduced side effects when compared to administration of the parental "unmasked" compound alone.

6.6 Oral Composition

Table 28 illustrates a batch formulation and a single dose unit formulation containing 100 mg of val-isatoribine.

TABLE 28

Formulation for 100 mg tablet

| Material | Percent by Weight | Quantity (mg/tablet) | Quantity (kg/batch) |
|---|---|---|---|
| val-isatoribine | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and val-isatoribine components are passed through a #30 mesh screen (about 430µ to about 655µ). The Pluronic F-68® (manufactured by JRH Biosciences, Inc. of Lenexa, Kans.) surfactant is passed through a #20 mesh screen (about 457µ to about 1041µ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The thalidomide is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

6.7 Mucosal Composition

A concentrate is prepared by combining isatoribine, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| val-isatoribine | 0.0120 g |
| trichloromonofluoromethane | 1.6960 g |
| dichlorodifluoromethane | 3.7028 g |
| dichlorotetrafluoroethane | 1.5766 g |
| total | 7.0000 g |

6.8 Intravenous Composition

The intravenous formulation is prepared by reconstituting a compound of the invention with an appropriate liquid medium, such as water for injection (WFI) or a 5% dextrose solution. A desired concentration of the intravenous formulation can be obtained by reconstituting an appropriate amount of a compound of the invention with an appropriate volume of liquid medium. A desired concentration of the intravenous formulation provides a therapeutically effective amount of a compound of the invention to the patient, preferably a mammal, more preferably a human, in need of the intravenous pharmaceutical formulation and maintains a therapeutically effective level of a compound of the invention in the patient. The dose which is therapeutically effective will depend on the rate at which the intravenous formulation is delivered to the patient and the concentration of the intravenous formulation.

For example, one vial containing a composition (e.g., 50 mg of a compound of the invention per vial) are reconstituted with a 5% dextrose solution (14 ml of 5% dextrose solution per vial) yielding a total of 25 mL of solution. The reconstituted solution is incorporated into a dextrose solution in an infusion bag and q.s. to 50 mL, resulting in a solution containing 1 mg/ml of a compound of the invention suitable for intravenous infusion administration. The preferred concentration of a compound of the invention in the liquid medium, in the infusion bag, is about 0.001 to about 3 mg/ml, preferably about 0.75 to about 1 mg/ml.

The foregoing has demonstrated the pertinent and important features of the present invention. Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of treating a hepatitis C virus infection in a patient comprising orally administering to the patient in need thereof a masked TLR7 ligand prodrug or a pharmaceutically acceptable salt thereof, wherein the oral administration of the masked TLR7 ligand prodrug achieves a therapeutically effective plasma concentration of the TLR7 ligand, and wherein the masked TLR7 ligand prodrug is an analog of guanosine.

2. The method of claim 1 wherein the prodrug is selected from an (a) ester, ether, or aminal moiety after conversion of a TLR7 ligand alcohol substituent, or (b) deoxygenated moiety after conversion of a TLR7 ligand oxo substituent of guanosine or analog of guanosine.

3. The method of claim 1 wherein the masked TLR7 ligand prodrug is selected from

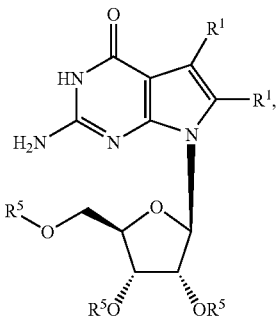

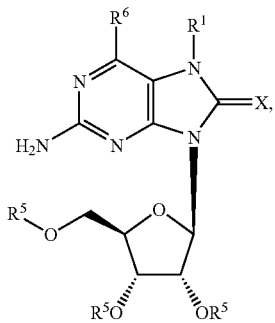

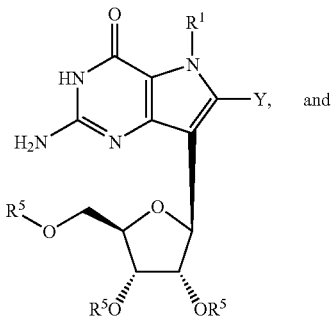

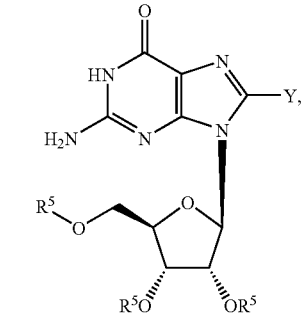

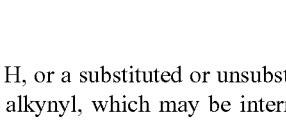

wherein:

each $R^1$ is H, or a substituted or unsubstituted alkyl, alkenyl, or alkynyl, which may be interrupted by one or more O, S, or N heteroatoms, or a substituted or unsubstituted aryl or heteroaryl;

$R^4$ is a substituted or unsubstituted alkyl;

$R^5$ is independently H, —C(O)($C_{1-8}$alkyl), or a racemic, L-, or D-amino acid group —C(O)CHNH$_2$R$^9$;

$R^6$ is H, OR$^{10}$, or N(R$^{11}$)$_2$;

$R^9$ is H, or a substituted or unsubstituted alkyl, C(O)CH($C_{1-6}$ alkyl)NH$_2$, or —C(O)CH(CH$_2$-aryl)NH$_2$;

$R^{10}$ is independently H, $C_{1-6}$ alkyl, $C_{3-7}$ alkenyl, $C_{3-7}$ alkynyl, —$(CR^{12}R^{13})_t(C_6$-$C_{10}$aryl), —$(CR^{12}R^{13})_t(C_3$-$C_{10}$ cycloalkyl), —$(CR^{12}R^{13})_t(C_4$-$C_{10}$ heterocyclic), —$(CR^{12}R^{13})_{t>1}$OH, —$(CR^{12}R^{13})_{t>0}$CO$_2$C$_{1-18}$ alkyl, and —$(CR^{12}R^{13})_{t>0}$N(R$^{14}$)CO$_2$C$_{1-18}$ alkyl, and SO$_2$(aryl), wherein t is an integer from 0 to 6 unless otherwise indicated, and wherein the alkyl, alkenyl, alkynyl, aryl, cycloalkyl, and heterocyclic moieties of the foregoing groups are optionally substituted with substituents independently selected from halo, cyano, nitro, trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —NH$_2$, —NH-alkyl, —N(alkyl)$_2$, —NH-aryl, —N(alkyl)(aryl), —N(aryl)$_2$, —NHCHO, —NHC(O)alkyl, —NHC(O)aryl, —N(alkyl)C(O)H, —N(alkyl)C(O)alkyl, —N(aryl)C(O)H, —N(aryl)C(O)alkyl, —NHCO$_2$alkyl, —N(alkyl)CO$_2$alkyl, —NHC(O)NH$_2$, —N(alkyl)C(O)NH$_2$, —NHC(O)NH-alkyl, —NHC(O)N(alkyl)$_2$, —N(alkyl)C(O)NH-alkyl, N(alkyl)C(O)N(alkyl)$_2$, —NHSO$_2$-alkyl, —N(alkyl)SO$_2$-alkyl, —C(O)alkyl, —C(O)aryl, —OC(O)alkyl, —OC(O)aryl, —CO$_2$-alkyl, —CO$_2$-aryl, —CO$_2$H, —C(O)NH$_2$, —C(O)NH-alkyl, —C(O)N(alkyl)$_2$, —C(O)NH-aryl, —C(O)N(aryl)$_2$, —C(O)N(alkyl)(aryl), —S(O)alkyl, —S(O)aryl, —SO$_2$alkyl, —SO$_2$aryl, —SO$_2$NH$_2$, —SO$_2$NH-alkyl, and —SO$_2$N(alkyl)$_2$;

$R^{11}$ is independently H, $C_{1-6}$ alkyl, $C_3$-$C_{10}$ cycloalkyl, or together with nitrogen forms a 5- or 6-membered heterocyclic ring;

$R^{12}$ and $R^{13}$ are independently H, $C_{1-6}$ alkyl, $C_{2-6}$ alkenyl, or $C_{2-6}$ alkynyl;

$R^{14}$ is H, $C_{1-6}$ alkyl, or —CH$_2$-aryl;

X is O or S;

Y is H, halo, OH, OR$^4$, SH, SR$^4$, NH$_2$, NHR$^4$, N(R$^4$)$_2$, or a substituted or unsubstituted alkyl or aryl; and or stereoisomer or a pharmaceutically acceptable salt thereof.

4. The method of claim 3 wherein $R^1$ is H or a substituted or unsubstituted alkyl, alkenyl, or alkynyl; $R^5$ is independently H, —C(O)(C$_{1-18}$alkyl), or a racemic, L-, or D-amino acid group —C(O)CHNH$_2$R$^9$, wherein R$^9$ is an unsubstituted alkyl; $R^6$ is H or OR$^{10}$, wherein R$^{10}$ is independently $C_{1-6}$ alkyl, $C_{3-7}$ alkenyl, $C_{3-7}$ alkynyl, —(CR$^{12}$R$^{13}$)$_t$(C$_6$-C$_{10}$ aryl), —(CR$^{12}$R$^{13}$)$_t$(C$_4$-C$_{10}$ heterocyclic), and —(CR$^{12}$R$^{13}$)$_{t>0}$N(R$^{14}$)CO$_2$C$_{1-8}$ alkyl, wherein t is an integer from 0 to 4 unless otherwise indicated, and wherein the alkyl, alkenyl, aryl, and heterocyclic moieties of the foregoing groups are optionally substituted with 1 to 3 substituents independently selected from halo, cyano, nitro, trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —CO$_2$-alkyl, —CO$_2$-aryl, —OC(O)alkyl, and —OC(O)aryl, and wherein R$^{12}$ and R$^{13}$ are independently H, $C_{1-6}$ alkyl, or $C_{2-6}$ alkenyl; and R$^{14}$ is H, —CH$_3$, or —CH$_2$CH$_3$; X is O or S; and Y is H, halo, OH, OR$^4$, SH, or SR$^4$.

5. The method of claim 1 wherein the masked TLR7 ligand prodrug is selected from

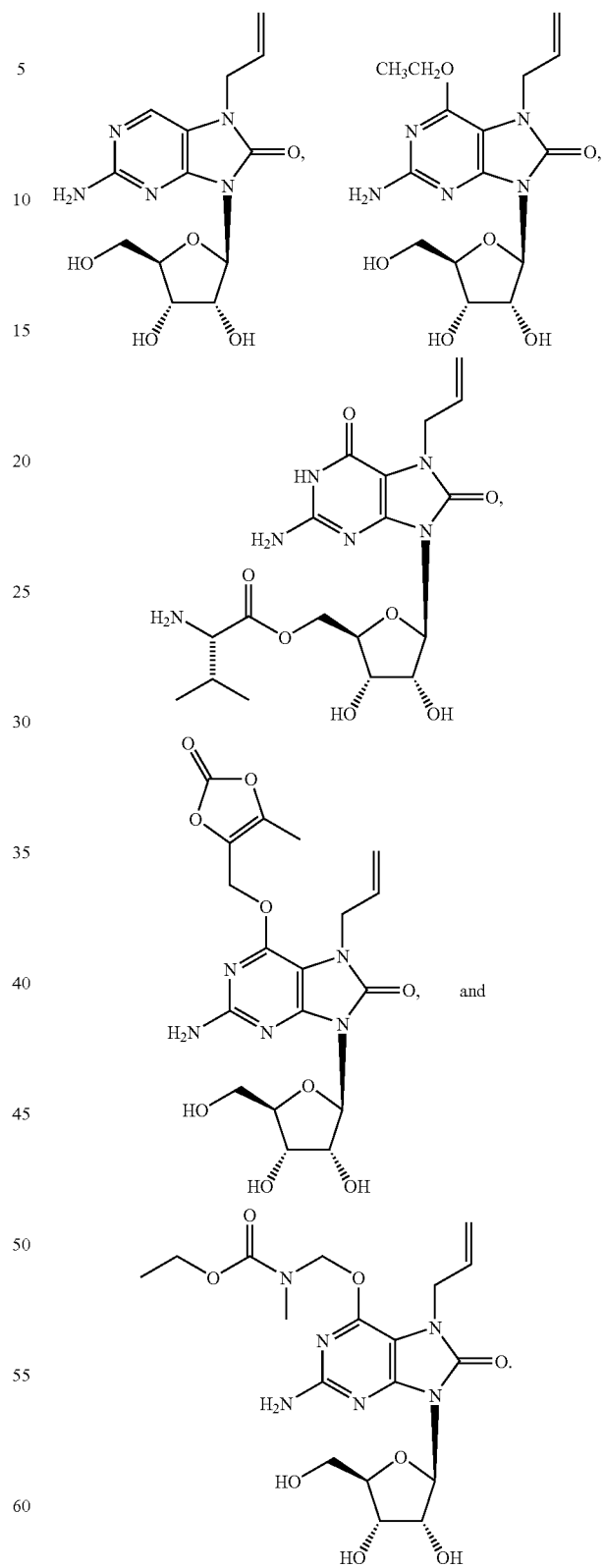

6. The method of claim 1 wherein the oral administration of the masked TLR7 ligand prodrug achieves an in vivo effective plasma concentration of the TLR7 ligand that is 10% to 500% of the effective in vivo exposure obtained upon oral administration of the TLR7 ligand alone.

7. The method of claim 1 wherein the oral administration of the masked TLR7 ligand prodrug achieves an in vivo effective plasma concentration of the TLR7 ligand that is 50% to 200% of the effective in vivo exposure obtained upon oral administration of the TLR7 ligand alone.

8. The method of claim 1 wherein the oral administration of the masked TLR7 ligand prodrug reduces undesirable side effects in a patient relative to the side effects upon oral administration of the TLR7 ligand alone.

9. The method of claim 1 wherein the oral administration of the masked TLR7 ligand prodrug reduces undesirable side effects by 50% in a patient relative to the side effects upon oral administration of the TLR7 ligand alone.

10. The method of claim 8, wherein the side effect is gastrointestinal irritancy.

11. The method of claim 10 wherein the irritancy is hemorrhage.

12. The method of claim 10 wherein the irritancy is lesions.

13. The method of claim 10 wherein the irritancy is emesis.

14. The method of claim 1 wherein the patient is human.

15. The method of claim 1 further comprising administering a pharmaceutically acceptable excipient, carrier, or vehicle.

16. The method of claim 1 further comprising administering an additional therapeutic agent.

17. The method of claim 16 wherein the additional therapeutic agent is an antiviral agent.

18. The method of claim 1 wherein the therapeutically effective dose is 0.001 to 100 mg/kg per day.

19. The method of claim 18 wherein the therapeutically effective dose is about 0.1 to 25 mg/kg per day.

20. The method of claim 19 wherein the therapeutically effective dose is about 1 to 20 mg/kg per day.

* * * * *